(12) United States Patent
Bokvist et al.

(10) Patent No.: US 7,897,573 B2
(45) Date of Patent: *Mar. 1, 2011

(54) SELECTIVE VPAC2 RECEPTOR PEPTIDE AGONISTS

(75) Inventors: Bengt Krister Bokvist, Hamburg (DE); Lianshan Zhang, Carmel, IN (US); Jorge Alsina-Fernandez, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/508,584

(22) Filed: Jul. 24, 2009

(65) Prior Publication Data

US 2010/0009916 A1 Jan. 14, 2010

Related U.S. Application Data

(63) Continuation of application No. 12/090,656, filed as application No. PCT/US2006/041550 on Oct. 24, 2006, now Pat. No. 7,582,608.

(60) Provisional application No. 60/743,364, filed on Feb. 28, 2006, provisional application No. 60/740,342, filed on Nov. 29, 2005, provisional application No. 60/730,291, filed on Oct. 26, 2005.

(51) Int. Cl.
*A61K 38/16* (2006.01)
(52) U.S. Cl. ...................................... 514/13.1
(58) Field of Classification Search ........................ None
See application file for complete search history.

(56) References Cited

U.S. PATENT DOCUMENTS

| 6,242,563 | B1 | 6/2001 | Dong |
| 2004/0058870 | A1 | 3/2004 | Froland et al. |

FOREIGN PATENT DOCUMENTS

| EP | 0 450 100 | 10/1991 |
| JP | 06 092991 | 4/1994 |
| WO | WO 98/02453 | 1/1998 |
| WO | WO 00/05260 | 2/2000 |
| WO | WO 00/66629 | 11/2000 |
| WO | WO 01/23420 | 4/2001 |
| WO | WO 03/058203 | 7/2003 |
| WO | WO 03/099314 | 12/2003 |
| WO | WO 2004/006839 | 1/2004 |
| WO | WO 2005/058954 | 6/2005 |
| WO | WO 2005/072385 | 8/2005 |
| WO | WO 2006/023356 | 3/2006 |
| WO | WO 2006/023358 | 3/2006 |
| WO | WO 2006/042152 | 4/2006 |
| WO | WO 2007/044591 | 4/2007 |
| WO | WO 2008/043102 | 4/2008 |

OTHER PUBLICATIONS

International Search Report of corresponding International Application No. PCT/US2006/041550, dated Feb. 15, 2007.

*Primary Examiner*—Christina Bradley
(74) *Attorney, Agent, or Firm*—Andrea M. Castetter

(57) ABSTRACT

The present invention encompasses peptides that selectively activate the VPAC2 receptor and are useful in the treatment of diabetes.

6 Claims, 1 Drawing Sheet

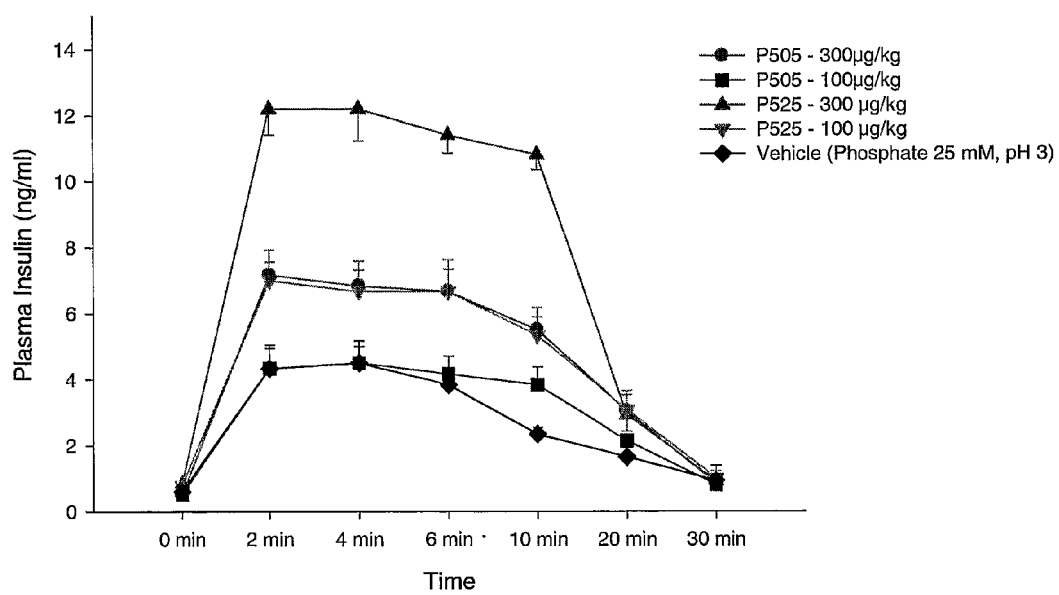
Figure 1. Insulinotrophic activity of P505 and P525 in normal Wistar rats. Compound was injected 24h prior to the i.v. glucose challenge.

SELECTIVE VPAC2 RECEPTOR PEPTIDE AGONISTS

This application is a continuation of U.S. national phase application Ser. No. 12/090,656, filed Apr. 18, 2008, now U.S. Pat. No. 7,582,608 which claims priority to PCT/US2006/041,550, filed Oct. 24, 2006, which claims priority to U.S. provisional patent application 60/743,364, filed 28 Feb. 2006, U.S. provisional patent application 60/740,342, filed 29 Nov. 2005, and U.S. provisional patent application 60/730,291 filed 26 Oct. 2005.

The present invention relates to selective VPAC2 receptor peptide agonists.

In particular, the present invention relates to selective VPAC2 receptor peptide agonists which are covalently attached to one or more molecules of polyethylene glycol or a derivative thereof.

Type 2 diabetes, or non-insulin dependent diabetes mellitus (NIDDM), is the most common form of diabetes, affecting 90% of people with diabetes. With NIDDM, patients have impaired β-cell function resulting in insufficient insulin production and/or decreased insulin sensitivity. If NIDDM is not controlled, excess glucose accumulates in the blood, resulting in hyperglycemia. Over time, more serious complications may arise including renal dysfunction, cardiovascular problems, visual loss, lower limb ulceration, neuropathy, and ischemia. Treatments for NIDDM include improving diet, exercise, and weight control as well as using a variety of oral medications. Individuals with NIDDM can initially control their blood glucose levels by taking such oral medications. These medications, however, do not slow the progressive loss of β-cell function that occurs in NIDDM patients and, thus, are not sufficient to control blood glucose levels in the later stages of the disease. Also, treatment with currently available medications exposes NIDDM patients to potential side effects such as hypoglycemia, gastrointestinal problems, fluid retention, oedema, and/or weight gain.

Pituitary adenylate cyclase-activating peptide (PACAP) and vasoactive intestinal peptide (VIP) belong to the same family of peptides as secretin and glucagon. PACAP and VIP work through three G-protein-coupled receptors that exert their action through the cAMP-mediated and other $Ca^{2+}$-mediated signal transduction pathways. These receptors are known as the PACAP-preferring type 1 (PAC1) receptor (Isobe, et al., *Regul. Pept.*, 110:213-217 (2003); Ogi, et al., *Biochem. Biophys. Res. Commun.*, 196:1511-1521 (1993)) and the two VIP-shared type 2 receptors (VPAC1 and VPAC2) (Sherwood et al., *Endocr. Rev.*, 21:619-670 (2000); Hammar et al., *Pharmacol Rev*, 50:265-270 (1998); Couvineau, et al., *J. Biol. Chem.*, 278:24759-24766 (2003); Sreedharan, et al., *Biochem. Biophys. Res. Commun.*, 193: 546-553 (1993); Lutz, et al., *FEBS Lett.*, 458: 197-203 (1999); Adamou, et al., *Biochem. Biophys. Res. Commun.*, 209: 385-392 (1995)). A series of PACAP analogues is disclosed in U.S. Pat. No. 6,242,563 and WO 2000/05260.

PACAP has comparable activities towards all three receptors, whilst VIP selectively activates the two VPAC receptors (Tsutsumi et al., *Diabetes*, 51:1453-1460 (2002)). Both VIP (Eriksson et al., *Peptides*, 10: 481-484 (1989)) and PACAP (Filipsson et al., *JCEM*, 82:3093-3098 (1997)) have been shown to not only stimulate insulin secretion in man when given intravenously but also increase glucagon secretion and hepatic glucose output. As a consequence, PACAP or VIP stimulation generally does not result in a net improvement of glycemia. Activation of multiple receptors by PACAP or VIP also has broad physiological effects on nervous, endocrine, cardiovascular, reproductive, muscular, and immune systems (Gozes et al., *Curr. Med. Chem.*, 6:1019-1034 (1999)). It appears that VIP-induced watery diarrhoea in rats is mediated by only one of the VPAC receptors, VPAC1 (Ito et al., *Peptides*, 22:1139-1151 (2001); Tsutsumi et al., *Diabetes*, 51:1453-1460 (2002)). The VPAC1 and PAC1 receptors are expressed on α-cells and hepatocytes and, thus, are most likely involved in the effects on hepatic glucose output.

Exendin-4 is found in the salivary excretions from the Gila Monster, *Heloderma Suspectum*, (Eng et al., *J. Biol. Chem.*, 267(11):7402-7405 (1992)). It is a 39 amino acid peptide, which has glucose dependent insulin secretagogue activity. Particular PEGylated Exendin and Exendin agonist peptides are described in WO 2000/66629.

Recent studies have shown that peptides selective for the VPAC2 receptor are able to stimulate insulin secretion from the pancreas without gastrointestinal (GI) side effects and without enhancing glucagon release and hepatic glucose output (Tsutsumi et al., *Diabetes*, 51:1453-1460 (2002)). Peptides selective for the VPAC2 receptor were initially identified by modifying VIP and/or PACAP. (See, for example, Xia et al., *J Pharmacol Exp Ther.*, 281:629-633 (1997); Tsutsumi et al., *Diabetes*, 51:1453-1460 (2002); WO 01/23420 and WO 2004/06839.)

Many of the VPAC2 receptor peptide agonists reported to date have, however, less than desirable potency, selectivity, and stability profiles, which could impede their clinical viability. In addition, many of these peptides are not suitable for commercial candidates as a result of stability issues associated with the polypeptides in formulation, as well as issues with the short half-life of these polypeptides in vivo. It has, furthermore, been identified that some VPAC2 receptor peptide agonists are inactivated by dipeptidyl-peptidase (DPP-IV). A short serum half-life could hinder the use of these agonists as therapeutic agents. There is, therefore, a need for new therapies, which overcome the problems associated with current medications for NIDDM.

The present invention seeks to provide improved compounds that are selective for the VPAC2 receptor and which induce insulin secretion from the pancreas only in the presence of high blood glucose levels. The compounds of the present invention are peptides, which are believed to also improve beta cell function. These peptides can have the physiological effect of inducing insulin secretion without GI side effects or a corresponding increase in hepatic glucose output and also generally have enhanced selectivity, potency, and/or in vivo stability of the peptide compared to known VPAC2 receptor peptide agonists.

The present invention also seeks to provide selective VPAC2 receptor peptide agonists, which have reduced clearance and improved in vivo stability. It is desirable that the agonists of the present invention be administered a minimum number of times during a prolonged period of time.

According to a first aspect of the invention, there is provided a PEGylated VPAC2 receptor peptide agonist comprising a sequence selected from:

```
                                          SEQ ID NO: 17
HSDAVFTEQY(OMe)TRAibRAibQLAAAibOrnY(OMe)LQSIK
AibOrn;

SEQ ID NO: 18
HSDAVFTEK(CO(CH2)2SH)Y(OMe)TOrnLRAibQVAAAibOrn
YLQSIOrnOrn;

SEQ ID NO: 19
HSDAVFTEQY(OMe)TOrnLRAibQVAAAibOrnYLQSIOrnK(W)
Orn;
```

-continued

SEQ ID NO: 20
HSDAVFTEQY(OMe)TOrnLRAibQVAAAibK(CO(CH$_2$)$_2$SH)YLQSIOrnOrn;

SEQ ID NO: 21
HSDAVFTEQY(OMe)TOrnLRAibQVAAK(CO(CH$_2$)$_2$SH)OrnYLQSIOrnOrn;

SEQ ID NO: 22
HSDAVFTEQY(OMe)TOrnLRAibQVCAAibOrnYLQSIOrnOrn;

SEQ ID NO: 23
HSDAVFTEQY(OMe)TOrnLRCQVAAAibOrnYLQSIOrnOrn;

SEQ ID NO: 24
HSDAVFTEQY(OMe)TOrnLRAibQLAAAibOrnYLQSIOrnOrn;

SEQ ID NO: 25
HSDAVFTEQY(OMe)TOrnLRAibQVAAAibOrnYAibQSIOrnOrn;

SEQ ID NO: 26
HSDAVFTEQY(OMe)TOrnLRAibQVAAAibOrnYLQAibIOrnOrn;

SEQ ID NO: 27
HSDAVFTEQY(OMe)TOrnLRAibQVAAbuAibOrnYLQAibIOrnOrn;

SEQ ID NO: 28
HSDAVFTEQY(OMe)TOrnLRAibQLAAAibOrnYLQAibIOrnOrn;

SEQ ID NO: 29
HSDAVFTEQY(OMe)TOrnLRAibQLAAAibOrnYAibQAibIOrnOrn;

SEQ ID NO: 30
HSDAVFTEQY(OMe)TOrnLRAibQLAAbuAibOrnYAibQSIOrnOrn;

SEQ ID NO: 31
HSDAVFTEQY(OMe)TOrnLRAibQLAAbuAibOrnYLQSIOrnOrn;

SEQ ID NO: 32
HSDAVFTEQY(OMe)TOrnLRAibQLAAbuAibOrnYAibQAibIOrnOrn;

SEQ ID NO: 33
HSDAVFTEQY(OMe)TOrnLRAibQLAAAibOrnYAibQSIOrnOrn;

SEQ ID NO: 34
HSDAVFTEQY(OMe)TOrnLRK(W)QVAAAibOrnYLQSIOrnOrn;

SEQ ID NO: 35
HSDAVFTEQY(OMe)TOrnLRAibQVAAAibOrnYLK(W)SIOrnOrn;

SEQ ID NO: 36
HSDAVFTEQY(OMe)TOrnLRAibQK(W)AAAibOrnYLQSIOrnOrn;

SEQ ID NO: 37
HSDAVFTEQY(OMe)TOrnLRK(CO(CH$_2$)$_2$SH)QVAAAibOrnYLQSIOrnOrn;

SEQ ID NO: 38
HSDAVFTEQY(OMe)TOrnLRAibQVAAAibK(W)YLQSIOrnOrn;

SEQ ID NO: 39
HSDAVFTEQY(OMe)TOrnLRAibQVAAAibCYLQSIOrnOrn;

SEQ ID NO: 40
HSDAVFTEQY(OMe)TOrnLRAibQLAAbuAibOrnYLQAibIOrnOrn;

SEQ ID NO: 41
HSDAVFTEQY(OMe)TOrnLRAibQVAAAibOrnYLQSK(W)OrnOrn;

SEQ ID NO: 42
HSDAVFTEQY(OMe)TOrnLRAibQLAAbuAibOrnYLQAibIOrnCOrn;

SEQ ID NO: 43
HSDAVFTEQY(OMe)TOrnLRAibQLAAbuAibOrnYLQAibCOrnOrn;

SEQ ID NO: 44
HSDAVFTEQY(OMe)TOrnLRAibQCAAbuAibOrnYLQAibIOrnOrn;

SEQ ID NO: 45
HSDAVFTEQY(OMe)TOrnLRCQLAAbuAibOrnYLQAibIOrnOrn;

SEQ ID NO: 94
HSDAVFTEQY(OMe)TOrnLRAibQVK(CO(CH$_2$)$_2$SH)AAibOrnYLQSIOrnOrn;

SEQ ID NO: 95
HSDAVFTEQY(OMe)TOrnLRAibQLAAbuAibOrnYLQSIOrnCOrn;

SEQ ID NO: 96
HSDAVFTEQY(OMe)TOrnLRAibQLAAbuAibOrnYLQSCOrnOrn;

SEQ ID NO: 97
HSDAVFTEQY(OMe)TOrnLRAibQLAAbuAibOrnYLQAibIOrnK(CO(CH$_2$)$_2$SH)Orn;

SEQ ID NO: 98
HSDAVFTEQY(OMe)TOrnLRAibQLAAbuAibOrnYLQSIOrnK(CO(CH$_2$)$_2$SH)Orn;

SEQ ID NO: 99
HSDAVFTEQY(OMe)TOrnLRK(W)QLAAbuAibOrnYLQAibIOrnOrn;

SEQ ID NO: 100
HSDAVFTEQY(OMe)TOrnLRAibQLAAAibOrnYLQSIOrnOrnC;

SEQ ID NO: 101
HSDAVFTEQY(OMe)TOrnLRAibQVAAAibOrnYLQSIOrnOrnC;

SEQ ID NO: 102
HSDAVFTEQY(OMe)TOrnLRAibQLAAbuAibOrnYLQSIOrnOrnC;

SEQ ID NO: 103
HSDAVFTEQY(OMe)TOrnLRAibQLAAbuAibOrnY(OMe)LQAibIOrnOrn;

SEQ ID NO: 104
HSDAVFTEQY(OMe)TOrnLRAibQLAAbuAibOrnY(OMe)LQAibIOrnCOrn;

SEQ ID NO: 105
HSDAVFTEQY(OMe)TOrnLRAibQCAAbuAibOrnY(OMe)LQAibIOrnOrn;

SEQ ID NO: 106
HSDAVFTEQY(OMe)TOrnLRAibQLAAbuAibOrnYLQAibIOrnOrnC;

SEQ ID NO: 107
HSDAVFTEQY(OMe)TOrnLRAibQLAAbuAibOrnY(OMe)LQSIOrnOrn;

SEQ ID NO: 108
HSDAVFTEQY(OMe)TOrnLRAibQCAAbuAibOrnY(OMe)LQSIOrnOrn;

SEQ ID NO: 109
HSDAVFTEQY(OMe)TOrnLRAibQLAAbuAibOrnY(OMe)LQSIOrnCOrn;

SEQ ID NO: 110
HSDAVFTEQY(OMe)TOrnLRAibQLAbuAAibOrnYLQSIOrnOrn;

SEQ ID NO: 111
HSDAVFTEQY(OMe)TOrnLRAibQK(CO(CH$_2$)$_2$SH)AAbuAibOrnYLQAibIOrnOrn;
and SEQ ID NO: 112
HSDAVFTEQY(OMe)TOrnLRAibQK(W)AAbuAibOrnYLQAibIOrnOrn;

and a C-terminal extension wherein the N-terminus of the C-terminal extension is linked to the C-terminus of the peptide sequence and wherein the C-terminal extension comprises and amino acid sequence of the formula:

```
Formula 3
                                          (SEQ ID NO: 3)
Xaa1-Xaa2-Xaa3-Xaa4-Xaa5-Xaa6-Xaa7-Xaa8-Xaa9-

Xaa10-Xaa11-Xaa12
``` wherein:

$Xaa_1$ is: Gly, Cys, or absent;

$Xaa_2$ is: Gly, Arg, or absent;

$Xaa_3$ is: Pro, Thr, or absent;

$Xaa_4$ is: Ser, or absent;

$Xaa_5$ is: Ser, or absent;

$Xaa_6$ is: Gly, or absent;

$Xaa_7$ is: Ala, or absent;

$Xaa_8$ is: Pro, or absent;

$Xaa_9$ is: Pro, or absent;

$Xaa_{10}$ is: Pro, or absent;

$Xaa_{11}$ is: Ser, Cys, or absent; and $Xaa_{12}$ is: Cys, or absent;

wherein at least five of $Xaa_1$ to $Xaa_{12}$ of the C-terminal extension are present, and wherein if $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$, or $Xaa_{11}$ is absent, the next amino acid present downstream is the next amino acid in the C-terminal extension and wherein the C-terminal amino acid may be amidated, and wherein;

the peptide agonist comprises at least one Cys residue which is covalently attached to a PEG molecule, or the peptide agonist comprises at least one Lys residue which is covalently attached to a PEG molecule, or the peptide agonist comprises at least one K(W) which is covalently attached to a PEG molecule, or the peptide agonist comprises at least one K(CO(CH$_2$)$_2$SH) which is covalently attached to a PEG molecule, or the carboxy-terminal amino acid of the peptide agonist is covalently attached to a PEG molecule, or a combination thereof.

Preferably, at least six of $Xaa_1$ to $Xaa_{12}$ of the C-terminal extension of Formula 3 is present. More preferably, at least seven, eight, nine, ten, eleven, or all of $Xaa_1$ to $Xaa_{12}$ of the C-terminal extension are present.

More preferably, the C-terminal extension of the PEGylated VPAC2 receptor peptide agonist is selected from:

| SEQ ID NO: 5  | GGPSSGAPPPS      |
| SEQ ID NO: 6  | GGPSSGAPPPS-NH$_2$ |
| SEQ ID NO: 7  | GGPSSGAPPPC      |
| SEQ ID NO: 8  | GGPSSGAPPPC-NH$_2$ |
| SEQ ID NO: 9  | GRPSSGAPPPS      |
| SEQ ID NO: 10 | GRPSSGAPPPS-NH$_2$ |

-continued

| SEQ ID NO: 11 | GGPSSGAPPPCC      |
| SEQ ID NO: 12 | GGPSSGAPPPCC-NH$_2$ |

Even more preferably, the C-terminal extension of the PEGylated VPAC2 receptor peptide agonist is SEQ ID NO: 11 or SEQ ID NO: 12.

A PEG molecule(s) may be covalently attached to any Lys, Cys, K(W) or K(CO(CH$_2$)$_2$SH) residues at any position in the VPAC2 receptor peptide agonist according to the first aspect of the present invention.

Where the PEGylated VPAC2 receptor peptide agonist comprises a sequence selected from SEQ ID NO: 22, 23, 39, 42, 43, 44, 45, 95, 96, 100, 101, 102, 104, 105, 106, 108 and 109, it is preferred that the cysteine residue is PEGylated.

Where the PEGylated VPAC2 receptor peptide agonist comprises a sequence selected from SEQ ID NO: 19, 34, 35, 36, 38, 41, 99 and 112, it is preferred that the K(W) residue is PEGylated.

Where the PEGylated VPAC2 receptor peptide agonist comprises a sequence selected from SEQ ID NO: 18, 20, 21, 37, 94, 97, 98 and 111, it is preferred that the K(CO(CH$_2$)$_2$SH) residue is PEGylated.

Where the PEGylated VPAC2 receptor peptide agonist comprises a C-terminal extension, the PEG molecule(s) may be covalently attached to one or more Cys residues in said C-terminal extension. Where the sequence selected from SEQ ID NO: 17 to 45 and 94 to 112 comprises one or more Lys, Cys, K(W), or K(CO(CH$_2$)$_2$SH) residues and the C-terminal extension comprises one or more Cys residues, there may be one or more PEGylated residues in either or both sequences.

Preferably, there is at least one PEG molecule covalently attached to a residue in the C-terminal extension of the VPAC2 receptor peptide agonist.

Where there is more than one PEG molecule, there may be a combination of Lys, Cys, K(CO(CH$_2$)$_2$SH), K(W) and carboxy-terminal amino acid PEGylation. For example, if there are two PEG molecules, one may be attached to a Lys residue and one may be attached to a Cys residue.

Preferably, the PEG molecule is branched. Alternatively, the PEG molecule may be linear.

Preferably, the PEG molecule is between 1,000 daltons and 100,000 daltons in molecular weight. More preferably, the PEG molecule is selected from 10,000, 20,000, 30,000, 40,000, 50,000 and 60,000 daltons. Even more preferably, it is selected from 20,000, 30,000, 40,000, or 60,000 daltons. Where there are two PEG molecules covalently attached to the peptide agonist of the present invention, each is 1,000 to 40,000 daltons and preferably, they have molecular weights of 20,000 and 20,000 daltons, 10,000 and 30,000 daltons, 30,000 and 30,000 daltons, or 20,000 and 40,000 daltons.

The PEGylated VPAC2 receptor peptide agonist sequence may further comprise a histidine residue at the N-terminus of the peptide before $Xaa_1$.

Preferably, the PEGylated VPAC2 receptor peptide agonist according to the first aspect of the present invention further comprises a N-terminal modification at the N-terminus of the peptide agonist wherein the N-terminal modification is selected from:

(a) addition of D-histidine, isoleucine, methionine, or norleucine;

(b) addition of a peptide comprising the sequence Ser-Trp-Cys-Glu-Pro-Gly-Trp-Cys-Arg (SEQ ID NO: 93) wherein the Arg is linked to the N-terminus of the peptide agonist;

(c) addition of $C_1$-$C_{16}$ alkyl optionally substituted with one or more substituents independently selected from aryl, $C_1$-$C_6$ alkoxy, —$NH_2$, —OH, halogen and —$CF_3$;

(d) addition of —C(O)$R^1$ wherein $R^1$ is a $C_1$-$C_{16}$ alkyl optionally substituted with one or more substituents independently selected from aryl, $C_1$-$C_6$ alkoxy, —$NH_2$, —OH, halogen, —SH and —$CF_3$; an aryl optionally substituted with one or more substituents independently selected from $C_1$-$C_6$ alkyl, $C_2$-$C_6$ alkenyl, $C_2$-$C_6$ alkynyl, $C_1$-$C_6$ alkoxy, —$NH_2$, —OH, halogen and —$CF_3$; an aryl $C_1$-$C_4$ alkyl optionally substituted with one or more substituents independently selected from $C_1$-$C_6$ alkyl, $C_2$-$C_6$ alkenyl, $C_2$-$C_6$ alkynyl, $C_1$-$C_6$ alkoxy, —$NH_2$, —OH, halogen and —$CF_3$; —$NR^2R^3$ wherein $R^2$ and $R^3$ are independently hydrogen, $C_1$-$C_6$ alkyl, aryl or aryl $C_1$-$C_4$ alkyl; —$OR^4$ wherein $R^4$ is $C_1$-$C_{16}$ alkyl optionally substituted with one or more substituents independently selected from aryl, $C_1$-$C_6$ alkoxy, —$NH_2$, —OH, halogen and —$CF_3$, aryl optionally substituted with one or more substituents independently selected from $C_1$-$C_6$ alkyl, $C_2$-$C_6$ alkenyl, $C_2$-$C_6$ alkynyl, $C_1$-$C_6$ alkoxy, —$NH_2$, —OH, halogen and —$CF_3$, or aryl $C_1$-$C_4$ alkyl optionally substituted with one or more substituents independently selected from $C_1$-$C_6$ alkyl, $C_2$-$C_6$ alkenyl, $C_2$-$C_6$ alkynyl, $C_1$-$C_6$ alkoxy, —$NH_2$, —OH, halogen and —$CF_3$; or 5-pyrrolidin-2-one;

(e) addition of —$SO_2R^5$ wherein $R^5$ is aryl, aryl $C_1$-$C_4$ alkyl or $C_1$-$C_{16}$ alkyl;

(f) formation of a succinimide group optionally substituted with $C_1$-$C_6$ alkyl or —$SR^6$, wherein $R^6$ is hydrogen or $C_1$-$C_6$ alkyl;

(g) addition of methionine sulfoxide;

(h) addition of biotinyl-6-aminohexanoic acid (6-aminocaproic acid); and (i) addition of —C(=NH)—$NH_2$.

Preferably, the N-terminal modification is the addition of a group selected from: acetyl, propionyl, butyryl, pentanoyl, hexanoyl, methionine, methionine sulfoxide, 3-phenylpropionyl, phenylacetyl, benzoyl, norleucine, D-histidine, isoleucine, 3-mercaptopropionyl, biotinyl-6-aminohexanoic acid (6-aminocaproic acid), and —C(=NH)—$NH_2$. It is especially preferred that the N-terminal modification is the addition of acetyl or hexanoyl.

It will be appreciated by the person skilled in the art that PEGylated VPAC2 receptor peptide agonists comprising various combinations of peptide sequence selected from SEQ ID NO: 17 to 45 and 94 to 112, C-terminal extensions and N-terminal modifications as described herein, may be made based on the above disclosure.

It is preferred that the PEGylated VPAC2 receptor peptide agonist according to the first aspect of the present invention comprises an amino acid sequence selected from:

| Agonist # | SEQ ID NO | Sequence |
|---|---|---|
| P410 | 46 | C6-HSDAVFTEQY(OMe)TOrnLRAibQVAAAibK(W-PEG40K)YLQSIOrnOrnGGPSSGAPPPS-$NH_2$ |
| P417 | 47 | C6-HSDAVFTEQY(OMe)TRAibRAibQLAAAibOrnY(OMe)LQSIKAibOrnGGPSSGAPPPC(PEG40K)-$NH_2$ |
| P451 | 48 | C6-HSDAVFTEK(CO(CH$_2$)$_2$SPEG40K)Y(OMe)TOrnLRAibQVAAAibOrnYLQSIOrnOrnGGPSSGAPPPS-$NH_2$ |
| P454 | 49 | C6-HSDAVFTEQY(OMe)TOrnLRAibQVAAAibOrnYLQSIOrnK(WPEG40K)OrnGGPSSGAPPPS-$NH_2$ |
| P460 | 50 | C6-HSDAVFTEQY(OMe)TOrnLRAibQVAAAibC(PEG40K)YLQSIOrnOrnGGPSSGAPPPS-$NH_2$ |
| P472 | 51 | C6-HSDAVFTEQY(OMe)TOrnLRAibQVAAAibK(CO(CH$_2$)$_2$SPEG40K)YLQSIOrnOrnGGPSSGAPPPS-$NH_2$ |
| P473 | 52 | C6-HSDAVFTEQY(OMe)TOrnLRAibQVAAAibK(CO(CH$_2$)$_2$SPEG20K)YLQSIOrnOrnGGPSSGAPPPS-$NH_2$ |
| P475 | 53 | C6-HSDAVFTEQY(OMe)TOrnLRAibQVAAK(CO(CH$_2$)$_2$SPEG40K)OrnYLQSIOrnOrnGGPSSGAPPPS-$NH_2$ |
| P478 | 54 | C6-HSDAVFTEQY(OMe)TOrnLRAibQVC(PEG40K)AAibOrnyLQSIOrnOrnGGPSSGAPPPS-$NH_2$ |
| P483 | 55 | C6-HSDAVFTEQY(OMe)TOrnLRC(PEG40K)QVAAAibOrnYLQSIOrnOrnGGPSSGAPPPS-$NH_2$ |
| P485 | 56 | C6-HSDAVFTEQY(OMe)TOrnLRK(CO(CH$_2$)$_2$SPEG40K)QVAAAibOrnYLQSIOrnOrnGGPSSGAPPPS-$NH_2$ |
| P507 | 57 | C6-HSDAVFTEQY(OMe)TOrnLRAibQVAAAibOrnYAibQSIOrnOrnGGPSSGAPPPC(PEG40K)-$NH_2$ |
| P509 | 58 | C6-HSDAVFTEQY(OMe)TOrnLRAibQVAAAibOrnYLQAibIOrnOrnGGPSSGAPPPC(PEG40K)-$NH_2$ |
| P511 | 59 | C6-HSDAVFTEQY(OMe)TOrnLRAibQVAAbuAibOrnYLQAibIOrnOrnGGPSSGAPPPC(PEG40K)-$NH_2$ |
| P513 | 60 | C6-HSDAVFTEQY(OMe)TOrnLRAibQLAAAibOrnYAibQSIOrnOrnGGPSSGAPPPC(PEG20K)C(PEG20K)-$NH_2$ |
| P515 | 61 | C6-HSDAVFTEQY(OMe)TOrnLRAibQLAAAibOrnYLQAibIOrnOrnGGPSSGAPPPC(PEG20K)C(PEG20K)-$NH_2$ |
| P517 | 62 | C6-HSDAVFTEQY(OMe)TOrnLRAibQLAAbuAibOrnYLQAibIOrnOrnGGPSSGAPPPC(PEG20K)C(PEG20K)-$NH_2$ |
| P519 | 63 | C6-HSDAVFTEQY(OMe)TOrnLRAibQLAAAibOrnYAibQAibIOrnOrnGGPSSGAPPPC(PEG20K)C(PEG20K)-$NH_2$ |
| P521 | 64 | C6-HSDAVFTEQY(OMe)TOrnLRAibQLAAbuAibOrnYAibQSIOrnOrnGGPSSGAPPPC(PEG20K)C(PEG20K)-$NH_2$ |
| P523 | 65 | C6-HSDAVFTEQY(OMe)TOrnLRAibQLAAbuAibOrnYLQSIOrnOrnGGPSSGAPPPC(PEG20K)C(PEG20K)-$NH_2$ |
| P525 | 66 | C6-HSDAVFTEQY(OMe)TOrnLRAibQLAAbuAibOrnYAibQAibIOrnOrnGGPSSGAPPPC(PEG20K)C(PEG20K)-$NH_2$ |
| P529 | 67 | C6-HSDAVFTEQY(OMe)TOrnLRK(WPEG40K)QVAAAibOrnYLQSIOrnOrnGGPSSGAPPPS-$NH_2$ |
| P531 | 68 | C6-HSDAVFTEQY(OMe)TOrnLRAibQVAAAibOrnYLK(WPEG40K)SIOrnOrnGGPSSGAPPPS-$NH_2$ |

-continued

| Agonist # | SEQ ID NO | Sequence |
|---|---|---|
| P533 | 69 | C6-HSDAVFTEQY(OMe)TOrnLRAibQK(WPEG40K)AAAibOrnYLQSIOrnOrnGGPSSGAPPPS-NH₂ |
| P535 | 70 | C6-HSDAVFTEQY(OMe)TOrnLRAibQVAAAibOrnYLQSK(WPEG40K)OrnOrnGGPSSGAPPPS-NH₂ |
| P537 | 71 | C6-HSDAVFTEQY(OMe)TOrnLRAibQLAAbuAibOrnYLQAibIOrnC(PEG40K)OrnGGPSSGAPPPS-NH₂ |
| P541 | 72 | C6-HSDAVFTEQY(OMe)TOrnLRAibQLAAbuAibOrnYLQAibC(PEG40K)OrnOrnGGPSSGAPPPS-NH₂ |
| P545 | 73 | C6-HSDAVFTEQY(OMe)TOrnLRAibQC(PEG40K)AAbuAibOrnYLQAibIOrnOrnGGPSSGAPPPS-NH₂ |
| P547 | 74 | C6-HSDAVFTEQY(OMe)TOrnLRC(PEG40K)QLAAbuAibOrnYLQAibIOrnOrnGGPSSGAPPPS-NH₂ |
| P480 | 113 | C6-HSDAVFTEQY(OMe)TOrnLRAibQVK(CO(CH₂)₂SPEG40K)AAibOrnYLQSIOrnOrnGGPSSGAPPPS-NH₂ |
| P481 | 114 | C6-HSDAVFTEQY(OMe)TOrnLRAibQVK(CO(CH₂)₂SPEG20K)AAibOrnYLQSIOrnOrnGGPSSGAPPPS-NH₂ |
| P539 | 115 | C6-HSDAVFTEQY(OMe)TOrnLRAibQLAAbuAibOrnYLQSIOrnC(PEG40K)OrnGGPSSGAPPPS-NH₂ |
| P543 | 116 | C6-HSDAVFTEQY(OMe)TOrnLRAibQLAAbuAibOrnYLQSC(PEG40K)OrnOrnGGPSSGAPPPS-NH₂ |
| P549 | 117 | C6-HSDAVFTEQY(OMe)TOrnLRAibQLAAbuAibOrnYLQAibIOrnK(CO(CH₂)₂SPEG20K)OrnGGPSSGAPPPC(PEG20K)-NH₂ |
| P551 | 118 | C6-HSDAYFTEQY(OMe)TOrnLRAibQLAAbuAibOrnYLQSIOrnK(CO(CH₂)₂SPEG20K)OrnGGPSSGAPPPC(PEG20K)-NH₂ |
| P555 | 119 | C6-HSDAVFTEQY(OMe)TOrnLRAibQLAAbuAibOrnYLQSIOrnC(PEG20K)OrnGGPSSGAPPPC(PEG20K)-NH₂ |
| P557 | 120 | C6-HSDAVFTEQY(OMe)TOrnLRK(WPEG40K)QLAAbuAibOrnYLQAibIOrnOrnGGPSSGAPPPS-NH₂ |
| P560 | 121 | C6-HSDAVFTEQY(OMe)TOrnLRAibQLAAAibOrnYLQSIOrnOrnC(PEG40K)GGPSSGAPPPS-NH₂ |
| P562 | 122 | C6-HSDAVFTEQY(OMe)TOrnLRAibQVAAAibOrnYLQSIOrnOrnC(PEG20K)GGPSSGAPPPC(PEG20K)NH₂ |
| P564 | 123 | C6-HSDAVFTEQY(OMe)TOrnLRAibQLAAbuAibOrnYLQAIbIOrnOrnC(PEG40K)GGPSSGAPPPS-NH₂ |
| P566 | 124 | C6-HSDAVFTEQY(OMe)TOrnLRAibQLAAbuAibOrnYLQSIOrnOrnC(PEG40K)GGPSSGAPPPS-NH₂ |
| P572 | 125 | C6-HSDAVFTEQY(OMe)TOrnLRAibQLAAbuAibOrnYLQSIOrnOrnC(PEG20K)GGPSSGAPPPC(PEG20K)-NH₂ |
| P574 | 126 | C6-HSDAVFTEQY(OMe)TOrnLRAibQLAAbuAibOrnY(OMe)LQAibIOrnOrnGGPSSGAPPPC(PEG20K)C(PEG20K)-NH₂ |
| P576 | 127 | C6-HSDAVFTEQY(OMe)TOrnLRAibQLAAbUAibOrnY(OMe)LQAibIOrnC(PEG40K)OrnGGPSSGAPPPS-NH₂ |
| P578 | 128 | C6-HSDAVFTEQY(OMe)TOrnLRAibQC(PEG40K)AAbuAibOrnY(OMe)LQAibIOrnOrnGGPSSGAPPPS-NH₂ |
| P580 | 129 | C6-HSDAVFTEQY(OMe)TOrnLRAibQLAAbuAibOrnYLQAibIOrnOrnC(PEG20K)GGPSSGAPPPC(PEG20K)-NH₂ |
| P582 | 130 | C6-HSDAVFTEQY(OMe)TOrnLRAibQLAAbuAibOrnY(OMe)LQSIOrnOrnGGPSSGAPPPC(PEG20K)C(PEG20K)-NH₂ |
| P584 | 131 | C6-HSDAVFTEQY(OMe)TOrnLRAibQLAAbuAibOrnY(OMe)LQSIOrnC(PEG40K)OrnGGPSSGAPPPS-NH₂ |
| P586 | 132 | C6-HSDAVFTEQY(OMe)TOrnLRAibQC(PEG40K)AAbuAibOrnY(OMe)LQSIOrnOrnGGPSSGAPPPS-NH₂ |
| P588 | 133 | C6-HSDAVFTEQY(OMe)TOrnLRAibQLAAbuAibOrnY(OMe)LQSIOrnC(PEG20K)OrnGGPSSGAPPPC(PEG20K)-NH₂ |
| P590 | 134 | C6-HSDAVFTEQY(OMe)TOrnLRAibQLAbuAAibOrnYLQSIOrnOrnGGPSSGAPPPC(PEG20K)C(PEG20K)-NH₂ |
| P597 | 135 | C6-HSDAVFTEQY(OMe)TOrnLRAibQK(CO(CH₂)₂SPEG20K)AAbuAibOrnYLQAibIOrnOrnGGPSSGAPPPC(PEG20K)-NH₂ |
| P599 | 136 | C6-HSDAVFTEQY(OMe)TOrnLRAibQK(CO(CH₂)₂SPEG40K)AAbuAibOrnYLQAibIOrnOrnGGPSSGAPPPS-NH₂ |
| P601 | 137 | C6-HSDAVFTEQY(OMe)TOrnLRAibQK(WPEG40K)AAbuAibOrnYLQAibIOrnOrnGGPSSGAPPPS-NH₂ |
| P469 | 139 | C6-HSDAVFTEK(CO(CH₂)₂SPEG20K)Y(OMe)TOrnLRAibQVAAAibOrnYLQSIOrnOrnGGPSSGAPPPS-NH₂ |
| P486 | 140 | C6-HSDAVFTEQY(OMe)TOrnLRK(CO(CH₂)₂SPEG20K)QVAAAibOrnYLQSIOrnOrnGGPSSGAPPPS-NH₂ |
| P553 | 141 | C6-HSDAVFTEQY(OMe)TOrnLRAibQLAAbuAibOrnYLQAibIOrnC(PEG20K)OrnGGPSSGAPPPC(PEG20K)-NH₂ |
| P570 | 144 | C6-HSDAVFTEQY(OMe)TOrnLRAibQLAAbuAibOrnyLQAibIOrnOrnGGPSSGAPPPC(PEG30K)C(PEG30K)-NH₂ |
| P595 | 146 | C6-HSDAVFTEQY(OMe)TOrnLRAibQC(PEG20K)AAbuAibOrnYLQAibIOrnOrnGGPSSGAPPPC(PEG20K)-NH₂ |
| P476 | 147 | C6-HSDAVFTEQY(OMe)TOrnLRAibQVAAK(CO(CH₂)₂SPEG20K)OrnYLQSIOrnOrnGGPSSGAPPPS-NH₂ |
| P602 | 148 | C6-HSDAVFTEQY(OMe)TOrnLRAibQLAAbuAibOrnyAibQSIOrnOrnGGPSSGAPPPC(PEG30K)C(PEG30K)-NH₂ |

It is more preferred that the PEGylated VPAC2 receptor peptide agonist according to the first aspect of the present invention comprises an amino acid sequence selected from: SEQ ID NO: 47, 64, 66, 115, 119, 122, 126, 130 and 144.

According to a second aspect of the present invention, there is provided a PEGylated VPAC2 receptor peptide agonist comprising an amino acid sequence selected from:

| Agonist # | SEQ ID NO | Sequence |
| --- | --- | --- |
| P470 | 75 | C6-HSDAVFTEQY(OMe)TOrnK(CO(CH$_2$)$_2$SPEG 20K)RAibQVAAAibOrnYLQSIOrnOrnGGPSSGAP PPS-NH$_2$ |
| P490 | 76 | C6-HSDAVFTEQY(OMe)TOrnLRAibQVAAAibOrn YLK(CO(CH$_2$)$_2$SPEG20K)SIOrnOrnGGPSSGAPP PC(PEG20K)-NH$_2$ |
| P492 | 77 | C6-HSDAVFTEQY(OMe)TOrnLRAibQVAK(CO (CH$_2$)$_2$SPEG20K)AibOrnYLQSIOrnOrnGGPSSG APPPC(PEG20K)-NH$_2$ |
| P495 | 78 | C6-HSDAVFTEQY(OMe)TOrnLRAibQVAAAibOrn YLQK(CO(CH$_2$)$_2$SPEG20K)IOrnOrnGGPSSGAPP PC(PEG20K)-NH$_2$ |
| P497 | 79 | C6-HSDAVFTEQY(OMe)TOrnLRAibQVAAAibOrn YLQSK(CO(CH$_2$)$_2$SPEG20K)OrnOrnGGPSSGAPP PC(PEG20K)-NH$_2$ |
| P499 | 80 | C6-HSDAVFTEQY(OMe)TOrnLRAibQVAAAibOrn YLQSIOrnK(CO(CH$_2$)$_2$SPEG20K)OrnGGPSSGAP PPC(PEG20K)-NH$_2$ |
| P501 | 81 | C6-HSDAVFTEQY(OMe)TOrnLRAibQVAAAibOrn YLC(PEG20K)SIOrnOrnGGPSSGAPPPC(PEG 20K)-NH$_2$ |
| P503 | 82 | C6-HSDAVFTEQY(OMe)TOrnLRAibQVAAAibOrn YLQSC(PEG20K)OrnOrnGGPSSGAPPPC(PEG 20K)-NH$_2$ |
| P505 | 83 | C6-HSDAVFTEQY(OMe)TOrnLRAibQVAAAibOrn YLQSIOrnC(PEG20K)OrnGGPSSGAPPPC(PEG 20K)-NH$_2$ |
| P402 | 138 | C6-HSDAVFTEQY(OMe)TOrnLRAibQVAAAibOrn YLQSIOrnOrnGGPSSGAPPPK(W-PEG40K)-NH$_2$ |
| P558 | 142 | C6-HSDAVFTEQY(OMe)TOrnLRAibQC(PEG20K) AAAibOrnYLQSIOrnOrnGGPSSGAPPPS-NH$_2$ |
| P568 | 143 | C6-HSDAVFTEQY(OMe)TOrnLRAibQC(PEG20K) AAAibOrnYLQSIOrnOrnGGPSSGAPPPC(PEG 20K)-NH$_2$ |
| P593 | 145 | C6-HSDAVFTEQY(OMe)TOrnLRAibQLAAbuAib OrnYAibQAibIOrnOrnGGPSSGAPPPK(WPEG 40K)-NH$_2$ |

It is more preferred that the PEGylated VPAC2 receptor peptide agonist according to the second aspect of the present invention comprises the amino acid sequence SEQ ID NO: 80 or SEQ ID NO: 83.

According to a third aspect of the present invention, there is provided a PEGylated VPAC2 receptor peptide agonist comprising an amino acid sequence of the formula:

Formula 4
(SEQ ID NO: 4)
Xaa$_1$-Xaa$_2$-Xaa$_3$-Xaa$_4$-Xaa$_5$-Xaa$_6$-Thr-Xaa$_8$-Xaa$_9$-

Xaa$_{10}$-Thr-Xaa$_{12}$-Xaa$_{13}$-Xaa$_{14}$-Xaa$_{15}$-Xaa$_{16}$-Xaa$_{17}$-

Xaa$_{18}$-Abu-Xaa$_{20}$-Xaa$_{21}$-Xaa$_{22}$-Xaa$_{23}$-Xaa$_{24}$-Xaa$_{25}$-

Xaa$_{26}$-Xaa$_{27}$-Xaa$_{28}$-Xaa$_{29}$-Xaa$_{30}$-Xaa$_{31}$-Xaa$_{32}$-

Xaa$_{33}$-Xaa$_{34}$-Xaa$_{35}$-Xaa$_{36}$-Xaa$_{37}$-Xaa$_{38}$-Xaa$_{39}$-

Xaa$_{40}$ wherein:

Xaa$_1$ is: His, dH, or is absent;

Xaa$_2$ is: dA, Ser, Val, Gly, Thr, Leu, dS, Pro, or Aib;

Xaa$_3$ is: Asp or Glu;

Xaa$_4$ is: Ala, Ile, Tyr, Phe, Val, Thr, Leu, Trp, Gly, dA, Aib, or NMeA;

Xaa$_5$ is: Val, Leu, Phe, Ile, Thr, Trp, Tyr, dV, Aib, or NMeV;

Xaa$_6$ is: Phe, Ile, Leu, Thr, Val, Trp, or Tyr;

Xaa$_8$ is: Asp, Glu, Ala, Lys, Leu, Arg, or Tyr;

Xaa$_9$ is: Asn, Gln, Asp, Glu, Ser, Cys, Lys, or K(CO(CH$_2$)$_2$SH);

Xaa$_{10}$ is: Tyr, Trp, Tyr(OMe), Ser, Cys, or Lys;

Xaa$_{12}$ is: Arg, Lys, Glu, hR, Orn, Lys (isopropyl), Aib, Cit, Ala, Leu, Gln, Phe, Ser, or Cys;

Xaa$_{13}$ is: Leu, Phe, Glu, Ala, Aib, Ser, Cys, Lys, or K(CO(CH$_2$)$_2$SH);

Xaa$_{14}$ is: Arg, Leu, Lys, Ala, hR, Orn, Lys (isopropyl), Phe, Gln, Aib, Cit, Ser, or Cys;

Xaa$_{15}$ is: Lys, Ala, Arg, Glu, Leu, hR, Orn, Lys (isopropyl), Phe, Gln, Aib, K(Ac), Cit, Ser, Cys, K(W), or K(CO(CH$_2$)$_2$SH);

Xaa$_{16}$ is: Gln, Lys, Glu, Ala, hR, Orn, Lys (isopropyl), Cit, Ser, Cys, K(CO(CH$_2$)$_2$SH), or K(W);

Xaa$_{17}$ is: Val, Ala, Leu, Ile, Met, Nle, Lys, Aib, Ser, Cys, K(CO(CH$_2$)$_2$SH), or K(W);

Xaa$_{18}$ is: Ala, Ser, Cys, Lys, K(CO(CH$_2$)$_2$SH), K(W), Abu, or Nle;

Xaa$_{20}$ is: Lys, Gln, hR, Arg, Ser, His, Orn, Lys (isopropyl), Ala, Aib, Trp, Thr, Leu, Ile, Phe, Tyr, Val, K(Ac), Cit, Cys, K(CO(CH$_2$)$_2$SH), or K(W);

Xaa$_{21}$ is: Lys, His, Arg, Ala, Phe, Aib, Leu, Gln, Orn, hR, K(Ac), Cit, Ser, Cys, Val, Tyr, Ile, Thr, Trp, K(W), or K(CO(CH$_2$)$_2$SH);

Xaa$_{22}$ is: Tyr, Trp, Phe, Thr, Leu, Ile, Val, Tyr(OMe), Ala, Aib, Ser, Cys, Lys, K(W), or K(CO(CH$_2$)$_2$SH);

Xaa$_{23}$ is: Leu, Phe, Ile, Ala, Trp, Thr, Val, Aib, Ser, Cys, Lys, K(W), or K(CO(CH$_2$)$_2$SH);

Xaa$_{24}$ is: Gln, Glu, Asn, Ser, Cys, Lys, K(CO(CH$_2$)$_2$SH), or K(W);

Xaa$_{25}$ is: Ser, Asp, Phe, Ile, Leu, Thr, Val, Trp, Gln, Asn, Tyr, Aib, Glu, Cys, Lys, K(CO(CH$_2$)$_2$SH), or K(W);

Xaa$_{26}$ is: Ile, Leu, Thr, Val, Tip, Tyr, Phe, Aib, Ser, Cys, Lys, K(CO(CH$_2$)$_2$SH), or K(W);

Xaa$_{27}$ is: Lys, hR, Arg, Gln, Ala, Asp, Glu, Phe, Gly, His, Ile, Met, Asn, Pro, Ser, Thr, Val, Trp, Tyr, Lys (isopropyl), Cys, Leu, Orn, dK, K(W), or K(CO(CH$_2$)$_2$SH);

Xaa$_{28}$ is: Asn, Asp, Gln, Lys, Arg, Aib, Orn, hR, Cit, Pro, dK, Ser, Cys, K(CO(CH$_2$)$_2$SH), or K(W);

Xaa$_{29}$ is: Lys, Ser, Arg, Asn, hR, Ala, Asp, Glu, Phe, Gly, His, Ile, Leu, Met, Pro, Gln, Thr, Val, Trp, Tyr, Cys, Orn, Cit, Aib, K(W), K(CO(CH$_2$)$_2$SH), or is absent;

Xaa$_{30}$ is: Arg, Lys, Ile, Ala, Asp, Glu, Phe, Gly, His, Leu, Met, Asn, Pro, Gln, Ser, Thr, Val, Trp, Tyr, Cys, hR, Cit, Aib, Orn, K(W), K(CO(CH$_2$)$_2$SH), or is absent;

Xaa$_{31}$ is: Tyr, His, Phe, Thr, Cys, Ser, Lys, Gln, K(W), K(CO(CH$_2$)$_2$SH), or is absent;

Xaa$_{32}$ is: Ser, Cys, Lys, or is absent;

Xaa$_{33}$ is: Trp or is absent;

Xaa$_{34}$ is: Cys or is absent;

Xaa$_{35}$ is: Glu or is absent;

Xaa$_{36}$ is: Pro or is absent;

Xaa$_{37}$ is: Gly or is absent;

Xaa$_{38}$ is: Trp or is absent;

Xaa$_{39}$ is: Cys or is absent; and

Xaa$_{40}$ is: Arg or is absent wherein if Xaa$_{29}$, Xaa$_{30}$, Xaa$_{31}$, Xaa$_{32}$, Xaa$_{33}$, Xaa$_{34}$, Xaa$_{35}$, Xaa$_{36}$, Xaa$_{37}$, Xaa$_{38}$, or Xaa$_{39}$ is absent, the next amino acid present downstream is the next amino acid in the peptide agonist sequence, and a C-terminal extension wherein the N-terminus of the C-terminal extension is linked to the C-terminus of the peptide of Formula 4 and wherein the C-terminal extension comprises an amino acid sequence of the formula:

```
Formula 3
                                          (SEQ ID NO: 3)
Xaa1-Xaa2-Xaa3-Xaa4-Xaa5-Xaa6-Xaa7-Xaa8-Xaa9-

Xaa10-Xaa11-Xaa12
``` wherein:

Xaa$_1$ is: Gly, Cys, or absent;

Xaa$_2$ is: Gly, Arg, or absent;

Xaa$_3$ is: Pro, Thr, or absent;

Xaa$_4$ is: Ser, or absent;

Xaa$_5$ is: Ser, or absent;

Xaa$_6$ is: Gly, or absent;

Xaa$_7$ is: Ala, or absent;

Xaa$_8$ is: Pro, or absent;

Xaa$_9$ is: Pro, or absent;

Xaa$_{10}$ is: Pro, or absent;

Xaa$_{11}$ is: Ser, Cys, or absent; and

Xaa$_{12}$ is: Cys, or absent;

wherein at least five of Xaa$_1$ to Xaa$_{12}$ of the C-terminal extension are present and wherein if Xaa$_1$, Xaa$_2$, Xaa$_3$, Xaa$_4$, Xaa$_5$, Xaa$_6$, Xaa$_7$, Xaa$_8$, Xaa$_9$, Xaa$_{10}$, or Xaa$_{11}$ is absent, the next amino acid present downstream is the next amino acid in the C-terminal extension and wherein the C-terminal amino acid may be amidated, and wherein;

the peptide agonist comprises at least one Cys residue which is covalently attached to a PEG molecule, or the peptide agonist comprises at least one Lys residue which is covalently attached to a PEG molecule, or the peptide agonist comprises at least one K(W) which is covalently attached to a PEG molecule, or the peptide agonist comprises at least one K(CO(CH$_2$)$_2$SH) which is covalently attached to a PEG molecule, or the carboxy-terminal amino acid of the peptide agonist is covalently attached to a PEG molecule, or a combination thereof.

Preferably, the PEGylated VPAC2 receptor peptide agonist of the third aspect of the present invention comprises a sequence of the Formula 4 (SEQ ID NO: 4) wherein Xaa$_3$ is Asp or Glu, Xaa$_8$ is Asp or Glu, Xaa$_9$ is Asn or Gln, Xaa$_{10}$ is Tyr or Tyr(OMe), Xaa$_{12}$ is Arg, hR, Lys, or Orn, Xaa$_{14}$ is Arg, Gln, Aib, hR, Orn, Cit, Lys, Ala, or Leu, Xaa$_{15}$ is Lys, Aib, Orn, or Arg, Xaa$_{16}$ is Gln or Lys, Xaa$_{17}$ is Val, Leu, Ala, Ile, Lys, or Nle, Xaa$_{20}$ is Lys, Val, Leu, Aib, Ala, Gln, or Arg, Xaa$_{21}$ is Lys, Aib, Orn, Ala, Gln, or Arg, Xaa$_{23}$ is Leu or Aib, Xaa$_{25}$ is Ser or Aib, Xaa$_{27}$ is Lys, Orn, hR, or Arg, Xaa$_{28}$ is Asn, Gln, Lys, hR, Aib, Orn, or Pro and Xaa$_{29}$ is Lys, Orn, hR, or is absent.

Preferably, the PEGylated VPAC2 receptor peptide agonist of the third aspect of the present invention comprises a sequence of the Formula 4 (SEQ ID NO: 4), wherein either Xaa$_{23}$ or Xaa$_{25}$ is Aib. Even more preferably, Xaa$_{23}$ and Xaa$_{25}$ are both Aib.

Preferably, the PEGylated VPAC2 receptor peptide agonist of the third aspect of the present invention comprises a sequence of the Formula 4 wherein either Xaa$_{14}$ or Xaa$_{15}$ is Aib.

Alternatively, the PEGylated VPAC2 receptor peptide agonist of the third aspect of the present invention comprises a sequence of the Formula 4 wherein either Xaa$_{20}$ or Xaa$_{21}$ is Aib.

More preferably, either Xaa$_{14}$ or Xaa$_{15}$ is Aib and either Xaa$_{20}$ or Xaa$_{21}$ is Aib. It is especially preferred that Xaa$_{15}$ is Aib and Xaa$_{20}$ is Aib.

Preferably, the PEGylated VPAC2 receptor peptide agonist of the third aspect of the present invention comprises a sequence of the Formula 4 wherein Xaa$_{15}$ is Aib, Xaa$_{20}$ is Aib, and Xaa$_{12}$, Xaa$_{21}$, Xaa$_{27}$ and Xaa$_{28}$ are all Orn. More preferably, Xaa$_{15}$ is Aib, Xaa$_{20}$ is Aib, Xaa$_{12}$, Xaa$_{21}$, Xaa$_{27}$ and Xaa$_{28}$ are all Orn, Xaa$_8$ is Glu, Xaa$_9$ is Gln and Xaa$_{10}$ is Tyr(OMe). Even more preferably, Xaa$_{15}$ is Aib, Xaa$_{20}$ is Aib, Xaa$_{12}$, Xaa$_{21}$, Xaa$_{27}$ and Xaa$_{28}$ are all Orn, Xaa$_8$ is Glu, Xaa$_9$ is Gln, Xaa$_{10}$ is Tyr(OMe), and Xaa$_{23}$ and/or Xaa$_{25}$ is Aib. Any one or more of Xaa$_8$, Xaa$_9$, Xaa$_{10}$, Xaa$_{12}$, Xaa$_{15}$, Xaa$_{20}$, Xaa$_{21}$, Xaa$_{23}$, Xaa$_{25}$, Xaa$_{27}$ and Xaa$_{28}$ may be a PEGylated Lys, Cys, K(CO(CH$_2$)$_2$SH) or K(W), whilst all the other positions have the preferred amino acid substitutions as described.

Preferably, at least six of Xaa$_1$ to Xaa$_{12}$ of the C-terminal extension of Formula 3 is present. More preferably, seven, eight, nine, ten, eleven, or all of Xaa$_1$ to Xaa$_{12}$ of the C-terminal extension are present.

Preferably, the C-terminal extension of the PEGyated VPAC2 receptor peptide agonist according to the third aspect of the present invention is selected from: SEQ ID NO: 5, 6, 7, 8, 9, 10, 11 and 12.

More preferably, the C-terminal extension of the PEGyated VPAC2 receptor peptide agonist according to the third aspect of the present invention is SEQ ID NO: 11 or SEQ ID NO: 12.

A PEG molecule(s) may be covalently attached to any Lys, Cys, K(W) or K(CO(CH$_2$)$_2$SH) residue at any position in the VPAC2 receptor peptide agonist according to the third aspect of the present invention. The C-terminal extension may comprise one or more Cys residues which may be PEGylated. Where the sequence according to Formula 4 comprises one or more Lys, Cys, K(W), or K(CO(CH$_2$)$_2$SH) residues and the C-terminal extension comprises one or more Cys residues, there may be one or more PEGylated residues in either or both sequences.

Preferably, there is at least one PEG molecule covalently attached to a residue in Formula 4. More preferably, there is a PEG molecule covalently attached to a residue at one or more of the following positions of Formula 4: 9, 13, 15, 16, 17, 18, 20, 21, 24, 25, 26 and 28.

Preferably, there is at least one PEG molecule covalently attached to a residue in the C-terminal extension of the VPAC2 receptor peptide agonist.

Where there is more than one PEG molecule, there may be a combination of Lys, Cys, K(CO(CH$_2$)$_2$SH), K(W) and carboxy-terminal amino acid PEGylation. For example, if there are two PEG molecules, one may be attached to a Lys residue and one may be attached to a Cys residue.

Preferably, the PEG molecule is branched. Alternatively, the PEG molecule may be linear.

Preferably, the PEG molecule is between 1,000 daltons and 100,000 daltons in molecular weight. More preferably, the PEG molecule is selected from 10,000, 20,000, 30,000, 40,000, 50,000 and 60,000 daltons. Even more preferably, it is selected from 20,000, 30,000, 40,000, or 60,000 daltons. Where there are two PEG molecules covalently attached to the peptide agonist of the present invention, each is 1,000 to 40,000 daltons and preferably, they have molecular weights of 20,000 and 20,000 daltons, 10,000 and 30,000 daltons, 30,000 and 30,000 daltons, or 20,000 and 40,000 daltons.

Preferably, the PEGylated VPAC2 receptor peptide agonist of the third aspect of the present invention further comprises a N-terminal modification at the N-terminus of the peptide agonist wherein the N-terminal modification is selected from:

(a) addition of D-histidine, isoleucine, methionine, or norleucine;
(b) addition of a peptide comprising the sequence Ser-Trp-Cys-Glu-Pro-Gly-Trp-Cys-Arg (SEQ ID NO: 93) wherein the Arg is linked to the N-terminus of the peptide agonist;
(c) addition of C$_1$-C$_{16}$ alkyl optionally substituted with one or more substituents independently selected from aryl, C$_1$-C$_6$ alkoxy, —NH$_2$, —OH, halogen and —CF$_3$;
(d) addition of —C(O)R$^1$ wherein R$^1$ is a C$_1$-C$_{16}$ alkyl optionally substituted with one or more substituents independently selected from aryl, C$_1$-C$_6$ alkoxy, —NH$_2$, —OH, halogen, —SH and —CF$_3$; an aryl optionally substituted with one or more substituents independently selected from C$_1$-C$_6$ alkyl, C$_2$-C$_6$ alkenyl, C$_2$-C$_6$ alkynyl, C$_1$-C$_6$ alkoxy, —NH$_2$, —OH, halogen and —CF$_3$; and aryl C$_1$-C$_4$ alkyl optionally substituted with one or more substituents independently selected from C$_1$-C$_6$ alkyl, C$_2$-C$_6$ alkenyl, C$_2$-C$_6$ alkynyl, C$_1$-C$_6$ alkoxy, —NH$_2$, —OH, halogen and —CF$_3$; —NR$^2$R$^3$ wherein R$^2$ and R$^3$ are independently hydrogen, C$_1$-C$_6$ alkyl, aryl or aryl C$_1$-C$_4$ alkyl; —OR$^4$ wherein R$^4$ is C$_1$-C$_{16}$ alkyl optionally substituted with one or more substituents independently selected from aryl, C$_1$-C$_6$ alkoxy, —NH$_2$, —OH, halogen and —CF$_3$, aryl optionally substituted with one or more substituents independently selected from C$_1$-C$_6$ alkyl, C$_2$-C$_6$ alkenyl, C$_2$-C$_6$ alkynyl, C$_1$-C$_6$ alkoxy, —NH$_2$, —OH, halogen and —CF$_3$ or aryl C$_1$-C$_4$ alkyl optionally substituted with one or more substituents independently selected from C$_1$-C$_6$ alkyl, C$_2$-C$_6$ alkenyl, C$_2$-C$_6$ alkynyl, C$_1$-C$_6$ alkoxy, —NH$_2$, —OH, halogen and —CF$_3$; or 5-pyrrolidin-2-one;
(e) addition of —SO$_2$R$^5$ wherein R$^5$ is aryl, aryl C$_1$-C$_4$ alkyl or C$_1$-C$_{16}$ alkyl;
(f) formation of a succinimide group optionally substituted with C$_1$-C$_6$ alkyl or —SR$^6$ wherein R$^6$ is hydrogen or C$_1$-C$_6$ alkyl;
(g) addition of methionine sulfoxide;
(h) addition of biotinyl-6-aminohexanoic acid (6-aminocaproic acid); and
(i) addition of —C(=NH)—NH$_2$.

Preferably, the N-terminal modification is the addition of a group selected from: acetyl, propionyl, butyryl, pentanoyl, hexanoyl, methionine, methionine sulfoxide, 3-phenylpropionyl, phenylacetyl, benzoyl, norleucine, D-histidine, isoleucine, 3-mercaptopropionyl, biotinyl-6-aminohexanoic acid (6-aminocaproic acid), and —C(=NH)—NH$_2$. It is especially preferred that the N-terminal modification is the addition of acetyl or hexanoyl.

It will be appreciated by the person skilled in the art that PEGylated VPAC2 receptor peptide agonists comprising various combinations of peptide sequence according to Formula 4, C-terminal extensions and N-terminal modifications as described herein, may be made based on the above disclosure.

It is preferred that the PEGylated VPAC2 receptor peptide agonist according to the third aspect of the present invention comprises an amino acid sequence selected from: SEQ ID NO: 59, 62, 64, 65, 66, 71, 72, 73, 74, 115, 116, 117, 118, 119, 120, 123, 124, 125, 126, 127, 128, 129, 130, 131, 132, 133, 135, 136, 137, 141, 144, 146 and 148.

According to a fourth aspect of the present invention, there is provided a pharmaceutical composition comprising a PEGylated VPAC2 receptor peptide agonist of the present invention and one or more pharmaceutically acceptable diluents, carriers and/or excipients.

According to a fifth aspect of the present invention, there is provided a PEGylated VPAC2 receptor peptide agonist of the present invention for use as a medicament.

According to a sixth aspect of the present invention, there is provided the use of a PEGylated VPAC2 receptor peptide agonist of the present invention for the manufacture of a medicament for the treatment non-insulin-dependent diabetes.

According to a further aspect of the present invention, there is provided the use of a PEGylated VPAC2 receptor peptide agonist of the present invention for the manufacture of a medicament for the treatment insulin-dependent diabetes.

The present invention provides a method of treating diabetes in a patient in need thereof comprising administering a PEGylated VPAC2 receptor peptide agonist of the present invention, wherein the diabetes may be non-insulin dependent diabetes or may be insulin-dependent diabetes.

The present invention further provides a pharmaceutical composition containing a PEGylated VPAC2 receptor peptide agonist of the present invention for treating non-insulin dependent diabetes or insulin-dependent diabetes.

According to an alternative embodiment of the present invention, there is provided a PEGylated VPAC2 receptor peptide agonist comprising a sequence selected from SEQ ID NO: 17 to 45 and 94 to 112;

and a C-terminal extension wherein the N-terminus of the C-terminal extension is linked to the C-terminus of the peptide sequence and wherein the C-terminal extension comprises an amino acid sequence of the formula:

Formula 1
(SEQ ID NO: 1)
Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$ wherein:

Xaa$_1$ is: Gly, Cys, Lys, K(W), K(CO(CH$_2$)$_2$SH), or absent;

Xaa$_2$ is: Gly, Arg, Cys, Lys, K(W), K(CO(CH$_2$)$_2$SH), or absent;

Xaa$_3$ is: Pro, Thr, Ser, Ala, Cys, Lys, K(W), K(CO(CH$_2$)$_2$SH), or absent;

Xaa$_4$ is: Ser, Pro, His, Cys, Lys, K(W), K(CO(CH$_2$)$_2$SH), or absent;

Xaa$_5$ is: Ser, Arg, Thr, Trp, Lys, Cys, K(W), K(CO(CH$_2$)$_2$SH), or absent;

Xaa$_6$ is: Gly, Ser, Cys, Lys, K(W), K(CO(CH$_2$)$_2$SH), or absent;

Xaa$_7$ is: Ala, Asp, Arg, Glu, Lys, Gly, Cys, K(W), K(CO(CH$_2$)$_2$SH), or absent;

Xaa$_8$ is: Pro, Ser, Ala, Cys, Lys, K(W), K(CO(CH$_2$)$_2$SH), or absent;

Xaa$_9$ is: Pro, Ser, Ala, Cys, Lys, K(W), K(CO(CH$_2$)$_2$SH), or absent;

Xaa$_{10}$ is: Pro, Ser, Ala, Arg, Lys, His, Cys, K(W), K(CO(CH$_2$)$_2$SH), or absent;

Xaa$_{11}$ is: Ser, Cys, His, Pro, Lys, Arg, K(W), K(CO(CH$_2$)$_2$SH), or absent;

Xaa$_{12}$ is: His, Ser, Arg, Lys, Cys, K(W), K(CO(CH$_2$)$_2$SH), or absent; and Xaa$_{13}$ is: His, Ser, Arg, Lys, Cys, K(W), K(CO(CH$_2$)$_2$SH), or absent;

provided that if Xaa$_1$, Xaa$_2$, Xaa$_3$, Xaa$_4$, Xaa$_5$, Xaa$_6$, Xaa$_7$, Xaa$_8$, Xaa$_9$, Xaa$_{10}$, Xaa$_{11}$, or Xaa$_{12}$ is absent, the next amino acid present downstream is the next amino acid in the C-terminal extension and wherein the C-terminal amino acid may be amidated, and wherein;

the peptide agonist comprises at least one Cys residue which is covalently attached to a PEG molecule, or the peptide agonist comprises at least one Lys residue which is covalently attached to a PEG molecule, or the peptide agonist comprises at least one K(W) which is covalently attached to a PEG molecule, or the peptide agonist comprises at least one K(CO(CH$_2$)$_2$SH) which is covalently attached to a PEG molecule, or the carboxy-terminal amino acid of the peptide agonist is covalently attached to a PEG molecule, or a combination thereof.

It is preferable that the C-terminal extension of Formula 1 has no more than three of any one of the following; Cys, Lys, K(W) or K(CO(CH$_2$)$_2$SH). It is more preferable that the C-terminal extension has no more than two of any of these residues. If there are two Cys residues in the C-terminal extension, it is preferred that the Cys residues are at the C-terminus. It is even more preferable that the C-terminal extension has no more than one of any of these residues. If there is only one Cys residue in the C-terminal extension, it is preferred that the Cys residue is at the C-terminus.

Preferably, the C-terminal extension of the PEGylated VPAC2 receptor peptide agonist according to the above alternative embodiment comprises an amino acid sequence of the formula:

Formula 2
(SEQ ID NO: 2)
Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$ wherein:

Xaa$_1$ is: Gly, Cys, Lys, or absent;

Xaa$_2$ is: Gly, Arg, Cys, Lys, or absent;

Xaa$_3$ is: Pro, Thr, Ser, Ala, Cys, Lys, or absent;

Xaa$_4$ is: Ser, Pro, His, Cys, Lys, or absent;

Xaa$_5$ is: Ser, Arg, Thr, Trp, Lys, Cys, or absent;

Xaa$_6$ is: Gly, Ser, Cys, Lys, or absent;

Xaa$_7$ is: Ala, Asp, Arg, Glu, Lys, Gly, Cys, or absent;

Xaa$_8$ is: Pro, Ser, Ala, Cys, Lys, or absent;

Xaa$_9$ is: Pro, Ser, Ala, Cys, Lys, or absent;

Xaa$_{10}$ is: Pro, Ser, Ala, Arg, Lys, His, Cys, or absent;

Xaa$_{11}$ is: Ser, Cys, His, Pro, Lys, Arg, or absent;

Xaa$_{12}$ is: His, Ser, Arg, Lys, Cys, or absent; and

Xaa$_{13}$ is: His, Ser, Arg, Lys, Cys, or absent;

provided that if Xaa$_1$, Xaa$_2$, Xaa$_3$, Xaa$_4$, Xaa$_5$, Xaa$_6$, Xaa$_7$, Xaa$_8$, Xaa$_9$, Xaa$_{10}$, Xaa$_{11}$, or Xaa$_{12}$ is absent, the next amino acid present downstream is the next amino acid in the C-terminal extension and wherein the C-terminal amino acid may be amidated.

Preferably, at least one of Xaa$_1$ to Xaa$_{13}$ of the C-terminal extension of Formula 1 or 2 is present. More preferably, at least two, three, four, five, six, seven, eight, nine, ten, eleven, twelve, or all of Xaa$_1$ to Xaa$_{13}$ of the C-terminal extension are present.

More preferably, the C-terminal extension of the PEGylated VPAC2 receptor peptide agonist according to the above alternative embodiment comprises an amino acid sequence of the formula:

Formula 3
(SEQ ID NO: 3)
Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$ wherein:

Xaa$_1$ is: Gly, Cys, or absent;

Xaa$_2$ is: Gly, Arg, or absent;

Xaa$_3$ is: Pro, Thr, or absent;

Xaa$_4$ is: Ser, or absent;

Xaa$_5$ is: Ser, or absent;

Xaa$_6$ is: Gly, or absent;

Xaa$_7$ is: Ala, or absent;

Xaa$_8$ is: Pro, or absent;

Xaa$_9$ is: Pro, or absent;

Xaa$_{10}$ is: Pro, or absent;

Xaa$_{11}$ is: Ser, Cys, or absent; and

Xaa$_{12}$ is: Cys, or absent;

provided that if Xaa$_1$, Xaa$_2$, Xaa$_3$, Xaa$_4$, Xaa$_5$, Xaa$_6$, Xaa$_7$, Xaa$_8$, Xaa$_9$, Xaa$_{10}$, or Xaa$_{11}$ is absent, the next amino acid present downstream is the next amino acid in the C-terminal extension and wherein the C-terminal amino acid may be amidated.

Preferably, at least one of Xaa$_1$ to Xaa$_{12}$ of the C-terminal extension of Formula 3 is present. More preferably, at least two, three, four, five, six, seven, eight, nine, ten, eleven, or all of Xaa$_1$ to Xaa$_{12}$ of the C-terminal extension are present.

An alternative C-terminal extension, which may be used in any of the aspects and embodiments of the present invention, comprises an amino acid sequence of the formula:

Formula 13
(SEQ ID NO: 13)
Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$ wherein:

Xaa$_1$ is: Ser, Cys, Lys, K(W), K(CO(CH$_2$)$_2$SH), or absent;

Xaa$_2$ is: Arg, Ser, hR, Orn, His, Cys, Lys, K(W), K(CO(CH$_2$)$_2$SH), or absent, Xaa$_3$ is: Thr, Cys, Lys, K(W), K(CO(CH$_2$)$_2$SH), or absent;

Xaa$_4$ is: Ser, Cys, Lys, K(W), K(CO(CH$_2$)$_2$SH), or absent;

Xaa$_5$ is: Pro, Ser, Ala, Cys, Lys, K(W), K(CO(CH$_2$)$_2$SH), or absent;

Xaa$_6$ is: Pro, Ser, Ala, Arg, Cys, Lys, K(W), K(CO(CH$_2$)$_2$SH), or absent;

Xaa$_7$ is: Pro, Ser, Ala, Cys, Lys, K(W), K(CO(CH$_2$)$_2$SH), or absent;

Xaa$_8$ is: Lys, K(W), Pro, Cys, K(CO(CH$_2$)$_2$SH), or absent;

Xaa$_9$ is: K(E-C$_{16}$), Ser, Cys, Lys, K(W), K(CO(CH$_2$)$_2$SH), or absent; and Xaa$_{10}$ is: Ser, Cys, Lys, K(W), K(CO(CH$_2$)$_2$SH), or absent.

It is preferred that if Xaa$_1$, Xaa$_2$, Xaa$_3$, Xaa$_4$, Xaa$_5$, Xaa$_6$, Xaa$_7$, Xaa$_8$ or Xaa$_9$ of Formula 13 is absent, the next amino acid downstream is the next amino acid in the C-terminal extension. The C-terminal amino acid may be amidated.

Preferably, at least one of Xaa$_1$ to Xaa$_{10}$ of the C-terminal extension of Formula 13 is present. More preferably, at least two, three, four, five, six, seven, eight, nine or all of Xaa$_1$ to Xaa$_{10}$ of the C-terminal extension are present.

More preferably, an alternative C-terminal extension, which may be used in any of the aspects and embodiments of the present invention, is selected from:

| | |
|---|---|
| SEQ ID NO: 85 | SRTSPPP |
| SEQ ID NO: 86 | SRTSPPP-NH$_2$ |
| SEQ ID NO: 87 | SSTSPRPPSS |
| SEQ ID NO: 88 | SSTSPRPPSS-NH$_2$ |
| SEQ ID NO: 89 | SRTSPPPK(W) |
| SEQ ID NO: 90 | SRTSPPPK(W)-NH$_2$ |
| SEQ ID NO: 91 | SRTSPPPC |
| SEQ ID NO: 92 | SRTSPPPC-NH$_2$ |

The VPAC2 receptor peptide agonists of the present invention have the advantage that they have enhanced selectivity, potency and/or stability over known VPAC2 receptor peptide agonists. In particular, the addition of the C-terminal sequence of Exendin-4, or a variant of this C-terminal sequence, as the c-capping sequence surprisingly increased the VPAC2 receptor selectivity as well as increasing proteolytic stability.

The covalent attachment of one or more molecules of PEG to particular residues of a VPAC2 receptor peptide agonist results in a biologically active, PEGylated VPAC2 receptor peptide agonist with an extended half-life and reduced clearance when compared to that of non-PEGylated VPAC2 receptor peptide agonists.

The term "VPAC2" is used to refer to and in conjunction with the particular receptor (Lutz, et al., *FEBS Lett.*, 458: 197-203 (1999); Adamou, et al., *Biochem. Biophys. Res. Commun.*, 209: 385-392 (1995)) that the agonists of the present invention activate. This term also is used to refer to and in conjunction with the agonists of the present invention.

A "selective VPAC2 receptor peptide agonist" or a "VPAC2 receptor peptide agonist" of the present invention is a peptide that selectively activates the VPAC2 receptor to induce insulin secretion. Preferably, the sequence for a selective VPAC2 receptor peptide agonist of the present invention has twenty-eight to forty naturally occurring and/or non-naturally occurring amino acids and may or may not additionally comprise a C-terminal extension.

A "selective PEGylated VPAC2 receptor peptide agonist" or a "PEGylated VPAC2 receptor peptide agonist" is a selective VPAC2 receptor peptide agonist covalently attached to one or more molecules of polyethylene glycol (PEG), or a derivative thereof, wherein each PEG is attached to a cysteine or lysine amino acid, to a K(W) or K(CO(CH$_2$)$_2$SH), or to the carboxy terminus of a peptide.

Selective PEGylated VPAC2 receptor peptide agonists may have a C-terminal extension. The "C-terminal extension" of the present invention comprises a sequence having from one to thirteen naturally occurring or non-naturally occurring amino acids linked to the C-terminus of the sequence at the N-terminus of the C-terminal extension via a peptide bond. Any Cys, Lys, K(W), or K(CO(CH$_2$)$_2$SH) residues in the C-terminal extension may be covalently attached to a PEG molecule, and/or the carboxy-terminal amino acid of the C-terminal extension may be covalently attached to a PEG molecule.

As used herein, the term "linked to" with reference to the term C-terminal extension, includes the addition or attachment of amino acids or chemical groups directly to the C-terminus of the peptide sequence.

Optionally, the selective PEGylated VPAC2 receptor peptide agonist may also have an N-terminal modification. The term "N-terminal modification" as used herein includes the addition or attachment of amino acids or chemical groups directly to the N-terminus of a peptide and the formation of chemical groups, which incorporate the nitrogen at the N-terminus of a peptide.

The N-terminal modification may comprise the addition of one or more naturally occurring or non-naturally occurring amino acids to the VPAC2 receptor peptide agonist sequence, preferably there are not more than ten amino acids, with one amino acid being more preferred. Naturally occurring amino acids which may be added to the N-terminus include methionine and isoleucine. A modified amino acid added to the N-terminus may be D-histidine. Alternatively, the following amino acids may be added to the N-terminus: SEQ ID NO: 93 Ser-Trp-Cys-Glu-Pro-Gly-Trp-Cys-Arg, wherein the Arg is linked to the N-terminus of the peptide agonist. Preferably, any amino acids added to the N-terminus are linked to the N-terminus by a peptide bond.

The term "linked to" as used herein, with reference to the term N-terminal modification, includes the addition or attachment of amino acids or chemical groups directly to the N-terminus of the VPAC2 receptor agonist. The addition of the above N-terminal modifications may be achieved under normal coupling conditions for peptide bond formation.

The N-terminus of the peptide agonist may also be modified by the addition of an alkyl group (R), preferably a $C_1$-$C_{16}$ alkyl group, to form (R)NH—.

Alternatively, the N-terminus of the peptide agonist may be modified by the addition of a group of the formula —C(O)$R^1$ to form an amide of the formula $R^1$C(O)NH—. The addition of a group of the formula —C(O)$R^1$ may be achieved by reaction with an organic acid of the formula $R^1$COOH. Modification of the N-terminus of an amino acid sequence using acylation is demonstrated in the art (e.g. Gozes et al., *J. Pharmacol Exp Ther*, 273:161-167 (1995)). Addition of a group of the formula —C(O)$R^1$ may result in the formation of a urea group (see WO 01/23240, WO 2004/06839) or a carbamate group at the N-terminus. Also, the N-terminus may be modified by the addition of pyroglutamic acid, or 6-aminohexanoic acid.

The N-terminus of the peptide agonist may be modified by the addition of a group of the formula —$SO_2R^5$, to form a sulfonamide group at the N-terminus.

The N-terminus of the peptide agonist may also be modified by reacting with succinic anhydride to form a succinimide group at the N-terminus. The succinimide group incorporates the nitrogen at the N-terminus of the peptide.

The N-terminus may alternatively be modified by the addition of methionine sulfoxide, biotinyl-6-aminohexanoic acid, or —C(=NH)—$NH_2$. The addition of —C(=NH)—$NH_2$ is a guanidation modification, where the terminal $NH_2$ of the N-terminal amino acid becomes —NH—C(=NH)—$NH_2$.

Most of the sequences of the present invention, including the N-terminal modifications and the C-terminal extensions contain the standard single letter or three letter codes for the twenty naturally occurring amino acids. The other codes used are defined as follows:
C6=hexanoyl
d=the D isoform (nonnaturally occurring) of the respective amino acid,
  e.g., dA=D-alanine, dS=D-serine, dK=D-lysine
hR=homoarginine
Aib=amino isobutyric acid
OMe=methoxy
Nle=Nor-leucine
NMe=N-methyl attached to the alpha amino group of an amino acid,
  e.g., NMeA=N-methyl alanine, NMeV=N-methyl valine
Orn=ornithine
K(CO(CH$_2$)$_2$SH)=ε-(3'-mercaptopropionyl)-lysine
K(W)=ε-(L-tryptophyl)-lysine
Abu=α-amino-n-butyric acid or 2-aminobutanoic acid
Cit=citrulline
K(Ac)=ε-acetyl lysine
PEG=polyethylene glycol
PEG40K=40,000 Dalton PEG molecule
PEG30K=30,000 Dalton PEG molecule
PEG20K=20,000 Dalton PEG molecule VIP naturally occurs as a single sequence having 28 amino acids. However, PACAP exists as either a 38 amino acid peptide (PACAP-38) or as a 27 amino acid peptide (PACAP-27) with an amidated carboxyl (Miyata, et al., *Biochem Biophys Res Commun*, 170:643-648 (1990)). The sequences for VIP, PACAP-27, and PACAP-38 are as follows:

| Peptide | Seq.ID # | Sequence |
|---|---|---|
| VIP | SEQ ID NO: 14 | HSDAVFTDNYTRLRKQMAVKKYLNSILN |
| PACAP-27 | SEQ ID NO: 15 | HSDGIFTDSYSRYRKQMAVKKYLAAVL-NH$_2$ |
| PACAP-38 | SEQ ID NO: 16 | HSDGIFTDSYSRYRKQMAVKKYLAAVLGKRYQRVKNK-NH$_2$ |

The term "naturally occurring amino acid" as used herein means the twenty amino acids coded for by the human genetic code (i.e. the twenty standard amino acids). These twenty amino acids are: Alanine, Arginine, Asparagine, Aspartic Acid, Cysteine, Glutamine, Glutamic Acid, Glycine, Histidine, Isoleucine, Leucine, Lysine, Methionine, Phenylalanine, Proline, Serine, Threonine, Tryptophan, Tyrosine and Valine.

Examples of "non-naturally occurring amino acids" include both synthetic amino acids and those modified by the body. These include D-amino acids, arginine-like amino acids (e.g., homoarginine), and other amino acids having an extra methylene in the side chain ("homo" amino acids), and modified amino acids (e.g norleucine, lysine (isopropyl)—wherein the side chain amine of lysine is modified by an isopropyl group). Also included are amino acids such as ornithine, amino isobutyric acid and 2-aminobutanoic acid.

"Selective" as used herein refers to a VPAC2 receptor peptide agonist with increased selectivity for the VPAC2 receptor compared to other known receptors. The degree of selectivity is determined by a ratio of VPAC2 receptor binding affinity to VPAC1 receptor binding affinity or by a ratio of VPAC2 receptor binding affinity to PAC1 receptor binding affinity. Binding affinity is determined as described below in Example 4.

"Insulinotropic activity" refers to the ability to stimulate insulin secretion in response to elevated glucose levels, thereby causing glucose uptake by cells and decreased plasma glucose levels. Insulinotropic activity can be assessed by methods known in the art, including using experiments that measure VPAC2 receptor binding activity or receptor activation (e.g. insulin secretion by insulinoma cell lines or islets, intravenous glucose tolerance test (IVGTT), intraperitoneal glucose tolerance test (IPGTT), and oral glucose tolerance test (OGTT)). Insulinotropic activity is routinely measured in humans by measuring insulin levels or C-peptide levels. Selective PEGylated VPAC2 receptor peptide agonists of the present invention have insulinotropic activity.

"In vitro potency" as used herein is the measure of the ability of a peptide to activate the VPAC2 receptor in a cell-based assay. In vitro potency is expressed as the "$EC_{50}$" which is the effective concentration of compound that results in a 50% of maximum increase in activity in a single dose-response experiment. For the purposes of the present invention, in vitro potency is determined using two different assays: DiscoveRx and Alpha Screen. See Examples 3 and 5 for further details of these assays. Whilst these assays are performed in different ways, the results demonstrate a general correlation between the two assays.

The term "plasma half-life" refers to the time in which half of the relevant molecules circulate in the plasma prior to being cleared. An alternatively used term is "elimination half-life." The term "extended" or "longer" used in the context of plasma half-life or elimination half-life indicates there is a statistically significant increase in the half-life of a PEGylated VPAC2 receptor peptide agonist relative to that of the reference molecule (e.g., the non-PEGylated form of the peptide or the native peptide) as determined under comparable conditions. The half-life reported herein is the elimination half-life; it is that which corresponds to the terminal log-linear rate of elimination. The person skilled in the art appreciates that half-life is a derived parameter that changes as a function of both clearance and volume of distribution.

Clearance is the measure of the body's ability to eliminate a drug. As clearance decreases due, for example, to modifications to a drug, half-life would be expected to increase. However, this reciprocal relationship is exact only when there is no change in the volume of distribution. A useful approximate relationship between the terminal log-linear half-life ($t_{1/2}$), clearance (C), and volume of distribution (V) is given by the equation: $t_{1/2} \approx 0.693$ (V/C). Clearance does not indicate how much drug is being removed but, rather, the volume of biological fluid such as blood or plasma that would have to be completely freed of drug to account for the elimination. Clearance is expressed as a volume per unit of time.

"Percent (%) sequence identity" as used herein is used to denote sequences which when aligned have similar (identical or conservatively replaced) amino acids in like positions or regions, where identical or conservatively replaced amino acids are those which do not alter the activity or function of the protein as compared to the starting protein. For example, two amino acid sequences with at least 85% identity to each other have at least 85% similar (identical or conservatively replaced residues) in a like position when aligned optimally allowing for up to 3 gaps, with the proviso that in respect of the gaps a total of not more than 15 amino acid residues is affected.

The reference peptide used for the percentage sequence identity calculations herein is:

```
P487        C6-HSDAVFTEQY(OMe)TOrnLRAibQLAAAibOrn
SEQ ID NO: 84 YLQSIOrnOrnGGPSSGAPPPS-NH2
```

Percent sequence identity may be calculated by determining the number of residues that differ between a peptide encompassed by the present invention and a reference peptide such as P487 (SEQ ID NO: 84), taking that number and dividing it by the number of amino acids in the reference peptide (e.g. 39 amino acids for P487), multiplying the result by 100, and subtracting that resulting number from 100. For example, a sequence having 39 amino acids with four amino acids that are different from P487 would have a percent (%) sequence identity of 90% (e.g. 100–((4/39)×100)). For a sequence that is longer than 39 amino acids, the number of residues that differ from the P487 sequence will include the additional amino acids over 39 for purposes of the aforementioned calculation. For example, a sequence having 40 amino acids, with four amino acids different from the 39 amino acids in the P487 sequence and with one additional amino acid at the carboxy terminus which is not present in the P487 sequence, would have a total of five amino acids that differ from P487. Thus, this sequence would have a percent (%) sequence identity of 87% (e.g. 100–((5/39)×100)). The degree of sequence identity may be determined using methods well known in the art (see, for example, Wilbur, W. J. and Lipman, D. J., *Proc. Natl. Acad. Sci. USA* 80:726-730 (1983) and Myers E. and Miller W., *Comput. Appl. Biosci.* 4:11-17 (1988)). One program which may be used in determining the degree of similarity is the MegAlign Lipman-Pearson one pair method (using default parameters) which can be obtained from DNAstar Inc, 1128, Selfpark Street, Madison, Wis., 53715, USA as part of the Lasergene system. Another program, which may be used, is Clustal W. This is a multiple sequence alignment package developed by Thompson et al (*Nucleic Acids Research,* 22(22):4673-4680 (1994)) for DNA or protein sequences. This tool is useful for performing cross-species comparisons of related sequences and viewing sequence conservation. Clustal W is a general purpose multiple sequence alignment program for DNA or proteins. It produces biologically meaningful multiple sequence alignments of divergent sequences. It calculates the best match for the selected sequences, and lines them up so that the identities, similarities and differences can be seen. Evolutionary relationships can be seen via viewing Cladograms or Phylograms.

The sequence for a selective PEGylated VPAC2 receptor peptide agonist of the present invention is selective for the VPAC2 receptor and preferably has a sequence identity in the range of 60% to 70%, 60% to 65%, 65% to 70%, 70% to 80%, 70% to 75%, 75% to 80%, 80% to 90%, 80% to 85%, 85% to 90%, 90% to 97%, 90% to 95%, or 95% to 97%, with P487 (SEQ ID NO: 84). Preferably, the sequence has a sequence identity of greater than 82% with P487 (SEQ ID NO: 84). More preferably, the sequence has greater than 90% sequence identity with P487 (SEQ ID NO: 84). Even more preferably, the sequence has greater than 92% sequence identity with P487 (SEQ ID NO: 84). Yet more preferably, the sequence has greater than 95% sequence identity or 97% sequence identity with P487 (SEQ ID NO: 84).

The term "$C_1$-$C_{16}$ alkyl" as used herein means a monovalent saturated straight, branched or cyclic chain hydrocarbon radical having from 1 to 16 carbon atoms or when cyclic, having from 3 to 16 carbon atoms. Thus the term "$C_1$-$C_{16}$ alkyl" includes, for example, methyl, ethyl, n-propyl, isopropyl, n-butyl, isobutyl, sec-butyl, tert-butyl, n-heptyl, n-octyl, cyclopropyl, cyclobutyl, cyclopentyl and cyclohexyl. The $C_1$-$C_{16}$ alkyl group may be optionally substituted with one or more substituents including, for example, aryl, $C_1$-$C_6$alkoxy, —OH, halogen, —$CF_3$ and —SH.

The term "$C_1$-$C_6$ alkyl" as used herein means a monovalent saturated straight, branched or cyclic chain hydrocarbon radical having from 1 to 6 carbon atoms or when cyclic, having from 3 to 6 carbon atoms. Thus the term "$C_1$-$C_6$ alkyl" includes, for example, methyl, ethyl, n-propyl, isopropyl, n-butyl, isobutyl, sec-butyl, tert-butyl, cyclopropyl, cyclobutyl, cyclopentyl and cyclohexyl. The $C_1$-$C_6$ alkyl group may be optionally substituted with one or more substituents.

The term "$C_2$-$C_6$ alkenyl" as used herein means a monovalent straight, branched or cyclic chain hydrocarbon radical having at least one double bond and having from 2 to 6 carbon atoms or when cyclic, having form 3 to 6 carbon atoms. Thus the term "$C_2$-$C_6$ alkenyl" includes vinyl, prop-2-enyl, but-3-enyl, pent-4-enyl and isopropenyl. The $C_2$-$C_6$ alkenyl group may be optionally substituted with one or more substituents.

The term "$C_2$-$C_6$ alkynyl" as used herein means a monovalent straight or branched chain hydrocarbon radical having at least one triple bond and having from 2 to 6 carbon atoms.

Thus the term "$C_2$-$C_6$ alkynyl" includes prop-2-ynyl, but-3-ynyl and pent-4-ynyl. The $C_2$-$C_6$ alkynyl may be optionally substituted with one or more substituents.

The term "$C_1$-$C_6$ alkoxy" as used herein means a monovalent unsubstituted saturated straight-chain or branched-chain hydrocarbon radical having from 1 to 6 carbon atoms linked to the point of substitution by a divalent O radical. Thus the term "$C_1$-$C_6$ alkoxy" includes, for example, methoxy, ethoxy, n-propoxy, isopropoxy, n-butoxy, isobutoxy, sec-butoxy and tert-butoxy. The $C_1$-$C_6$ alkoxy group may be optionally substituted with one or more substituents.

The term "halo" or "halogen" means fluorine, chlorine, bromine or iodine.

The term "aryl" when used alone or as part of a group is a 5 to 10 membered aromatic or heteroaromatic group including a phenyl group, a 5 or 6-membered monocyclic heteroaromatic group, each member of which may be optionally substituted with 1, 2, 3, 4 or 5 substituents (depending upon the number of available substitution positions), a naphthyl group or an 8-, 9- or 10-membered bicyclic heteroaromatic group, each member of which may be optionally substituted with 1, 2, 3, 4, 5 or 6 substituents (depending on the number of available substitution positions). Within this definition of aryl, suitable substitutions include $C_1$-$C_6$ alkyl, $C_2$-$C_6$ alkenyl, $C_2$-$C_6$ alkynyl, —$NH_2$, —OH, halogen, —SH and $CF_3$.

The term "aryl $C_1$-$C_4$ alkyl" as used herein means a $C_1$-$C_4$ alkyl group substituted with an aryl. Thus the term "aryl $C_1$-$C_4$ alkyl" includes benzyl, 1-phenylethyl (α-methylbenzyl), 2-phenylethyl, 1-naphthalenemethyl or 2-naphthalenemethyl.

The term "naphthyl" includes 1-naphthyl, and 2-naphthyl. 1-naphthyl is preferred.

The term "benzyl" as used herein means a monovalent unsubstituted phenyl radical linked to the point of substitution by a —$CH_2$— group.

The term "5- or 6-membered monocyclic heteroaromatic group" as used herein means a monocyclic aromatic group with a total of 5 or 6 atoms in the ring wherein from 1 to 4 of those atoms are each independently selected from N, O and S. Preferred groups have 1 or 2 atoms in the ring which are each independently selected from N, O and S. Examples of 5-membered monocyclic heteroaromatic groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Examples of 6-membered monocyclic heteroaromatic groups include pyridinyl, pyrimidyl, pyrazinyl, pyridazinyl and triazinyl.

The term "8-, 9- or 10-membered bicyclic heteroaromatic group" as used herein means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaromatic groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaromatic groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl and imidazo[1,2-a]pyridine. Suitable 10-membered bicyclic heteroaromatic groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

The term "PEG" as used herein means a polyethylene glycol molecule. In its typical form, PEG is a linear polymer with terminal hydroxyl groups and has the formula HO—$CH_2CH_2$—($CH_2CH_2O$)n—$CH_2CH_2$—OH, where n is from about 8 to about 4000. The terminal hydrogen may be substituted with a protective group such as an alkyl or alkanol group. Preferably, PEG has at least one hydroxy group, more preferably it is a terminal hydroxy group. It is this hydroxy group which is preferably activated to react with the peptide. There are many forms of PEG useful for the present invention. Numerous derivatives of PEG exist in the art and are suitable for use in the invention. (See, e.g., U.S. Pat. Nos. 5,445,090; 5,900,461; 5,932,462; 6,436,386; 6,448,369; 6,437,025; 6,448,369; 6,495,659; 6,515,100 and 6,514,491 and Zalipsky, S. *Bioconjugate Chem.* 6:150-165, 1995). The PEG molecule covalently attached to VPAC2 receptor peptide agonists in the present invention is not intended to be limited to a particular type. The molecular weight of the PEG molecule is preferably from 500-100,000 daltons. PEG may be linear or branched. PEGylated VPAC2 receptor peptide agonists of the invention may have one, two or three PEG molecules attached to the peptide. It is more preferable that there be one or two PEG molecules per PEGylated VPAC2 receptor peptide agonist, however, when there is more than one PEG molecule per peptide molecule, it is preferred that there be no more than three. It is further contemplated that both ends of the PEG molecule may be homo- or heterofunctionalized for crosslinking two or more VPAC2 receptor peptide agonists together. Where there are two PEG molecules present, the PEG molecules will preferably each be 20,000 dalton PEG molecules or each be 30,000 dalton PEG molecules. However, PEG molecules having a different molecular weight may be used, for example, one 10,000 dalton PEG molecule and one 30,000 PEG molecule, or one 20,000 dalton PEG molecule and one 40,000 dalton PEG molecule.

In the present invention, a PEG molecule may be covalently attached to a Cys or Lys residue or to the C-terminal residue. The PEG molecule may also be covalently attached to a Trp residue which is coupled to the side chain of a Lys residue (K(W)). Alternatively, a K(CO($CH_2$)$_2$SH) group may be PEGylated to form K(CO($CH_2$)$_2$S-PEG). Any Lys residue in the peptide agonist may be substituted for a K(W) or K(CO($CH_2$)$_2$SH), which may then be PEGylated. In addition, any Cys residue in the peptide agonist may be substituted for a modified cysteine residue, for example, hC. The modified Cys residue may be covalently attached to a PEG molecule.

The term "PEGylation" as used herein means the covalent attachment of one or more PEG molecules as described above to the VPAC2 receptor peptide agonists of the present invention.

According to a preferred embodiment of the present invention, there is provided a PEGylated VPAC2 receptor peptide agonist comprising a peptide sequence selected from: SEQ ID NO: 17 to 45 and 94 to 112, and a C-terminal extension selected from: SEQ ID NO: 5, 6, 7, 8, 9, 10, 11 and 12. It is especially preferred that the C-terminal extension is SEQ ID NO: 11 or SEQ ID NO: 12.

According to a more preferred embodiment of the present invention, there is provided a PEGylated VPAC2 receptor peptide agonist comprising a peptide sequence selected from: SEQ ID NO: 17 to 45 and 94 to 112, and a C-terminal extension selected from: SEQ ID NO: 5, 6, 7, 8, 9, 10, 11 and 12, and wherein the VPAC2 receptor peptide agonist further comprises a N-terminal modification, which modification is the addition of acetyl, propionyl, butyryl, pentanoyl, hexanoyl, methionine, methionine sulfoxide, 3-phenylpropionyl, phenylacetyl, benzoyl, norleucine, D-histidine, isoleucine, 3-mercaptopropionyl, biotinyl-6-aminohexanoic acid (6-aminocaproic acid), and —C(=NH)—NH$_2$. In this embodiment, it is more preferred that the N-terminal modification is the addition of acetyl or hexanoyl.

According to a further preferred embodiment of the present invention, there is provided a PEGylated VPAC2 receptor peptide agonist comprising an amino acid sequence of Formula 4 (SEQ ID NO: 4) and a C-terminal extension selected from: SEQ ID NO: 5, 6, 7, 8, 9, 10, 11 and 12, and wherein the PEGylated VPAC2 receptor peptide agonist further comprises a N-terminal modification, which modification is the addition of acetyl, propionyl, butyryl, pentanoyl, hexanoyl, methionine, methionine sulfoxide, 3-phenylpropionyl, phenylacetyl, benzoyl, norleucine, D-histidine, isoleucine, 3-mercaptopropionyl, biotinyl-6-aminohexanoic acid (6-aminocaproic acid), and —C(=NH)—NH$_2$. In this embodiment, it is more preferred that the N-terminal modification is the addition of acetyl or hexanoyl.

According to a more preferred embodiment of the present invention, there is provided a PEGylated VPAC2 receptor peptide agonist comprising an amino acid sequence of Formula 4 (SEQ ID NO: 4), wherein Xaa$_{15}$ is Aib, Xaa$_{20}$ is Aib, and Xaa$_{12}$, Xaa$_{21}$, Xaa$_{27}$ and Xaa$_{28}$ are all Orn, and a C-terminal extension selected from: SEQ ID NO: 5, 6, 7, 8, 9, 10, 11 and 12, and wherein the PEGylated VPAC2 receptor peptide agonist further comprises a N-terminal modification, which modification is the addition of acetyl, propionyl, butyryl, pentanoyl, hexanoyl, methionine, methionine sulfoxide, 3-phenylpropionyl, phenylacetyl, benzoyl, norleucine, D-histidine, isoleucine, 3-mercaptopropionyl, biotinyl-6-aminohexanoic acid (6-aminocaproic acid), and —C(=NH)—NH$_2$. In this embodiment, it is more preferred that Xaa$_{15}$ is Aib, Xaa$_{20}$ is Aib, Xaa$_{12}$, Xaa$_{21}$, Xaa$_{27}$ and Xaa$_{28}$ are all Orn, Xaa$_8$ is Glu, Xaa$_9$ is Gln, and Xaa$_{10}$ is Tyr(OMe). It is especially preferred that Xaa$_{15}$ is Aib, Xaa$_{20}$ is Aib, Xaa$_{12}$, Xaa$_{21}$, Xaa$_{27}$ and Xaa$_{28}$ are all Orn, Xaa$_8$ is Glu, Xaa$_9$ is Gln, Xaa$_{10}$ is Tyr(OMe), and Xaa$_{23}$ and/or Xaa$_{25}$ is Aib PEGylation of proteins may overcome many of the pharmacological and toxicological/immunological problems associated with using peptides or proteins as therapeutics. However, for any individual peptide it is uncertain whether the PEGylated form of the peptide will have significant loss in bioactivity as compared to the unPEGylated form of the peptide.

The bioactivity of PEGylated proteins can be affected by factors such as: i) the size of the PEG molecule; ii) the particular sites of attachment; iii) the degree of modification; iv) adverse coupling conditions; v) whether a linker is used for attachment or whether the polymer is directly attached; vi) generation of harmful co-products; vii) damage inflicted by the activated polymer; or viii) retention of charge. Work performed on the PEGylation of cytokines, for example, shows the effect PEGylation may have. Depending on the coupling reaction used, polymer modification of cytokines has resulted in dramatic reductions in bioactivity [Francis, G. E., et al., (1998) PEGylation of cytokines and other therapeutic proteins and peptides: the importance of biological optimization of coupling techniques, *Intl. J. Hem.* 68:1-18]. Maintaining the bioactivity of PEGylated peptides is even more problematic than for proteins. As peptides are smaller than proteins, modification by PEGylation may potentially have a greater effect on bioactivity.

The VPAC2 receptor peptide agonists of the present invention are modified by the covalent attachment of one or more molecules of a PEG and generally have improved pharmacokinetic profiles due to slower proteolytic degradation and renal clearance. PEGylation will increase the apparent size of the VPAC2 receptor peptide agonists, thus reducing renal filtration and altering biodistribution. PEGylation can shield antigenic epitopes of the VPAC2 receptor peptide agonists, thus reducing reticuloendothelial clearance and recognition by the immune system and also reducing degradation by proteolytic enzymes, such as DPP-IV.

Covalent attachment of one or more molecules of PEG to a small, biologically active VPAC2 receptor peptide agonist poses the risk of adversely affecting the agonist, for example, by destabilising the inherent secondary structure and bioactive conformation and reducing bioactivity, so as to make the agonist unsuitable for use as a therapeutic. The present invention, however, is based on the finding that covalent attachment of one or more molecules of PEG to particular residues of a VPAC2 receptor peptide agonist surprisingly results in a biologically active, PEGylated VPAC2 receptor peptide agonist with an extended half-life and reduced clearance when compared to that of non-PEGylated VPAC2 receptor peptide agonists. The compounds of the present invention include selective PEGylated VPAC2 receptor peptide agonists.

In order to determine the potential PEGylation sites in a VPAC2 receptor peptide agonist, serine scanning may be conducted. A Ser residue is substituted at a particular position in the peptide and the Ser-modified peptide is tested for potency and selectivity. If the Ser substitution has minimal impact on potency and the Ser-modified peptide is selective for the VPAC2 receptor, the Ser residue is then substituted for a Cys or Lys residue, which serves as a direct or indirect PEGylation site. Indirect PEGylation of a residue is the PEGylation of a chemical group or residue which is bonded to the PEGylation site residue. Indirect PEGylation of Lys includes PEGylation of K(W) and K(CO(CH$_2$)$_2$SH).

The invention described herein provides PEGylated VPAC2 receptor peptide agonists. PEGylation can enhance the half-life of the selective VPAC2 receptor peptide agonists, resulting in PEGylated VPAC2 receptor peptide agonists with an elimination half-life of at least one hour, preferably at least 3, 5, 7, 10, 15, 20, or 24 hours and most preferably at least 48 hours. The PEGylated VPAC2 receptor peptide agonists of the present invention preferably have a clearance value of 200 ml/h/kg or less, more preferably 180, 150, 120, 100, 80, 60 ml/h/kg or less and most preferably less than 50, 40 or 20 ml/h/kg.

The present invention encompasses the discovery that specific amino acids added to the C-terminus of a peptide sequence for a VPAC2 receptor peptide agonist may protect the peptide as well as may enhance activity, selectivity, and/or potency. For example, these C-terminal extensions may stabilize the helical structure of the peptide and stabilize sites located near to the C-terminus, which are prone to enzymatic cleavage. Furthermore, many of the C-terminally extended peptides disclosed herein may be more selective for the VPAC2 receptor and can be more potent than VIP, PACAP, and other known VPAC2 receptor peptide agonists. An example of a preferred C-terminal extension is the extension peptide of Exendin-4 as the C-capping sequence. Exendin-4 is found in the salivary excretions from the Gila Monster, *Heloderma Suspectum*, (Eng et al., *J. Biol. Chem.*, 267(11):

7402-7405 (1992)). Other examples of C-terminal extensions are the C-terminal sequences of helodermin and helospectin. Helodermin and helospectin are also found in the salivary excretions of the Gila Monster.

It has furthermore been discovered that modification of the N-terminus of the VPAC2 receptor peptide agonist may enhance potency and/or provide stability against DPP-IV cleavage.

VIP and some known VPAC2 receptor peptide agonists are susceptible to cleavage by various enzymes and, thus, have a short in vivo half-life. Various enzymatic cleavage sites in the VPAC2 receptor peptide agonists are discussed below. The cleavage sites are discussed relative to the amino acid positions in VIP (SEQ ID NO: 14), and are applicable to the sequences noted herein.

Cleavage of the peptide agonist by the enzyme dipeptidyl-peptidase-IV (DPP-IV) occurs between position 2 (serine in VIP) and position 3 (aspartic acid in VIP). The agonists of the present invention may be rendered more stable to DPP-IV cleavage in this region by the addition of a N-terminal modification. Examples of N-terminal modifications that may improve stability against DPP-IV cleavage include the addition of acetyl, propionyl, butyryl, pentanoyl, hexanoyl, methionine, methionine sulfoxide, 3-phenylpropionyl, phenylacetyl, benzoyl, norleucine, D-histidine, isoleucine, 3-mercaptopropionyl, biotinyl-6-aminohexanoic acid, or —C(=NH$_2$)—NH$_2$. Preferably, the N-terminal modification is the addition of acetyl or hexanoyl.

There are chymotrypsin cleavage sites in wild-type VIP between the amino acids 10 and 11 (tyrosine and threonine) and those at 22 and 23 (tyrosine and leucine). Making substitutions at position 10 and/or 11 and position 22 and/or 23 may increase the stability of the peptide at these sites. For example, substitution of tyrosine at position 10 and/or position 22 with Tyr(OMe) may increase stability.

There is a trypsin cleavage site between the amino acids at positions 12 and 13 of wild-type VIP. Certain amino acids render the peptide less susceptible to cleavage at this site, for example, ornithine at position 12 and amino isobutyric acid at position 13.

In wild-type VIP, and in numerous VPAC2 receptor peptide agonists known in the art, there are cleavage sites between the basic amino acids at positions 14 and 15 and between those at positions 20 and 21. The selective PEGylated VPAC2 receptor peptide agonists of the present invention may have improved proteolytic stability in-vivo due to substitutions at these sites. The preferred substitutions at these sites are those which render the peptide less susceptible to cleavage by trypsin-like enzymes, including trypsin. For example, amino isobutyric acid at position 15, amino isobutyric acid at position 20, and ornithine at position 21 are all preferred substitutions which may lead to improved stability. The improved stability of a representative number of selective PEGylated VPAC2 receptor peptide agonists with resistance to peptidase cleavage and encompassed by the present invention is demonstrated in Example 7.

There is also a cleavage site between the amino acids at positions 25 and 26 of wild type VIP.

The region of the VPAC2 receptor peptide agonist encompassing the amino acids at positions 27, 28, 29, 30 and 31 is also susceptible to enzyme cleavage. The addition of a C-terminal extension may render the peptide agonist more stable against neuroendopeptidase (NEP), it may also increase selectivity for the VPAC2 receptor. This region may also be attacked by trypsin-like enzymes. If that occurs, the peptide agonist may lose its C-terminal extension with the additional carboxypeptidase activity leading to an inactive form of the peptide. Preferred substitutions which may increase resistance to cleavage in this region include ornithine at position 27, ornithine, or amino isobutyric acid at position 28 and ornithine at position 29.

In addition to selective PEGylated VPAC2 receptor peptide agonists with resistance to cleavage by various peptidases, the selective PEGylated VPAC2 peptide receptor agonists of the present invention may also encompass peptides with enhanced selectivity for the VPAC2 receptor, increased potency, and/or increased stability compared with some peptides known in the art. The increased potency and selectivity for various PEGylated VPAC2 receptor peptide agonists of the present invention is demonstrated in Examples 3, 4 and 5.

Table 1 in Example 3 provides a list of selective PEGylated VPAC2 receptor peptide agonists and their corresponding in vitro potency results. Preferably, the selective PEGylated VPAC2 receptor peptide agonists of the present invention have an $EC_{50}$ value less than 200 nM. More preferably, the $EC_{50}$ value is less than 100 nM. Even more preferably, the $EC_{50}$ value is less than 50 nM. Still more preferably, the $EC_{50}$ value is less than 30 nM.

Table 2 in Example 4 provides a list of PEGylated VPAC2 receptor peptide agonists and their corresponding receptor binding results for human VPAC2, VPAC1 and PAC1. See Example 4 for further details of these assays. The degree of selectivity is determined by a ratio of VPAC2 receptor binding affinity to VPAC1 receptor binding affinity and by a ratio of VPAC2 receptor binding affinity to PAC1 receptor binding affinity. Preferably, the agonists of the present invention have a selectivity ratio where the affinity for the VPAC2 receptor is at least 50 times greater than for the VPAC1 and/or for PAC1 receptors. More preferably, this affinity is at least 100 times greater for VPAC2 than for VPAC1 and/or for PAC1. Even more preferably, the affinity is at least 200 times greater for VPAC2 than for VPAC1 and/or for PAC1. Still more preferably, the affinity is at least 500 times greater for VPAC2 than for VPAC1 and/or for PAC1. Yet more preferably, the ratio is at least 1000 times greater for VPAC2 than for VPAC1 and/or for PAC1.

As used herein, "selective VPAC2 receptor peptide agonists" also include pharmaceutically acceptable salts of the agonists described herein. A selective VPAC2 receptor peptide agonist of this invention can possess a sufficiently acidic, a sufficiently basic, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, trifluoroacetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The selective PEGylated VPAC2 receptor peptide agonists of the present invention are preferably formulated as pharmaceutical compositions. Standard pharmaceutical formulation techniques may be employed such as those described in Remington's Pharmaceutical Sciences, Mack Publishing Company, Easton, Pa. The selective PEGylated VPAC2 receptor peptide agonists of the present invention may be formulated for administration through the buccal, topical, oral, transdermal, nasal, or pulmonary route, or for parenteral administration.

Parenteral administration can include, for example, systemic administration, such as by intramuscular, intravenous, subcutaneous, intradermal, or intraperitoneal injection. The selective PEGylated VPAC2 receptor peptide agonists can be administered to the subject in conjunction with an acceptable pharmaceutical carrier, diluent, or excipient as part of a pharmaceutical composition for treating NIDDM, or the disorders discussed below. The pharmaceutical composition can be a solution or, if administered parenterally, a suspension of the PEGylated VPAC2 receptor peptide agonist or a suspension of the PEGylated VPAC2 receptor peptide agonist complexed with a divalent metal cation such as zinc. Suitable pharmaceutical carriers may contain inert ingredients which do not interact with the peptide or peptide derivative. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol.

The PEGylated VPAC2 receptor peptide agonists of the invention may be formulated for administration such that blood plasma levels are maintained in the efficacious range for extended time periods. The main barrier to effective oral peptide drug delivery is poor bioavailability due to degradation of peptides by acids and enzymes, poor absorption through epithelial membranes, and transition of peptides to an insoluble form after exposure to the acidic pH environment in the digestive tract. Oral delivery systems for peptides such as those encompassed by the present invention are known in the art. For example, PEGylated VPAC2 receptor peptide agonists can be encapsulated using microspheres and then delivered orally. For example, PEGylated VPAC2 receptor peptide agonists can be encapsulated into microspheres composed of a commercially available, biocompatible, biodegradable polymer, poly(lactide-co-glycolide)-COOH and olive oil as a filler (see Joseph, et al. *Diabetologia* 43:1319-1328 (2000)). Other types of microsphere technology is also available commercially such as Medisorb® and Prolease® biodegradable polymers from Alkermes. Medisorb® polymers can be produced with any of the lactide isomers. Lactide:glycolide ratios can be varied between 0:100 and 100:0 allowing for a broad range of polymer properties. This allows for the design of delivery systems and implantable devices with resorption times ranging from weeks to months. Emisphere has also published numerous articles discussing oral delivery technology for peptides and proteins. For example, see WO 95/28838 by Leone-bay et al. which discloses specific carriers comprised of modified amino acids to facilitate absorption.

The selective PEGylated VPAC2 receptor peptide agonists described herein can be used to treat subjects with a wide variety of diseases and conditions. Agonists encompassed by the present invention exert their biological effects by acting at a receptor referred to as the VPAC2 receptor. Subjects with diseases and/or conditions that respond favourably to VPAC2 receptor stimulation or to the administration of VPAC2 receptor peptide agonists can therefore be treated with the PEGylated VPAC2 agonists of the present invention. These subjects are said to "be in need of treatment with VPAC2 agonists" or "in need of VPAC2 receptor stimulation".

The selective PEGylated VPAC2 receptor peptide agonists of the present invention may be employed to treat diabetes, including both type 1 and type 2 diabetes (non-insulin dependent diabetes mellitus or NIDDM). The agonists may also be used to treat subjects requiring prophylactic treatment with a VPAC2 receptor agonist, e.g., subjects at risk for developing NIDDM. Such treatment may also delay the onset of diabetes and diabetic complications. Additional subjects which may be treated with the agonists of the present invention include those with impaired glucose tolerance (IGT) (Expert Committee on Classification of Diabetes Mellitus, *Diabetes Care* 22 (Supp. 1):S5, 1999), or impaired fasting glucose (IFG) (Charles, et al., *Diabetes* 40:796, 1991), subjects whose body weight is about 25% above normal body weight for the subject's height and body build, subjects having one or more parents with NIDDM, subjects who have had gestational diabetes, and subjects with metabolic disorders such as those resulting from decreased endogenous insulin secretion. The selective PEGylated VPAC2 receptor peptide agonists may be used to prevent subjects with impaired glucose tolerance from proceeding to develop NIDDM, prevent pancreatic β-cell deterioration, induce β-cell proliferation, improve β-cell function, activate dormant β-cells, differentiate cells into β-cells, stimulate β-cell replication, and inhibit β-cell apoptosis. Other diseases and conditions that may be treated or prevented using agonists of the invention in methods of the invention include: Maturity-Onset Diabetes of the Young (MODY) (Herman, et al., *Diabetes* 43:40, 1994); Latent Autoimmune Diabetes Adult (LADA) (Zimmet, et al., *Diabetes Med.* 11:299, 1994); gestational diabetes (Metzger, *Diabetes,* 40:197, 1991); metabolic syndrome X, dyslipidemia, hyperglycemia, hyperinsulinemia, hypertriglyceridemia, and insulin resistance.

The selective PEGylated VPAC2 receptor peptide agonists of the invention may also be used to treat secondary causes of diabetes (Expert Committee on Classification of Diabetes Mellitus, *Diabetes Care* 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenyloin, thyroid hormone, β-adrenergic agents, α-interferon and drugs used to treat HIV infection.

The selective PEGylated VPAC2 receptor peptide agonists of the present invention may be effective in the suppression of food intake and the treatment of obesity.

The selective PEGylated VPAC2 receptor peptide agonists of the present invention may also be effective in the prevention or treatment of such disorders as atherosclerotic disease, hyperlipidemia, hypercholesteremia, low HDL levels, hypertension, primary pulmonary hypertension, cardiovascular disease (including atherosclerosis, coronary heart disease and coronary artery disease), cerebrovascular disease and peripheral vessel disease; and for the treatment of lupus, polycystic ovary syndrome, carcinogenesis, and hyperplasia, male and female reproduction problems, sexual disorders, ulcers, sleep disorders, disorders of lipid and carbohydrate metabolism, circadian dysfunction, growth disorders, disorders of energy homeostasis, immune diseases including autoimmune diseases (e.g., systemic lupus erythematosus), as well as acute and chronic inflammatory diseases, rheumatoid arthritis, and septic shock.

The selective PEGylated VPAC2 receptor peptide agonists of the present invention may also be useful for treating physiological disorders related to, for example, cell differentiation to produce lipid accumulating cells, regulation of insulin sensitivity and blood glucose levels, which are involved in, for example, abnormal pancreatic β-cell function, insulin secreting tumors and/or autoimmune hypoglycemia due to autoantibodies to insulin, autoantibodies to the insulin receptor, or autoantibodies that are stimulatory to pancreatic β-cells, macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

In addition, the selective PEGylated VPAC2 receptor peptide agonists of the invention may be used for treatment of asthma (Bolin, et al., *Biopolymer* 37:57-66 (1995); U.S. Pat. No. 5,677,419; showing that polypeptide R3PO is active in relaxing guinea pig tracheal smooth muscle); hypotension induction (VIP induces hypotension, tachycardia, and facial flushing in asthmatic patients (Morice, et al., *Peptides* 7:279-280 (1986); Morice, et al., *Lancet* 2:1225-1227 (1983)); for the treatment of male reproduction problems (Siow, et al., *Arch. Androl.* 43(1):67-71 (1999)); as an anti-apoptosis/neuroprotective agent (Brenneman, et al., *Ann. N.Y. Acad. Sci.* 865:207-12 (1998)); for cardioprotection during ischemic events (Kalfin, et al., *J. Pharmacol. Exp. Ther.* 1268(2):952-8 (1994); Das, et al., *Ann. N.Y. Acad. Sci.* 865:297-308 (1998)); for manipulation of the circadian clock and its associated disorders (Hamar, et al., *Cell* 109:497-508 (2002); Shen, et al., *Proc. Natl. Acad. Sci.* 97:11575-80, (2000)); and as an anti-ulcer agent (Tuncel, et al., *Ann. N.Y. Acad. Sci.* 865:309-22, (1998)).

An "effective amount" of a selective PEGylated VPAC2 receptor peptide agonist is the quantity that results in a desired therapeutic and/or prophylactic effect without causing unacceptable side effects when administered to a subject in need of VPAC2 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a PEGylated VPAC2 agonist for the treatment of NIDDM is the quantity that would result in greater control of blood glucose concentration than in the absence of treatment, thereby resulting in a delay in the onset of diabetic complications such as retinopathy, neuropathy, or kidney disease. An "effective amount" of a selective PEGylated VPAC2 receptor peptide agonist for the prevention of NIDDM is the quantity that would delay, compared with the absence of treatment, the onset of elevated blood glucose levels that require treatment with anti-hypoglycemic drugs such as sulfonylureas, thiazolidinediones, insulin, and/or bisguanidines.

An "effective amount" of the selective PEGylated VPAC2 receptor peptide agonist administered to a subject will also depend on the type and severity of the disease and on the characteristics of the subject, such as general health, age, sex, body weight and tolerance to drugs. The dose of selective PEGylated VPAC2 peptide receptor agonist effective to normalize a patient's blood glucose will depend on a number of factors, among which are included, without limitation, the subject's sex, weight and age, the severity of inability to regulate blood glucose, the route of administration and bioavailability, the pharmacokinetic profile of the peptide, the potency, and the formulation.

A typical dose range for the selective PEGylated VPAC2 receptor peptide agonists of the present invention will range from about 1 μg per day to about 5000 μg per day. Preferably, the dose ranges from about 1 μg per day to about 2500 μg per day, more preferably from about 1 μg per day to about 1000 μg per day. Even more preferably, the dose ranges from about 5 μg per day to about 100 μg per day. A further preferred dose range is from about 10 μg per day to about 50 μg per day. Most preferably, the dose is about 20 μg per day.

A "subject" is a mammal, preferably a human, but can also be an animal, e.g., companion animals (e.g., dogs, cats, and the like), farm animals (e.g., cows, sheep, pigs, horses, and the like) and laboratory animals (e.g., rats, mice, guinea pigs, and the like).

The selective PEGylated VPAC2 receptor peptide agonists of the present invention can be prepared by using standard methods of solid-phase peptide synthesis techniques. Peptide synthesizers are commercially available from, for example, Rainin-PTI Symphony Peptide Synthesizer (Tucson, Ariz.). Reagents for solid phase synthesis are commercially available, for example, from Glycopep (Chicago, Ill.). Solid phase peptide synthesizers can be used according to manufacturers instructions for blocking interfering groups, protecting the amino acid to be reacted, coupling, decoupling, and capping of unreacted amino acids.

Typically, an α-N-protected amino acid and the N-terminal amino acid on the growing peptide chain on a resin is coupled at room temperature in an inert solvent such as dimethylformamide, N-methylpyrrolidone or methylene chloride in the presence of coupling agents such as dicyclohexylcarbodiimide and 1-hydroxybenzotriazole and a base such as diisopropylethylamine. The α-N-protecting group is removed from the resulting peptide resin using a reagent such as trifluoroacetic acid or piperidine, and the coupling reaction repeated with the next desired N-protected amino acid to be added to the peptide chain. Suitable amine protecting groups are well known in the art and are described, for example, in Green and Wuts, "*Protecting Groups in Organic Synthesis*", John Wiley and Sons, 1991. Examples include t-butyloxycarbonyl (tBoc) and fluorenylmethoxycarbonyl (Fmoc).

The selective VPAC2 receptor peptide agonists may also be synthesized using standard automated solid-phase synthesis protocols using t-butoxycarbonyl- or fluorenylmethoxycarbonyl-alpha-amino acids with appropriate side-chain protection. After completion of synthesis, modification of the N-terminus may be accomplished by reacting the α-amino group with, for example: (i) active esters (using similar protocols as described above for the introduction of an α-N-protected amino acid); (ii) aldehydes in the presence of a reducing agent (reductive amination procedure); and (iii) guanidation reagents. Then, peptides are cleaved from the solid-phase support with simultaneous side-chain deprotection using standard hydrogen fluoride methods or trifluoroacetic acid (TFA). Crude peptides are then further purified using Reversed-Phase Chromatography on VYDAC C18 columns using acetonitrile gradients in 0.1% TFA. To remove acetonitrile, peptides are lyophilized from a solution containing 0.1% TFA, acetonitrile and water. Purity can be verified by analytical reversed phase chromatography. Identity of peptides can be verified by mass spectrometry. Peptides can be solubilized in aqueous buffers at neutral pH.

The peptide agonists of the present invention may also be made by recombinant methods known in the art using both eukaryotic and prokaryotic cellular hosts.

Once a peptide is prepared and purified, it is modified by covalently linking at least one PEG molecule to Cys or Lys residues, to K(W) or K(CO(CH$_2$)$_2$SH), or to the carboxy-terminal amino acid. A wide variety of methods have been described in the art to produce peptides covalently conjugated to PEG and the specific method used for the present invention is not intended to be limiting (for review article see, Roberts, M. et al. *Advanced Drug Delivery Reviews*, 54:459-476, 2002).

An example of a PEG molecule which may be used is methoxy-PEG2-MAL-40K, a bifurcated PEG maleimide (Nektar, Huntsville, Ala.). Other examples include, but are not limited to bulk mPEG-SBA-20K (Nektar), mPEG2-ALD-40K (Nektar) and methoxy-PEG-MAL-30K (Dow).

Carboxy-terminal attachment of PEG may be attached via enzymatic coupling using recombinant VPAC2 receptor peptide agonist as a precursor or alternative methods known in the art and described, for example, in U.S. Pat. No. 4,343,898 or *Intl. J. Pept. & Prot. Res.* 43:127-38 (1994).

One method for preparing the PEGylated VPAC2 receptor peptide agonists of the present invention involves the use of PEG-maleimide to directly attach PEG to a thiol group of the peptide. The introduction of a thiol functionality can be achieved by adding or inserting a Cys or hC residue onto or into the peptide at positions described above. A thiol functionality can also be introduced onto the side-chain of the peptide (e.g. acylation of lysine ε-amino group by a thiol-containing acid, such as mercaptopropionic acid). A PEGylation process of the present invention utilizes Michael addition to form a stable thioether linker. The reaction is highly specific and takes place under mild conditions in the presence of other functional groups. PEG maleimide has been used as a reactive polymer for preparing well-defined, bioactive PEG-protein conjugates. It is preferable that the procedure uses a molar excess, preferably from 1 to 10 molar excess, of a thiol-containing VPAC2 receptor peptide agonist relative to PEG maleimide to drive the reaction to completion. The reactions are preferably performed between pH 4.0 and 9.0 at room temperature for 10 minutes to 40 hours. The excess of unPEGylated thiol-containing peptide is readily separated from the PEGylated product by conventional separation methods. The PEGylated VPAC2 receptor peptide agonist is preferably isolated using reverse-phase HPLC or size exclusion chromatography. Specific conditions required for PEGylation of VPAC2 receptor peptide agonists are set forth in Example 8. Cysteine PEGylation may be performed using PEG maleimide or bifurcated PEG maleimide.

An alternative method for preparing the PEGylated VPAC2 receptor peptide agonists of the invention, involves PEGylating a lysine residue using a PEG-succinimidyl derivative. In order to achieve site specific PEGylation, the Lys residues which are not used for PEGylation are substituted for Arg residues.

Another approach for PEGylation is via Pictet-Spengler reaction. A Trp residue with its free amine is needed to incorporate the PEG molecule onto a VPAC2 receptor selective peptide. One approach to achieve this is to site specifically introduce a Trp residue onto the amine of a Lys sidechain via an amide bond during the solid phase synthesis (see Example 10).

Various preferred features and embodiments of the present invention will now be described only by way of the examples with reference to the following figure in which:—

FIG. 1 shows the enhancement of the insulin response to the i.v. glucose challenge in animals treated with P505 or P525 24 h prior to the glucose injection. The insulin response in vehicle-treated animals is shown for reference.

EXAMPLE 1

Preparation of the Selective VPAC2 Receptor Peptide Agonists by Solid Phase t-Boc Chemistry Approximately 0.5-0.6 grams (0.38-0.45 mmole) Boc Ser (Bzl)-PAM resin is placed in a standard 60 mL reaction vessel. Double couplings are run on an Applied Biosystems ABI430A peptide synthesizer.

The following side-chain protected amino acids (2 mmole cartridges of Boc amino acids) are obtained from Midwest Biotech (Fishers, Ind.) and are used in the synthesis:

Arg-Tosyl (TOS), Asp-δ-cyclohexyl ester (OcHx), Glu-δ-cyclohexyl ester (OcHx), His-benzyloxymethyl(BOM), Lys-2-chlorobenzyloxycarbonyl (2Cl—Z), Ser-O-benzyl ether (OBzl), Thr-O-benzyl ether (OBzl), Trp-formyl (CHO) and Tyr-2-bromobenzyloxycarbonyl (2Br—Z).

Trifluoroacetic acid (TFA), di-isopropylethylamine (DIEA), 0.5 M hydroxybenzotriazole (HOBt) in DMF and 0.5 M dicyclohexylcarbodiimide (DCC) in dichloromethane are purchased from PE-Applied Biosystems (Foster City, Calif.). Dimethylformamide (DMF-Burdick and Jackson) and dichloromethane (DCM-Mallinkrodt) is purchased from Mays Chemical Co. (Indianapolis, Ind.).

Standard double couplings are run using either symmetric anhydride or HOBt esters, both formed using DCC. At the completion of the syntheses, the N-terminal Boc group is removed and the peptidyl resins are treated with 20% piperidine in DMF to deformylate the Trp side chain if Trp is present in the sequence. For the N-terminal acylation, four-fold excess of symmetric anhydride of the corresponding acid is added onto the peptide resin. The symmetric anhydride is prepared by diisopropylcarbodiimde (DIC) activation in DCM. The reaction is allowed to proceed for 4 hours and monitored by ninhydrin test. After washing with DCM, the resins are transferred to a TEFLON reaction vessel and are dried in vacuo.

Cleavages are done by attaching the reaction vessels to a HF (hydrofluoric acid) apparatus (Penninsula Laboratories). 1 mL m-cresol per gram/resin is added and 10 mL HF (purchased from AGA, Indianapolis, Ind.) is condensed into the pre-cooled vessel. 1 mL DMS per gram resin is added when methionine is present. The reactions are stirred one hour in an ice bath. The HF is removed in vacuo. The residues are suspended in ethyl ether. The solids are filtered and are washed with ether. Each peptide is extracted into aqueous acetic acid and either is freeze dried or is loaded directly onto a reverse-phase column.

Purifications are run on a 2.2×25 cm VYDAC C18 column in buffer A (0.1% TFA in water). A gradient of 20% to 90% B (0.1% TFA in acetonitrile) is run on an HPLC (Waters) over 120 minutes at 10 mL/minute while monitoring the UV at 280 nm (4.0 A) and collecting one minute fractions. Appropriate fractions are combined, frozen and lyophilized. Dried products are analyzed by HPLC (0.46×15 cm METASIL AQ C18) and MALDI mass spectrometry.

EXAMPLE 2

Preparation of the Selective VPAC2 Receptor Peptide Agonists by Solid Phase FMoc Chemistry Approximately 114 mg (50 mMole) FMOC Ser(tBu) WANG resin (purchased from GlycoPep, Chicago, Ill.) is placed in each reaction vessel. The synthesis is conducted on a Rainin Symphony Peptide Synthesizer. Analogs with a C-terminal amide are prepared using 75 mg (50 µmole) Rink Amide 1M resin (Rapp Polymere. Tuebingen, Germany).

The following FMOC amino acids are purchased from GlycoPep (Chicago, Ill.), and NovaBiochem (La Jolla, Calif.): Arg-2,2,4,6,7-pentamethyldihydrobenzofuran-5-sulfonyl (Pbf), Asn-trityl (Trt), Asp-β-t-Butyl ester (tBu), Glu-δ-t-butyl ester (tBu), Gln-trityl (Trt), His-trityl (Trt), Lys-t-butyloxycarbonyl (Boc), Ser-t-butyl ether (OtBu), Thr-t-butyl ether (OtBu), Trp-t-butyloxycarbonyl (Boc), Tyr-t-butyl ether (OtBu).

Solvents dimethylformamide (DMF-Burdick and Jackson), N-methylpyrrolidone (NMP-Burdick and Jackson), dichloromethane (DCM-Mallinkrodt) are purchased from Mays Chemical Co. (Indianapolis, Ind.).

Hydroxybenzotrizole (HOBt), di-isopropylcarbodiimide (DIC), di-isopropylethylamine (DIEA), and piperidine (Pip) are purchased from Aldrich Chemical Co (Milwaukee, Wis.).

All amino acids are dissolved in 0.3 M in DMF. Three hour DIC/HOBt activated couplings are run after 20 minutes deprotection using 20% Pip/DMF. Each resin is washed with DMF after deprotections and couplings. After the last coupling and deprotection, the peptidyl resins are washed with DCM and are dried in vacuo in the reaction vessel. For the N-terminal acylation, four-fold excess of symmetric anhydride of the corresponding acid is added onto the peptide resin. The symmetric anhydride is prepared by DIC activation in DCM. The reaction is allowed to proceed for 4 hours and monitored by ninhydrin test. The peptide resin is then washed with DCM and dried in vacuo.

The cleavage reaction is mixed for 2 hours with a cleavage cocktail consisting of 0.2 mL thioanisole, 0.2 mL methanol, 0.4 mL triisopropylsilane, per 10 mL TFA, all purchased from Aldrich Chemical Co., Milwaukee, Wis. If Cys is present in the sequence, 2% of ethanedithiol is added. The TFA filtrates are added to 40 mL ethyl ether. The precipitants are centrifuged 2 minutes at 2000 rpm. The supernatants are decanted. The pellets are resuspended in 40 mL ether, re-centrifuged, re-decanted, dried under nitrogen and then in vacuo.

0.3-0.6 mg of each product is dissolved in 1 mL 0.1% TFA/acetonitrile (ACN), with 20 µL being analyzed on HPLC [0.46×15 cm METASIL AQ C18, 1 mL/min, 45° C., 214 nM (0.2 A), A=0.1% TFA, B=0.1% TFA/50% ACN. Gradient=50% B to 90% B over 30 minutes].

Purifications are run on a 2.2×25 cm VYDAC C18 column in buffer A (0.1% TFA in water). A gradient of 20% to 90% B (0.1% TFA in acetonitrile) is run on an HPLC (Waters) over 120 minutes at 10 mL/minute while monitoring the UV at 280 nm (4.0 A) and collecting 1 minute fractions. Appropriate fractions are combined, frozen and lyophilized. Dried products are analyzed by HPLC (0.46×15 cm METASIL AQ C18) and MALDI mass spectrometry.

Precursor to P521 (C6-HSDAVFTEQY(OMe)TOrnL-RAibQLAAbuAibOrnY AibQSIOrnOrnGGPSSGAPPPCC-NH$_2$): Synthesis is carried out using the FMoc protocols described above. The peptide is characterised by analytical HPLC: $t_R$=10.9 min, HPLC conditions as described above, and MALDI-TOF: calculated m/z=4290.0, measured m/z=4290.8 [M+H$^+$]. After purification using reversed-phase preparative HPLC, pure fractions are combined and lyophilised: 14.8 mg is obtained as a final lyophilised powder.

Precursor to P525 (C6-HSDAVFTEQY(OMe)TOrnL-RAibQLAAbuAibOrnYAibQ AibIOrnOrnGGPSSGAPP-PCC-NH$_2$): As described for the precursor to P521. Analytical HPLC: $t_R$=11.0 min. MALDI-TOF: calculated m/z=4288.0, measured m/z=4288.8 [M+H$^+$]. 18.7 mg is obtained as a final lyophilised powder.

Precursor to P574 (C6-HSDAVFTEQY(OMe)TOrnL-RAibQLAAbuAibOrn Y(OMe)LQAibIOrnOrnGGPSS-GAPPPCC-NH$_2$): As described for the precursor to P521. Analytical HPLC: $t_R$=11.7 min. MALDI-TOF: calculated m/z=4330.1, measured m/z=4330.7 [M+H$^+$]. 46.2 mg is obtained as a final lyophilised powder.

EXAMPLE 3

In-Vitro Potency at Human VPAC2 Receptors

Alpha screen: Cells are washed in the culture flask once with PBS. Then, the cells are rinsed with enzyme free dissociation buffer. The dissociated cells are removed. The cells are then spun down and washed in stimulation buffer. For each data point, 50,000 cells suspended in stimulation buffer are used. To this buffer, Alpha screen acceptor beads are added along with the stimuli. This mixture is incubated for 60 minutes. Lysis buffer and Alpha screen donor beads are added and are incubated for 60 to 120 minutes. The Alpha screen signal (indicative of intracellular cAMP levels) is read in a suitable instrument (e.g. AlphaQuest from Perkin-Elmer). Steps including Alpha screen donor and acceptor beads are performed in reduced light. The EC$_{50}$ for cAMP generation is calculated from the raw signal or is based on absolute cAMP levels as determined by a standard curve performed on each plate.

Results for each agonist are, at minimum, from two analyses performed in a single run. For some agonists, the results are the mean of more than one run. The tested peptide concentrations are: 10000, 1000, 100, 10, 3, 1, 0.1, 0.01, 0.003, 0.001, 0.0001 and 0.00001 nM.

DiscoveRx: A CHO-S cell line stably expressing human VPAC2 receptor in a 96-well microtiter plate is seeded with 50,000 cells/well the day before the assay. The cells are allowed to attach for 24 hours in 200 µL culture medium. On the day of the experiment, the medium is removed. Also, the cells are washed twice. The cells are incubated in assay buffer plus IBMX for 15 minutes at room temperature. Afterwards, the stimuli are added and are dissolved in assay buffer. The stimuli are present for 30 minutes. Then, the assay buffer is gently removed. The cell lysis reagent of the DiscoveRx cAMP kit is added. Thereafter, the standard protocol for developing the cAMP signal as described by the manufacturer is used (DiscoveRx Inc., USA). EC$_{50}$ values for cAMP generation are calculated from the raw signal or are based on absolute cAMP levels as determined by a standard curve performed on each plate.

Results for each agonist are the mean of two independent runs. The typically tested concentrations of peptide are: 1000, 300, 100, 10, 1, 0.3, 0.1, 0.01, 0.001, 0.0001 and 0 nM.

The activity (EC$_{50}$ (nM)) for the human VPAC2 receptor is reported in Table 1 for the different assay formats.

TABLE 1

Peptide potency at human VPAC2 receptors

| Agonist # | Human VPAC2 Receptor: Alphascreen ($EC_{50}$; nM) | Human VPAC2 Receptor: DiscoveRx ($EC_{50}$; nM) |
|---|---|---|
| VIP | 1.0 | 0.7 |
| PACAP-27 | 2.3 | 0.8 |
| P410 | 128.8 | |
| P417 | 14.7 | |
| P451 | 68.6 | |
| P454 | 59.9 | |
| P460 | 430.2 | |
| P470 | 83.3 | |
| P472 | 123.3 | |
| P473 | 26.5 | |
| P475 | 109.3 | |
| P478 | 49.9 | |
| P483 | 33.5 | |
| P485 | 44.5 | |
| P490 | 115.6 | |
| P492 | 509.6 | |
| P495 | 116.7 | |
| P497 | 176.1 | |
| P499 | 57.7 | |
| P501 | 130.9 | |
| P503 | 146.8 | |
| P505 | 40.5 | |
| P507 | 27.1 | |
| P509 | 13.0 | |
| P511 | 7.6 | |
| P513 | 28.9 | |
| P517 | 7.5 | |
| P519 | 30.3 | |
| P521 | 22.1 | |
| P523 | 5.8 | |
| P525 | 25.0 | |
| P529 | 170.5 | |
| P531 | 94.6 | |
| P533 | 2382.0 | |
| P535 | 98.4 | |
| P537 | 32.0 | |
| P541 | 45.8 | |
| P545 | 45.0 | |
| P547 | 62.0 | |
| P539 | 10.7 | 47.3 |
| P543 | 84.2 | 8.9 |
| P551 | 15.6 | |
| P553 | 15.0 | |
| P555 | 22.5 | 8.1 |
| P557 | | 108.3 |
| P560 | 13.8 | 11.3 |
| P562 | 30.2 | 24.2 |
| P566 | 11.8 | 7.8 |
| P568 | 128.6 | |
| P570 | 13.4 | 4.5 |
| P572 | 11.2 | |
| P574 | 21.2 | 36.1 |
| P576 | 55.0 | |
| P578 | 205.3 | |
| P580 | 10.9 | |
| P582 | 20.3 | |
| P584 | 51.2 | |
| P586 | 122.4 | |
| P588 | 54.0 | |
| P590 | 4.1 | |
| P602 | 42.1 | 7.2 |

EXAMPLE 4

Selectivity

Binding assays: Membrane prepared from a stable VPAC2 cell line (see Example 3) or from cells transiently transfected with human VPAC1 or PAC1 are used. A filter binding assay is performed using 125I-labeled VIP for VPAC1 and VPAC2 and 125I-labeled PACAP-27 for PAC as the tracers.

For this assay, the solutions and equipment include:
Presoak solution: 0.5% Polyethyleneamine in Aqua dest
Buffer for flushing filter plates: 25 mM HEPES pH 7.4
Blocking buffer: 25 mM HEPES pH 7.4; 0.2% protease free BSA
Assay buffer: 25 mM HEPES pH 7.4; 0.5% protease free BSA
Dilution and assay plate: PS-Microplate, U form
Filtration Plate Multiscreen FB Opaque Plate; 1.0 mM Type B Glasfiber filter In order to prepare the filter plates, the presoak solution is aspirated by vacuum filtration. The plates are flushed twice with 200 µL flush buffer. 200 µL blocking buffer is added to the filter plate. The filter plate is then incubated with 200 µL presoak solution for 1 hour at room temperature.

The assay plate is filled with 25 µL assay buffer, 25 µL membranes (2.5 µg) suspended in assay buffer, 25 µL agonist in assay buffer, and 25 µL tracer (about 40000 cpm) in assay buffer. The filled plate is incubated for 1 hour with shaking.

The transfer from assay plate to filter plate is conducted. The blocking buffer is aspirated by vacuum filtration and washed two times with flush buffer. 90 µL is transferred from the assay plate to the filter plate. The 90 µL transferred from assay plate is aspirated and washed three times with 200 µL flush buffer. The plastic support is removed. It is dried for 1 hour at 60° C. 30 µL Microscint is added. The count is performed.

The receptor binding ($IC_{50}$) for human VPAC2, VPAC1 and PAC1 is reported in Table 2.

TABLE 2

| Agonist # | Human VPAC2 Receptor Binding (IC50; nM) | Human VPAC1 Receptor Binding (IC50; nM) | Human PAC1 Receptor Binding (IC50; nM) |
|---|---|---|---|
| VIP | 5.1 | 3.3 | >1000 |
| PACAP-27 | 2.6 | 4.5 | 10.2 |
| P410 | 264.4 | >25000 | |
| P417 | 24.1 | >25000 | |
| P451 | 595.7 | | |
| P454 | 36.6 | >25000 | |
| P460 | 914.5 | >25000 | |
| P470 | 262.9 | | |
| P473 | 256.4 | >25000 | |
| P475 | 436.0 | | |
| P478 | 30.0 | | |
| P483 | 37.3 | >25000 | |
| P485 | 17.3 | | |
| P490 | 13.2 | | |
| P492 | 156.0 | | |
| P495 | 142.1 | | |
| P497 | 146.0 | | |
| P499 | 34.0 | >25000 | |
| P501 | 111.0 | | |
| P503 | 41.5 | | |
| P505 | 26.1 | >25000 | >25000 |
| P509 | 11.2 | >25000 | |
| P511 | 7.2 | >25000 | >25000 |
| P513 | 50.5 | | |
| P517 | 3.7 | >25000 | |
| P519 | 51.6 | | |
| P521 | 67.1 | | |
| P523 | 4.8 | | |
| P525 | 41.8 | >25000 | >25000 |
| P529 | 192.4 | | |
| P531 | 69.7 | | |
| P533 | 959.0 | | |
| P535 | 145.4 | >25000 | |

TABLE 2-continued

| Agonist # | Human VPAC2 Receptor Binding (IC50; nM) | Human VPAC1 Receptor Binding (IC50; nM) | Human PAC1 Receptor Binding (IC50; nM) |
|---|---|---|---|
| P537 | 17.2 | >25000 | >25000 |
| P539 | 13.5 | | |
| P541 | 59.8 | >25000 | |
| P543 | 56.3 | | |
| P545 | 79.9 | >25000 | >25000 |
| P547 | 5.6 | | |
| P551 | 16.6 | >25000 | >25000 |
| P553 | 21.7 | >25000 | >25000 |
| P555 | 15.4 | >25000 | >25000 |
| P557 | 380.0 | | |
| P560 | 11.6 | | |
| P562 | 42.8 | >25000 | >25000 |
| P566 | 8.2 | | |
| P570 | 4.1 | >25000 | >25000 |
| P572 | 14.9 | >25000 | >25000 |
| P574 | 32.3 | >25000 | >25000 |
| P580 | 20.7 | >25000 | >25000 |
| P582 | 48.3 | >25000 | >25000 |
| P590 | 7.4 | >25000 | >25000 |
| P602 | 28.0 | >25000 | >25000 |

EXAMPLE 5

In Vitro Potency at Rat VPAC1 and VPAC2 Receptors

DiscoveRx: CHO-PO cells are transiently transfected with rat VPAC1 or VPAC2 receptor DNA using commercially available transfection reagents (Lipofectamine from Invitrogen). The cells are seeded at a density of 10,000/well in a 96-well plate and are allowed to grow for 3 days in 200 ml culture medium At day 3, the assay is performed.

On the day of the experiment, the medium is removed. Also, the cells are washed twice. The cells are incubated in assay buffer plus IBMX for 15 minutes at room temperature. Afterwards, the stimuli are added and are dissolved in assay buffer. The stimuli are present for 30 minutes. Then, the assay buffer is gently removed. The cell lysis reagent of the DiscoveRx cAMP kit is added. Thereafter, the standard protocol for developing the cAMP signal as described by the manufacturer is used (DiscoveRx Inc., USA). $EC_{50}$ values for cAMP generation are calculated from the raw signal or are based on absolute cAMP levels as determined by a standard curve performed on each plate.

Results for each agonist are the mean of two independent runs. Rat VPAC1 and VPAC2 results are only generated using the DiscoveRx assay. The typically tested concentrations of peptide are: 1000, 300, 100, 10, 1, 0.3, 0.1, 0.01, 0.001, 0.0001 and 0 nM.

The activity ($EC_{50}$ (nM)) for the rat VPAC2 and VPAC1 receptors is reported in Table 3.

TABLE 3

| Agonist # | Rat VPAC1 Receptor: DiscoveRx: ($EC_{50}$; nM) | Rat VPAC2 Receptor: DiscoveRx: ($EC_{50}$; nM) |
|---|---|---|
| VIP | 0.01 | 0.6 |
| P410 | >1000 | 318.5 |
| P417 | 232.3 | 8.7 |
| P454 | 1229.5 | 79.6 |
| P460 | >1000 | 1163.1 |
| P470 | >1000 | 110.9 |
| P472 | >1000 | 284.6 |
| P473 | >1000 | 25.5 |
| P475 | >1000 | 220.4 |
| P478 | 2053.8 | 120.1 |
| P483 | 223.9 | 128.4 |
| P485 | 734.9 | 42.5 |
| P490 | >1000 | 191.8 |
| P492 | >4000 | 962.7 |
| P497 | >1000 | 344.7 |
| P499 | 803.8 | 68.2 |
| P501 | >1000 | 272.1 |
| P503 | >4000 | 520.3 |
| P505 | 639.4 | 42.6 |
| P507 | >1000 | 94.9 |
| P509 | 328.4 | 28.2 |
| P511 | 61.9 | 13.9 |
| P517 | 92.4 | 10.0 |
| P521 | 602.4 | 33.1 |
| P523 | 20.4 | 5.3 |
| P525 | 1137.3 | 44.0 |
| P529 | 1182.9 | 199.3 |
| P531 | 300.7 | 69.9 |
| P535 | >1000 | 317.6 |
| P537 | 205.8 | 38.8 |
| P539 | 32.6 | 21.0 |
| P541 | 665.1 | 101.9 |
| P543 | 355.0 | 101.1 |
| P545 | 380.5 | 99.5 |
| P547 | 76.2 | 149.8 |
| P551 | 171.9 | 13.2 |
| P553 | 261.8 | 22.0 |
| P555 | 68.9 | 32.5 |
| P557 | 581.1 | 397.2 |
| P560 | 155.6 | 20.4 |
| P562 | 393.4 | 52.5 |
| P566 | 52.7 | 13.1 |
| P568 | >1000 | 250.3 |
| P570 | 86.7 | 21.3 |
| P572 | 94.5 | 10.8 |
| P574 | 162.9 | 33.8 |
| P576 | 460.9 | 67.4 |
| P578 | 269.4 | 305.6 |
| P580 | 1.1 | 11.9 |
| P582 | 137.4 | 31.0 |
| P584 | 188.1 | 67.2 |
| P586 | 501.6 | 186.8 |
| P588 | 406.3 | 311.2 |
| P590 | 245.0 | 6.9 |
| P602 | 209.0 | 36.9 |

EXAMPLE 6

In Vivo Assays

Intravenous glucose tolerance test (IVGTT): Normal Wistar rats are fasted overnight and are anesthetized prior to the experiment. A blood sampling catheter is inserted into the rats. The agonist is given subcutaneously, normally 24 h prior to the glucose challenge. Blood samples are taken from the carotid artery. A blood sample is drawn immediately prior to the injection of glucose along with the agonist. After the initial blood sample, glucose mixed is injected intravenously (i.v.). A glucose challenge of 0.5 g/kg body weight is given, injecting a total of 1.5 mL vehicle with glucose and agonist per kg body weight. The peptide concentrations are varied to produce the desired dose in μg/kg. Blood samples are drawn at 2, 4, 6 and 10 minutes after giving glucose. The control group of animals receives the same vehicle along with glucose, but with no agonist added. In some instances, 20 and 30 minute post-glucose blood samples were drawn. Aprotinin is added to the blood sample (250-500 kIU/ml blood). The plasma is then analyzed for glucose and insulin using standard methodologies.

The assay uses a formulated and calibrated peptide stock in PBS. Normally, this stock is a prediluted 100 μM stock. However, a more concentrated stock with approximately 1 mg agonist per mL is used. The specific concentration is always known. Variability in the maximal response is mostly due to variability in the vehicle dose. Protocol details are as follows:

| | |
|---|---|
| SPECIES/STRAIN/WEIGHT | Rat/Wistar Unilever/approximately 275-300 g |
| TREATMENT DURATION | Single dose |
| DOSE VOLUME/ROUTE | 1.5 mL/kg/iv |
| VEHICLE | 8% PEG300, 0.1% BSA in water |
| FOOD/WATER REGIMEN | Rats are fasted overnight prior to surgery. |
| LIVE-PHASE PARAMETERS | Animals are sacrificed at the end of the test. |
| IVGTT: Performed on rats (with two catheters, jugular vein and carotid artery) of each group, under pentobarbital anesthesia. | Glucose IV bolus: 500 mg/kg as 10% solution (5 mL/kg) at time = 0. Compound iv: 0-240 min prior to glucose Blood samplings (300 μL from carotid artery; EDTA as anticoagulant; aprotinin and PMSF as antiproteolytics; kept on ice): 0, 2, 4, 6, and 10, 20 and 30 minutes. Parameters determined: Insulin + glucose |
| TOXICOKINETICS | Plasma samples remaining after insulin measurements are kept at −20° C. and compound levels are determined. |

TABLE 4a

| Agonist # | Time between glucose & compound | % increase AUC: Dose = 0.09 mg/kg | % increase AUC: Dose = 0.1 mg/kg | % increase AUC: Dose = 0.3 mg/kg |
|---|---|---|---|---|
| P505 | 24 h | | 12 | 74 |
| P511 | 24 h | | 38 | 59 |
| P525 | 24 h | | 72 | 208 |
| P570 | 24 h | | 36 | |
| P602 | 24 h | 73 | | 198 |

AUC = Area under curve (insulin, 0-10 min after glucose)

Pharmacokinetic profiles of PEGylated peptides. Healthy Fisher 344 rats (3 animals per group) were injected with 100 μg agonist/kg (agonist amount based on peptide content and dissolved in PBS buffer). Blood samples were drawn 3, 12, 24, 48, 72, 96 and 168 hour post dosing and the peptide content in plasma was analysed by a radio-immunoassay (RIA) directed against the N-terminus of the peptide. PK parameters were then calculated using a model-independent method (WinNonlin Pro, Pharsight Corp., Mountain View, Calif., USA).

TABLE 4b

PK parameters of PEGylated peptide agonists. Mean and (SD) values for N = 3.

| Agonist # | Cmax (ng/mL) | Tmax (h) | $AUC_{0-last}$ (ng * h/mL) | $T\frac{1}{2}$ (h) | Cl/F (mL/h/kg) | Vd/F (mL/kg) |
|---|---|---|---|---|---|---|
| P499 | 132 | 24 | 6650 | 25 | 15 | 529 |
| | (9) | (<1) | (1294) | (5) | (2) | (85) |
| P505 | 160 | 12 | 7006 | 22 | 13 | 425 |
| | (30) | (<1) | (890) | (5) | (1) | (116) |
| P511 | 100 | 16 | 3067 | NC | NC | NC |
| | (16) | (7) | (374) | NC | NC | NC |
| P521 | 233 | 12 | 7633 | 19 | 13 | 380 |
| | (29) | (<1) | (1871) | (6) | (3) | (208) |
| P525 | 133 | 16 | 4740 | 22 | 20 | 642 |
| | (21) | (7) | (486) | (3) | (2) | (126) |
| P539 | 102 | 24 | 4013 | 15 | 25 | 540 |
| | (16) | (<1) | (511) | (2) | (3) | (129) |
| P545 | 139 | 72 | 12737 | 43 | 7 | 457 |
| | (48) | (42) | (2492) | (5) | (2) | (66) |
| P555 | 102 | 16 | 4918 | 13 | 20 | 389 |
| | (9) | (7) | (597) | (1) | (3) | (65) |
| P562 | 120 | 24 | 5456 | 25 | 19 | 673 |
| | (67) | (21) | (2157) | (7) | (6) | (315) |
| P570 | 71 | 20 | 3891 | 25 | 25 | 877 |
| | (34) | (7) | (1309) | (4) | (7) | (326) |
| P574 | 70 | 20 | 3408 | 18 | 28 | 727 |
| | (6) | (7) | (312) | (2) | (2) | (71) |

*NC = not calculated due to insufficient data

EXAMPLE 7

Rat Serum Stability Studies

In order to determine the stability of VPAC2 receptor peptide agonists in rat serum, CHO-VPAC2 cells clone #6 (96 well plates/50,000 cells/well and 1 day culture), PBS 1× (Gibco), the peptides for the analysis in a 100 μM stock solution, rat serum from a sacrificed normal Wistar rat, aprotinin, and a DiscoveRx assay kit are obtained. The rat serum is stored at 4° C. until use and is used within two weeks.

On Day 0, two 100 μL aliquots of 10 μM peptide in rat serum are prepared by adding 10 μL peptide stock to 90 μL rat serum for each aliquot. 250 kIU aprotinin/mL is added to one of these aliquots. The aliquot is stored with aprotinin at 4° C. The aliquot is stored without aprotinin at 37° C. The aliquots are incubated for 24 or 72 hours.

On Day 1, after incubation of the aliquots prepared on day 0 for 24 or 72 hours, an incubation buffer containing PBS+1.3 mM $CaCl_2$, 1.2 mM $MgCl_2$, 2 mM glucose, and 0.25 mM IBMX is prepared. A plate with 11 serial 5× dilutions of peptide for the 4° C. and 37° C. aliquot is prepared for each peptide studied. 2000 nM is used as the maximal concentration if the peptide has an $EC_{50}$ above 1 nM and 1000 nM as maximal concentration if the peptide has an $EC_{50}$ below 1 nM from the primary screen (see Example 3). The plate(s) are washed with cells twice in incubation buffer. The plates are allowed to hold 50 μL incubation media per well for 15 minutes. 50 μL solution per well is transferred to the cells from the plate prepared with 11 serial 5× dilutions of peptide for the 4° C. and 37° C. aliquot for each peptide studied, using the maximal concentrations that are indicated by the primary screen, in duplicate. This step dilutes the peptide concentration by a factor of two. The cells are incubated at room temperature for 30 minutes. The supernatant is removed. 40 μL/well of the DiscoveRx antibody/extraction buffer is added. The cells are incubated on the shaker (300 rpm) for 1 hour. Normal procedure with the DiscoveRx kit is followed.

cAMP standards are included in column 12. $EC_{50}$ values are determined from the cAMP assay data. The remaining amount of active peptide is estimated by the formula $EC_{50, 4° C.}/EC_{50, 37° C.}$ for each condition.

TABLE 5

Estimated peptide stability after 24 h or 72 h in rat serum at 37° C.

| Agonist # | 24 h stab (%) | 72 h stab (%) |
|---|---|---|
| VIP | 0.2 | |
| P417 | 265 | |
| P472 | 66 | |
| P473 | 86 | |
| P475 | 61 | |
| P478 | 34 | |
| P483 | 22 | |
| P485 | 65 | |
| P492 | 131 | |
| P503 | 174 | |
| P505 | 133 | 161 |
| P521 | | 294 |
| P523 | | 281 |
| P525 | 298 | 353 |
| P529 | | 119 |
| P543 | 119 | |
| P539 | 123 | |
| P555 | 117 | |
| P557 | 131 | |
| P560 | 192 | |
| P562 | 213 | |
| P566 | 152 | |
| P574 | 288 | |
| P602 | 573 | |

[1]Values >100% may represent release of intact peptide from the PEG conjugate

EXAMPLE 8

PEGylation of Selective VPAC2 Receptor Peptide Agonists Using Thiol-Based Chemistry In general, PEGylation reactions are run under conditions that permit the formation of a thioether bond. Specifically, the pH of the solution ranges from about 4 to 9 and the thiol-containing peptide concentrations range from 0.7 to 10 molar excess of PEG maleimide concentration. The PEGylation reactions are normally run at room temperature. The PEGylated VPAC2 receptor peptide agonist is then isolated using reverse-phase HPLC or size exclusion chromatography (SEC). PEGylated peptide agonists are characterized using analytical RP-HPLC, HPLC-SEC, SDS-PAGE, and/or MALDI Mass Spectrometry.

Usually a thiol function is introduced into or onto a selective VPAC2 receptor peptide agonist by adding a cysteine or a homocysteine or a thiol-containing moiety at either or both termini or by inserting a cysteine or a homocysteine or a thiol-containing moiety into the sequence. Thiol-containing VPAC2 receptor peptide agonists are reacted with 40 kDa, 30 kDa or 20 kDa PEG-maleimide to produce derivatives with PEG covalently attached via a thioether bond.

Synthesis of P505

19 mg of the peptide precursor (non-PEGylated P505) and 162 mg of methoxy-PEG-maleimide (NOF, Japan) with an average molecular weight of 20,000 Daltons are dissolved in 2 mL of 100 mM NH$_4$Ac buffer containing 10 mM EDTA (pH 6.8) and the reaction is allowed to proceed for 4 h. 97 mg of the product is obtained as a lyophilized powder after preparative RP-HPLC purification. The PEGylated peptide agonist is characterized by RP-HPLC and size-exclusion HPLC, and tested for in vitro activity.

Synthesis of P525

18.7 mg of the peptide precursor (non-PEGylated P525) and 157 mg of methoxy-PEG-maleimide with an average molecular weight of 20,000 Daltons are dissolved in 2 mL of 100 mM NH$_4$Ac buffer containing 10 mM EDTA (pH 6.8) and the reaction is allowed to proceed for 4 h. 114 mg of the product is obtained as a lyophilized powder after preparative RP-HPLC purification. The PEGylated peptide agonist is characterized by RP-HPLC and size-exclusion HPLC, and tested for in vitro activity.

Synthesis of P572

22.3 mg of the peptide precursor (non-PEGylated P572), and 177 mg of methoxy-PEG-maleimide with an average molecular weight of 20,000 Daltons are dissolved in 2 mL of 100 mM NH$_4$Ac buffer containing 10 mM EDTA (pH 6.8) and the reaction is allowed to proceed for 4 h. 137 mg of the product is obtained as a lyophilized powder after preparative RP-HPLC purification. The PEGylated peptide agonist is characterized by RP-HPLC and size-exclusion HPLC, and tested for in vitro activity.

Synthesis of P574

31.9 mg of the peptide precursor (non-PEGylated P574) and 283 mg of methoxy-PEG-maleimide with an average molecular weight of 20,000 Daltons are dissolved in 3 mL of 100 mM NH$_4$Ac buffer containing 10 mM EDTA (pH 6.8) and the reaction is allowed to proceed for 4 h. 171 mg of the product is obtained as a lyophilized powder after two runs of preparative RP-HPLC purifications. The PEGylated peptide agonist is characterized by RP-HPLC and size-exclusion HPLC, and tested for in vitro activity.

Synthesis of P602

20 mg of the peptide precursor (non-PEGylated P602) and 223 mg of methoxy-poly(ethyleneglycol) maleimido-propio-aamide (Chirotech Technology Ltd., UK) with an average molecular weight of 30,000 Daltons are dissolved in 2 mL of 100 mM NH$_4$Ac buffer containing 10 mM EDTA (pH 6.8) and the reaction is allowed to proceed for 4 h. 132 mg of the product is obtained as a lyophilized powder after preparative RP-HPLC purification. The PEGylated peptide agonist is characterized by RP-HPLC and size-exclusion HPLC, and tested for in vitro activity.

EXAMPLE 9

PEGylation Via Acylation on the Sidechain of Lysine

In order to achieve site-specific PEGylation of selective VPAC2 receptor peptide agonists, all the Lys residues are changed into Arg residues except for Lys residues where PEGylation is intended. A PEG molecule which may be used is mPEG-SBA-20K (Nektar, Lot #: PT-04E-11). The PEGylation reaction is preferably performed at room temperature for 2-3 hours. The peptide is purified by preparative HPLC.

EXAMPLE 10

PEGylation Via Pictet-Spengler Reaction

For PEGylation via Pictet-Spengler reaction to occur, a Trp residue with its free amine is needed to incorporate the PEG molecule onto the selective VPAC2 receptor peptide agonist. To couple a Trp residue onto the sidechain of Lys residue. The extensive SAR indicates that this modification does not change the properties of the parent peptide in terms of its in vitro potency and selectivity.

PEG with a functional aldehyde, for example mPEG2-BUTYRALD-40K (Nektar, USA), is used for the reaction. The site specific PEGylation involves the formation a tetra-carboline ring between PEG and the peptide. PEGylation is conducted in glacial acetic acid at room temperature for 1 to 48 hours. A 1 to 10 molar excess of the PEG aldehyde is used in the reaction. After the removal of acetic acid, the PEGylated VPAC2 receptor peptide agonist is isolated by preparative RP-HPLC.

Synthesis of P535

27.7 mg of the peptide precursor (non-PEGylated P535) and 590 mg of mPEG2-BUTYRALD-40K are dissolved in 3 mL acetic acid and the reaction is allowed to proceed for 2 days. The product is isolated by preparative RP-HPLC to yield 94 mg of the PEGylated peptide agonist as a lyophilized powder. The PEGylated peptide agonist is characterized by RP-HPLC and size-exclusion HPLC, and tested for in vitro.

Synthesis of P557

23 mg of the peptide precursor (non-PEGylated P557) and 460 mg of mPEG2-BUTYRALD-40K are dissolved in 3 mL acetic acid and the reaction is allowed to proceed for 2 days. The product is isolated by preparative RP-HPLC to yield 50 mg of the PEGylated peptide agonist as a lyophilized powder. The PEGylated peptide agonist is characterized by RP-HPLC and size-exclusion HPLC, and tested for in vitro.

Other modifications of the present invention will be apparent to those skilled in the art without departing from the scope of the invention.

The invention claimed is:

1. A PEGylated VPAC2 receptor peptide agonist, comprising a sequence of the formula:

Formula 4

(SEQ ID NO: 4)

$Xaa_1$-$Xaa_2$-$Xaa_3$-$Xaa_4$-$Xaa_5$-$Xaa_6$-Thr-$Xaa_8$-$Xaa_9$-

$Xaa_{10}$-Thr-$Xaa_{12}$-$Xaa_{13}$-$Xaa_{14}$-$Xaa_{15}$-$Xaa_{16}$-$Xaa_{17}$-

$Xaa_{18}$-Abu-$Xaa_{20}$-$Xaa_{21}$-$Xaa_{22}$-$Xaa_{23}$-$Xaa_{24}$-$Xaa_{25}$-

$Xaa_{26}$-$Xaa_{27}$-$Xaa_{28}$-$Xaa_{29}$-$Xaa_{30}$-$Xaa_{31}$-$Xaa_{32}$-$Xaa_{33}$-

$Xaa_{34}$-$Xaa_{35}$-$Xaa_{36}$-$Xaa_{37}$-$Xaa_{38}$-$Xaa_{39}$-$Xaa_{40}$ wherein:

$Xaa_1$ is: His, dH, or is absent;
$Xaa_2$ is: dA, Ser, Val, Gly, Thr, Leu, dS, Pro, or Aib;
$Xaa_3$ is: Asp or Glu;
$Xaa_4$ is: Ala, Ile, Tyr, Phe, Val, Thr, Leu, Trp, Gly, dA, Aib, or NMeA;
$Xaa_5$ is: Val, Leu, Phe, Ile, Thr, Trp, Tyr, dV, Aib, or NMeV;
$Xaa_6$ is: Phe, Ile, Leu, Thr, Val, Trp, or Tyr;
$Xaa_8$ is: Asp or Glu;
$Xaa_9$ is: Asn or Gln;
$Xaa_{10}$ is: Tyr or Tyr(OMe);
$Xaa_{12}$ is: Arg, Lys, hR, or Orn;
$Xaa_{13}$ is: Leu, Phe, Glu, Ala, Aib, Ser, Cys, Lys, or K(CO(CH$_2$)$_2$SH);
$Xaa_{14}$ is: Arg, Leu, Lys, Ala, hR, Orn, Gln, Aib, or Cit;
$Xaa_{15}$ is: Lys, Arg, Orn, or Aib;
$Xaa_{16}$ is: Gln or Lys;
$Xaa_{17}$ is: Val, Ala, Leu, Ile, Nle, or Lys;
$Xaa_{18}$ is: Ala, Ser, Cys, Lys, K(CO(CH$_2$)$_2$SH), K(W), Abu, or Nle;
$Xaa_{20}$ is: Lys, Gln, Arg, Ala, Aib, Leu, or Val;
$Xaa_{21}$ is: Lys, Arg, Ala, Aib, Gln, or Orn;
$Xaa_{22}$ is: Tyr, Trp, Phe, Thr, Leu, Ile, Val, Tyr(OMe), Ala, Aib, Ser, Cys, Lys, K(W), or K(CO(CH$_2$)$_2$SH);
$Xaa_{23}$ is: Leu or Aib;
$Xaa_{24}$ is: Gln, Glu, Asn, Ser, Cys, Lys, K(CO(CH$_2$)$_2$SH), or K(W);
$Xaa_{25}$ is: Ser or Aib;
$Xaa_{26}$ is: Ile, Leu, Thr, Val, Trp, Tyr, Phe, Aib, Ser, Cys, Lys, K(CO(CH$_2$)$_2$SH), or K(W);
$Xaa_{27}$ is: Lys, hR, Arg, or Orn;
$Xaa_{28}$ is: Asn, Gln, Lys, Aib, Orn, hR, or Pro;

Xaa$_{29}$ is: Lys, hR, Orn, or is absent;
Xaa$_{30}$ is: Arg, Lys, Ile, Ala, Asp, Glu, Phe, Gly, His, Leu, Met, Asn, Pro, Gln, Ser, Thr, Val, Trp, Tyr, Cys, hR, Cit, Aib, Orn, K(W), K(CO(CH$_2$)$_2$SH), or is absent;
Xaa$_{31}$ is: Tyr, His, Phe, Thr, Cys, Ser, Lys, Gln, K(W), K(CO(CH$_2$)$_2$SH), or is absent;
Xaa$_{32}$ is: Ser, Cys, Lys, or is absent;
Xaa$_{33}$ is: Trp or is absent;
Xaa$_{34}$ is: Cys or is absent;
Xaa$_{35}$ is: Glu or is absent;
Xaa$_{36}$ is: Pro or is absent;
Xaa$_{37}$ is: Gly or is absent;
Xaa$_{38}$ is: Trp or is absent;
Xaa$_{39}$ is: Cys or is absent; and
Xaa$_{40}$ is: Arg or is absent
wherein if Xaa$_{29}$, Xaa$_{30}$, Xaa$_{31}$, Xaa$_{32}$, Xaa$_{33}$, Xaa$_{34}$, Xaa$_{35}$, Xaa$_{36}$, Xaa$_{37}$, Xaa$_{38}$, or Xaa$_{39}$ is absent, the next amino acid present downstream is the next amino acid in said peptide agonist sequence,
and a C-terminal extension wherein the N-terminus of said C-terminal extension is linked to the C-terminus of said peptide of Formula 4 and wherein said C-terminal extension comprises an amino acid sequence of the formula:

```
Formula 3
                                        (SEQ ID NO: 3)
Xaa1-Xaa2-Xaa3-Xaa4-Xaa5-Xaa6-Xaa7-Xaa8-Xaa9-

Xaa10-Xaa11-Xaa12
``` wherein:
Xaa$_1$ is: Gly;
Xaa$_2$ is: Gly;
Xaa$_3$ is: Pro;
Xaa$_4$ is: Ser;
Xaa$_5$ is: Ser;
Xaa$_6$ is: Gly;
Xaa$_7$ is: Ala;
Xaa$_8$ is: Pro;
Xaa$_9$ is: Pro;
Xaa$_{10}$ is: Pro;
Xaa$_{11}$ is: Cys; and
Xaa$_{12}$ is: Cys;
wherein the C-terminal amino acid may be amidated,
and wherein, said peptide agonist comprises at least one Cys residue which is covalently attached to a PEG molecule.

2. The PEGylated VPAC2 receptor peptide agonist according to claim 1, wherein Xaa$_{14}$, Xaa$_{15}$, Xaa$_{20}$, Xaa$_{21}$, Xaa$_{23}$, or Xaa$_{25}$ is Aib.

3. The PEGylated VPAC2 receptor peptide agonist according to claim 2, wherein Xaa$_{15}$, Xaa$_{20}$, Xaa$_{23}$, and Xaa$_{25}$ are Aib.

4. The PEGylated VPAC2 receptor peptide agonist according to claim 3, wherein Xaa$_{12}$, Xaa$_{21}$, Xaa$_{27}$, and Xaa$_{28}$ are Orn.

5. A pharmaceutical composition, comprising a PEGylated VPAC2 receptor peptide agonist according to claim 4, and one or more pharmaceutically acceptable diluents, carriers or excipients.

6. A method of treating non-insulin dependent or insulin dependent diabetes in a patient in need thereof, comprising administering to said patient an effective amount of a PEGylated VPAC2 receptor peptide agonist according to claim 4.

* * * * *

SEQUENCE LISTING

```
<160> NUMBER OF SEQ ID NOS: 148

<210> SEQ ID NO 1
<211> LENGTH: 13
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MISC_FEATURE
<222> LOCATION: (1)..(12)
<223> OTHER INFORMATION: Any Xaa may be independently present or absent.
      If an Xaa is absent, the next amino acid present downstream is the
      next amino acid in the C-terminal extension.
<220> FEATURE:
<221> NAME/KEY: MISC_FEATURE
<222> LOCATION: (1)..(1)
<223> OTHER INFORMATION: Xaa may be present or absent. If present, Xaa
      is Gly, Cys, Lys, K(W), or K(CO(CH2)2SH)
<220> FEATURE:
<221> NAME/KEY: MISC_FEATURE
<222> LOCATION: (2)..(2)
<223> OTHER INFORMATION: Xaa may be present or absent. If present, Xaa
      is Gly, Arg, Cys, Lys, K(W), or K(CO(CH2)2SH)
<220> FEATURE:
<221> NAME/KEY: MISC_FEATURE
<222> LOCATION: (3)..(3)
<223> OTHER INFORMATION: Xaa may be present or absent. If present, Xaa
      is Pro, Thr, Ser, Ala, Cys, Lys, K(W), or K(CO(CH2)2SH)
<220> FEATURE:
<221> NAME/KEY: MISC_FEATURE
<222> LOCATION: (4)..(4)
<223> OTHER INFORMATION: Xaa may be present or absent. If present, Xaa
      is Ser, Pro, His, Cys, Lys, K(W), or K(CO(CH2)2SH)
<220> FEATURE:
<221> NAME/KEY: MISC_FEATURE
<222> LOCATION: (5)..(5)
<223> OTHER INFORMATION: Xaa may be present or absent. If present, Xaa
      is Ser, Arg, Thr, Trp, Lys, Cys, K(W), or K(CO(CH2)2SH)
<220> FEATURE:
<221> NAME/KEY: MISC_FEATURE
<222> LOCATION: (6)..(6)
<223> OTHER INFORMATION: Xaa may be present or absent. If present, Xaa
      is Gly, Ser, Cys, Lys, K(W), or K(CO(CH2)2SH)
<220> FEATURE:
<221> NAME/KEY: MISC_FEATURE
<222> LOCATION: (7)..(7)
<223> OTHER INFORMATION: Xaa may be present or absent. If present, Xaa
      is Ala, Asp, Arg, Glu, Lys, Gly, Cys, K(W), or K(CO(CH2)2SH)
<220> FEATURE:
<221> NAME/KEY: MISC_FEATURE
<222> LOCATION: (8)..(8)
<223> OTHER INFORMATION: Xaa may be present or absent. If present, Xaa
      is Pro, Ser, Ala, Cys, Lys, K(W), or K(CO(CH2)2SH)
<220> FEATURE:
<221> NAME/KEY: MISC_FEATURE
```

```
<222> LOCATION: (9)..(9)
<223> OTHER INFORMATION: Xaa may be present or absent. If present, Xaa
      is Pro, Ser, Ala, Cys, Lys, K(W), or K(CO(CH2)2SH)
<220> FEATURE:
<221> NAME/KEY: MISC_FEATURE
<222> LOCATION: (10)..(10)
<223> OTHER INFORMATION: Xaa may be present or absent. If present, Xaa
      is Pro, Ser, Ala, Arg, Lys, His, Cys, K(W), or K(CO(CH2)2SH)
<220> FEATURE:
<221> NAME/KEY: MISC_FEATURE
<222> LOCATION: (11)..(11)
<223> OTHER INFORMATION: Xaa may be present or absent. If present, Xaa
      is Ser, Cys, His, Pro, Lys, Arg, K(W), or K(CO(CH2)2SH)
<220> FEATURE:
<221> NAME/KEY: MISC_FEATURE
<222> LOCATION: (12)..(12)
<223> OTHER INFORMATION: Xaa may be present or absent. If present, Xaa
      is His, Ser, Arg, Lys, Cys, K(W), or K(CO(CH2)2SH)
<220> FEATURE:
<221> NAME/KEY: MOD_RES
<222> LOCATION: (13)..(13)
<223> OTHER INFORMATION: C-terminal amino acid may be amidated
<220> FEATURE:
<221> NAME/KEY: MISC_FEATURE
<222> LOCATION: (13)..(13)
<223> OTHER INFORMATION: Xaa may be present or absent. If present, Xaa
      is His, Ser, Arg, Lys, Cys, K(W), or K(CO(CH2)2SH)

<400> SEQUENCE: 1

Xaa Xaa Xaa Xaa Xaa Xaa Xaa Xaa Xaa Xaa Xaa Xaa Xaa
1               5                   10

<210> SEQ ID NO 2
<211> LENGTH: 13
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MISC_FEATURE
<222> LOCATION: (1)..(12)
<223> OTHER INFORMATION: Any Xaa may be independently present or absent.
      If an Xaa is absent, the next amino acid present downstream is the
      next amino acid in the C-terminal extension.
<220> FEATURE:
<221> NAME/KEY: MISC_FEATURE
<222> LOCATION: (1)..(1)
<223> OTHER INFORMATION: Xaa may be present or absent. If present, Xaa
      is Gly, Cys, or Lys
<220> FEATURE:
<221> NAME/KEY: MISC_FEATURE
<222> LOCATION: (2)..(2)
<223> OTHER INFORMATION: Xaa may be present or absent. If present, Xaa
      is Gly, Arg, Cys, or Lys
<220> FEATURE:
<221> NAME/KEY: MISC_FEATURE
<222> LOCATION: (3)..(3)
<223> OTHER INFORMATION: Xaa may be present or absent. If present, Xaa
      is Pro, Thr, Ser, Ala, Cys, or Lys
<220> FEATURE:
<221> NAME/KEY: MISC_FEATURE
<222> LOCATION: (4)..(4)
<223> OTHER INFORMATION: Xaa may be present or absent. If present, Xaa
      is Ser, Pro, His, Cys, or Lys
<220> FEATURE:
<221> NAME/KEY: MISC_FEATURE
<222> LOCATION: (5)..(5)
<223> OTHER INFORMATION: Xaa may be present or absent. If present, Xaa
      is Ser, Arg, Thr, Trp, Lys, or Cys
<220> FEATURE:
<221> NAME/KEY: MISC_FEATURE
<222> LOCATION: (6)..(6)
<223> OTHER INFORMATION: Xaa may be present or absent. If present, Xaa
      is Gly, Ser, Cys, or Lys
<220> FEATURE:
<221> NAME/KEY: MISC_FEATURE
```

```
<222> LOCATION: (7)..(7)
<223> OTHER INFORMATION: Xaa may be present or absent. If present, Xaa
      is Ala, Asp, Arg, Glu, Lys, Gly, or Cys
<220> FEATURE:
<221> NAME/KEY: MISC_FEATURE
<222> LOCATION: (8)..(8)
<223> OTHER INFORMATION: Xaa may be present or absent. If present, Xaa
      is Pro, Ser, Ala, Cys, or Lys
<220> FEATURE:
<221> NAME/KEY: MISC_FEATURE
<222> LOCATION: (9)..(9)
<223> OTHER INFORMATION: Xaa may be present or absent. If present, Xaa
      is Pro, Ser, Ala, Cys, or Lys
<220> FEATURE:
<221> NAME/KEY: MISC_FEATURE
<222> LOCATION: (10)..(10)
<223> OTHER INFORMATION: Xaa may be present or absent. If present, Xaa
      is Pro, Ser, Ala, Arg, Lys, His, or Cys
<220> FEATURE:
<221> NAME/KEY: MISC_FEATURE
<222> LOCATION: (11)..(11)
<223> OTHER INFORMATION: Xaa may be present or absent. If present, Xaa
      is Ser, Cys, His, Pro, Lys, or Arg
<220> FEATURE:
<221> NAME/KEY: MISC_FEATURE
<222> LOCATION: (12)..(12)
<223> OTHER INFORMATION: Xaa may be present or absent. If present, Xaa
      is His, Ser, Arg, Lys, or Cys
<220> FEATURE:
<221> NAME/KEY: MOD_RES
<222> LOCATION: (13)..(13)
<223> OTHER INFORMATION: C-terminal amino acid may be amidated
<220> FEATURE:
<221> NAME/KEY: MISC_FEATURE
<222> LOCATION: (13)..(13)
<223> OTHER INFORMATION: Xaa may be present or absent. If present, Xaa
      is His, Ser, Arg, Lys, or Cys

<400> SEQUENCE: 2

Xaa Xaa Xaa Xaa Xaa Xaa Xaa Xaa Xaa Xaa Xaa Xaa Xaa
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MISC_FEATURE
<222> LOCATION: (1)..(11)
<223> OTHER INFORMATION: Any Xaa may be independently present or absent.
      If an Xaa is absent, the next amino acid present downstream is the
      next amino acid in the C-terminal extension.
<220> FEATURE:
<221> NAME/KEY: MISC_FEATURE
<222> LOCATION: (1)..(1)
<223> OTHER INFORMATION: Xaa may be present or absent. If present, Xaa
      is Gly or Cys
<220> FEATURE:
<221> NAME/KEY: MISC_FEATURE
<222> LOCATION: (2)..(2)
<223> OTHER INFORMATION: Xaa may be present or absent. If present, Xaa
      is Gly or Arg
<220> FEATURE:
<221> NAME/KEY: MISC_FEATURE
<222> LOCATION: (3)..(3)
<223> OTHER INFORMATION: Xaa may be present or absent. If present, Xaa
      is Pro or Thr
<220> FEATURE:
<221> NAME/KEY: MISC_FEATURE
<222> LOCATION: (4)..(4)
<223> OTHER INFORMATION: Xaa may be present or absent. If present, Xaa
      is Ser
<220> FEATURE:
<221> NAME/KEY: MISC_FEATURE
```

```
<222> LOCATION: (5)..(5)
<223> OTHER INFORMATION: Xaa may be present or absent. If present, Xaa
      is Ser
<220> FEATURE:
<221> NAME/KEY: MISC_FEATURE
<222> LOCATION: (6)..(6)
<223> OTHER INFORMATION: Xaa may be present or absent. If present, Xaa
      is Gly
<220> FEATURE:
<221> NAME/KEY: MISC_FEATURE
<222> LOCATION: (7)..(7)
<223> OTHER INFORMATION: Xaa may be present or absent. If present, Xaa
      is Ala
<220> FEATURE:
<221> NAME/KEY: MISC_FEATURE
<222> LOCATION: (8)..(8)
<223> OTHER INFORMATION: Xaa may be present or absent. If present, Xaa
      is Pro
<220> FEATURE:
<221> NAME/KEY: MISC_FEATURE
<222> LOCATION: (9)..(9)
<223> OTHER INFORMATION: Xaa may be present or absent. If present, Xaa
      is Pro
<220> FEATURE:
<221> NAME/KEY: MISC_FEATURE
<222> LOCATION: (10)..(10)
<223> OTHER INFORMATION: Xaa may be present or absent. If present, Xaa
      is Pro
<220> FEATURE:
<221> NAME/KEY: MISC_FEATURE
<222> LOCATION: (11)..(11)
<223> OTHER INFORMATION: Xaa may be present or absent. If present, Xaa
      is Ser or Cys
<220> FEATURE:
<221> NAME/KEY: MOD_RES
<222> LOCATION: (12)..(12)
<223> OTHER INFORMATION: C-terminal amino acid may be amidated
<220> FEATURE:
<221> NAME/KEY: MISC_FEATURE
<222> LOCATION: (12)..(12)
<223> OTHER INFORMATION: Xaa may be present or absent. If present, Xaa
      is Cys

<400> SEQUENCE: 3

Xaa Xaa Xaa Xaa Xaa Xaa Xaa Xaa Xaa Xaa Xaa Xaa
1               5                   10

<210> SEQ ID NO 4
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MISC_FEATURE
<222> LOCATION: (1)..(1)
<223> OTHER INFORMATION: Xaa may be present or absent. If present, Xaa
      is His, or dHis
<220> FEATURE:
<221> NAME/KEY: MISC_FEATURE
<222> LOCATION: (2)..(2)
<223> OTHER INFORMATION: Xaa is dAla, Ser, Val, Gly, Thr, Leu, dSer,
      Pro, or Aib
<220> FEATURE:
<221> NAME/KEY: MISC_FEATURE
<222> LOCATION: (3)..(3)
<223> OTHER INFORMATION: Xaa is Asp or Glu
<220> FEATURE:
<221> NAME/KEY: MISC_FEATURE
<222> LOCATION: (4)..(4)
<223> OTHER INFORMATION: Xaa is Ala, Ile, Tyr, Phe, Val, Thr, Leu, Trp,
      Gly, dAla, Aib, or N- methyl alanine
<220> FEATURE:
<221> NAME/KEY: MISC_FEATURE
<222> LOCATION: (5)..(5)
<223> OTHER INFORMATION: Xaa is Val, Leu, Phe, Ile, Thr, Trp, Tyr, dVal,
```

-continued

```
      Aib, or N-methyl valine
<220> FEATURE:
<221> NAME/KEY: MISC_FEATURE
<222> LOCATION: (6)..(6)
<223> OTHER INFORMATION: Xaa is Phe, Ile, Leu, Thr, Val, Trp, or Tyr
<220> FEATURE:
<221> NAME/KEY: MISC_FEATURE
<222> LOCATION: (8)..(8)
<223> OTHER INFORMATION: Xaa is Asp, Glu, Ala, Lys, Leu, Arg, or Tyr
<220> FEATURE:
<221> NAME/KEY: MISC_FEATURE
<222> LOCATION: (9)..(9)
<223> OTHER INFORMATION: Xaa is Asn, Gln, Asp, Glu, Ser, Cys, Lys, or
      K(CO(CH2)2SH)
<220> FEATURE:
<221> NAME/KEY: MISC_FEATURE
<222> LOCATION: (10)..(10)
<223> OTHER INFORMATION: Xaa is Tyr, Trp, Tyr(OMe), Ser, Cys, or Lys
<220> FEATURE:
<221> NAME/KEY: MISC_FEATURE
<222> LOCATION: (12)..(12)
<223> OTHER INFORMATION: Xaa is Arg, Lys, Glu, hR, Orn, Lys (isopropyl),
      Aib, Cit, Ala, Leu, Gln, Phe, Ser, or Cys
<220> FEATURE:
<221> NAME/KEY: MISC_FEATURE
<222> LOCATION: (13)..(13)
<223> OTHER INFORMATION: Xaa is Leu, Phe, Glu, Ala, Aib, Ser, Cys, Lys,
      or K(CO(CH2)2SH)
<220> FEATURE:
<221> NAME/KEY: MISC_FEATURE
<222> LOCATION: (14)..(14)
<223> OTHER INFORMATION: Xaa is Arg, Leu, Lys, Ala, hR, Orn, Lys
      (isopropyl), Phe, Gln, Aib, Cit, Ser, or Cys
<220> FEATURE:
<221> NAME/KEY: MISC_FEATURE
<222> LOCATION: (15)..(15)
<223> OTHER INFORMATION: Xaa is Lys, Ala, Arg, Glu, Leu, hR, Orn, Lys
      (isopropyl), Phe, Gln, Aib, K(Ac), Cit, Ser, Cys, K(W), or
      K(CO(CH2)2SH)
<220> FEATURE:
<221> NAME/KEY: MISC_FEATURE
<222> LOCATION: (16)..(16)
<223> OTHER INFORMATION: Xaa is Gln, Lys, Glu, Ala, hR, Orn, Lys
      (isopropyl), Cit, Ser, Cys, K(CO(CH2)2SH), or K(W)
<220> FEATURE:
<221> NAME/KEY: MISC_FEATURE
<222> LOCATION: (17)..(17)
<223> OTHER INFORMATION: Xaa is Val, Ala, Leu, Ile, Met, Nle, Lys, Aib,
      Ser, Cys, K(CO(CH2)2SH), or K(W)
<220> FEATURE:
<221> NAME/KEY: MISC_FEATURE
<222> LOCATION: (18)..(18)
<223> OTHER INFORMATION: Xaa is Ala, Ser, Cys, Lys, K(CO(CH2)2SH), K(W),
      Abu, or Nle
<220> FEATURE:
<221> NAME/KEY: MOD_RES
<222> LOCATION: (19)..(19)
<223> OTHER INFORMATION: Abu
<220> FEATURE:
<221> NAME/KEY: MISC_FEATURE
<222> LOCATION: (20)..(20)
<223> OTHER INFORMATION: Xaa is Lys, Gln, hR, Arg, Ser, His, Orn, Lys
      (isopropyl), Ala, Aib, Trp, Thr, Leu, Ile, Phe, Tyr, Val, K(Ac),
      Cit, Cys, K(CO(CH2)2SH), or K(W)
<220> FEATURE:
<221> NAME/KEY: MISC_FEATURE
<222> LOCATION: (21)..(21)
<223> OTHER INFORMATION: Xaa is Lys, His, Arg, Ala, Phe, Aib, Leu, Gln,
      Orn, hR, K(Ac), Cit, Ser, Cys, Val, Tyr, Ile, Thr, Trp, K(W), or
      K(CO(CH2)2SH)
<220> FEATURE:
<221> NAME/KEY: MISC_FEATURE
<222> LOCATION: (22)..(22)
<223> OTHER INFORMATION: Xaa is Tyr, Trp, Phe, Thr, Leu, Ile, Val,
      Tyr(OMe), Ala, Aib, Ser, Cys, Lys, K(W), or K(CO(CH2)2SH)
<220> FEATURE:
<221> NAME/KEY: MISC_FEATURE
<222> LOCATION: (23)..(23)
<223> OTHER INFORMATION: Xaa is Leu, Phe, Ile, Ala, Trp, Thr, Val, Aib,
```

```
        Ser, Cys, Lys, K(W), or K(CO(CH2)2SH)
<220> FEATURE:
<221> NAME/KEY: MISC_FEATURE
<222> LOCATION: (24)..(24)
<223> OTHER INFORMATION: Xaa is Gln, Glu, Asn, Ser, Cys, Lys,
        K(CO(CH2)2SH), or K(W)
<220> FEATURE:
<221> NAME/KEY: MISC_FEATURE
<222> LOCATION: (25)..(25)
<223> OTHER INFORMATION: Xaa is Ser, Asp, Phe, Ile, Leu, Thr, Val, Trp,
        Gln, Asn, Tyr, Aib, Glu, Cys, Lys, K(CO(CH2)2SH), or K(W)
<220> FEATURE:
<221> NAME/KEY: MISC_FEATURE
<222> LOCATION: (26)..(26)
<223> OTHER INFORMATION: Xaa is Ile, Leu, Thr, Val, Trp, Tyr, Phe, Aib,
        Ser, Cys, Lys, K(CO(CH2)2SH), or K(W)
<220> FEATURE:
<221> NAME/KEY: MISC_FEATURE
<222> LOCATION: (27)..(27)
<223> OTHER INFORMATION: Xaa is Lys, hR, Arg, Gln, Ala, Asp, Glu, Phe,
        Gly, His, Ile, Met, Asn, Pro, Ser, Thr, Val, Trp, Tyr, Lys
        (isopropyl), Cys, Leu, Orn, dLys, K(W), or K(CO(CH2)2SH)
<220> FEATURE:
<221> NAME/KEY: MISC_FEATURE
<222> LOCATION: (28)..(28)
<223> OTHER INFORMATION: Xaa is Asn, Asp, Gln, Lys, Arg, Aib, Orn, hR,
        Cit, Pro, dLys, Ser, Cys, K(CO(CH2)2SH), or K(W)
<220> FEATURE:
<221> NAME/KEY: MISC_FEATURE
<222> LOCATION: (29)..(39)
<223> OTHER INFORMATION: Any Xaa may be independently present or absent.
        If an Xaa is absent, the next amino acid present downstream is the
        next amino acid in the peptide agonist sequence.
<220> FEATURE:
<221> NAME/KEY: MISC_FEATURE
<222> LOCATION: (29)..(29)
<223> OTHER INFORMATION: Xaa may be present or absent. If present, Xaa
        is Lys, Ser, Arg, Asn, hR, Ala, Asp, Glu, Phe, Gly, His, Ile, Leu,
        Met, Pro, Gln, Thr, Val, Trp, Tyr, Cys, Orn, Cit, Aib, K(W), or
        K(CO(CH2)2SH)
<220> FEATURE:
<221> NAME/KEY: MISC_FEATURE
<222> LOCATION: (30)..(30)
<223> OTHER INFORMATION: Xaa may be present or absent. If present, Xaa
        is Arg, Lys, Ile, Ala, Asp, Glu, Phe, Gly, His, Leu, Met, Asn,
        Pro, Gln, Ser, Thr, Val, Trp, Tyr, Cys, hR, Cit, Aib, Orn, K(W),
        or K(CO(CH2)2SH)
<220> FEATURE:
<221> NAME/KEY: MISC_FEATURE
<222> LOCATION: (31)..(31)
<223> OTHER INFORMATION: Xaa may be present or absent. If present, Xaa
        is Tyr, His, Phe, Thr, Cys, Ser, Lys, Gln, K(W), or K(CO(CH2)2SH)
<220> FEATURE:
<221> NAME/KEY: MISC_FEATURE
<222> LOCATION: (32)..(32)
<223> OTHER INFORMATION: Xaa may be present or absent. If present, Xaa
        is Ser, Cys, or Lys
<220> FEATURE:
<221> NAME/KEY: MISC_FEATURE
<222> LOCATION: (33)..(33)
<223> OTHER INFORMATION: Xaa may be present or absent. If present, Xaa
        is Trp
<220> FEATURE:
<221> NAME/KEY: MISC_FEATURE
<222> LOCATION: (34)..(34)
<223> OTHER INFORMATION: Xaa may be present or absent. If present, Xaa
        is Cys
<220> FEATURE:
<221> NAME/KEY: MISC_FEATURE
<222> LOCATION: (35)..(35)
<223> OTHER INFORMATION: Xaa may be present or absent. If present, Xaa
        is Glu
<220> FEATURE:
<221> NAME/KEY: MISC_FEATURE
<222> LOCATION: (36)..(36)
<223> OTHER INFORMATION: Xaa may be present or absent. If present, Xaa
        is Pro
<220> FEATURE:
<221> NAME/KEY: MISC_FEATURE
```

```
<222> LOCATION: (37)..(37)
<223> OTHER INFORMATION: Xaa may be present or absent. If present, Xaa
      is Gly
<220> FEATURE:
<221> NAME/KEY: MISC_FEATURE
<222> LOCATION: (38)..(38)
<223> OTHER INFORMATION: Xaa may be present or absent. If present, Xaa
      is Trp
<220> FEATURE:
<221> NAME/KEY: MISC_FEATURE
<222> LOCATION: (39)..(39)
<223> OTHER INFORMATION: Xaa may be present or absent. If present, Xaa
      is Cys
<220> FEATURE:
<221> NAME/KEY: MISC_FEATURE
<222> LOCATION: (40)..(40)
<223> OTHER INFORMATION: Xaa may be present or absent. If present, Xaa
      is Arg

<400> SEQUENCE: 4

Xaa Xaa Xaa Xaa Xaa Xaa Thr Xaa Xaa Xaa Thr Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa
            35                  40

<210> SEQ ID NO 5
<211> LENGTH: 11
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist

<400> SEQUENCE: 5

Gly Gly Pro Ser Ser Gly Ala Pro Pro Pro Ser
1               5                   10

<210> SEQ ID NO 6
<211> LENGTH: 11
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MOD_RES
<222> LOCATION: (11)..(11)
<223> OTHER INFORMATION: AMIDATION

<400> SEQUENCE: 6

Gly Gly Pro Ser Ser Gly Ala Pro Pro Pro Ser
1               5                   10

<210> SEQ ID NO 7
<211> LENGTH: 11
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist

<400> SEQUENCE: 7

Gly Gly Pro Ser Ser Gly Ala Pro Pro Pro Cys
1               5                   10

<210> SEQ ID NO 8
<211> LENGTH: 11
```

```
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MOD_RES
<222> LOCATION: (11)..(11)
<223> OTHER INFORMATION: AMIDATION

<400> SEQUENCE: 8

Gly Gly Pro Ser Ser Gly Ala Pro Pro Pro Cys
1               5                   10

<210> SEQ ID NO 9
<211> LENGTH: 11
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist

<400> SEQUENCE: 9

Gly Arg Pro Ser Ser Gly Ala Pro Pro Pro Ser
1               5                   10

<210> SEQ ID NO 10
<211> LENGTH: 11
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MOD_RES
<222> LOCATION: (11)..(11)
<223> OTHER INFORMATION: AMIDATION

<400> SEQUENCE: 10

Gly Arg Pro Ser Ser Gly Ala Pro Pro Pro Ser
1               5                   10

<210> SEQ ID NO 11
<211> LENGTH: 12
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist

<400> SEQUENCE: 11

Gly Gly Pro Ser Ser Gly Ala Pro Pro Pro Cys Cys
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MOD_RES
<222> LOCATION: (12)..(12)
<223> OTHER INFORMATION: AMIDATION

<400> SEQUENCE: 12

Gly Gly Pro Ser Ser Gly Ala Pro Pro Pro Cys Cys
1               5                   10
```

```
<210> SEQ ID NO 13
<211> LENGTH: 10
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MISC_FEATURE
<222> LOCATION: (1)..(9)
<223> OTHER INFORMATION: Any Xaa may be independently present or absent.
      If an Xaa is absent, it is preferred that the next amino acid
      present downstream is the next amino acid in the C-terminal
      extension.
<220> FEATURE:
<221> NAME/KEY: MISC_FEATURE
<222> LOCATION: (1)..(1)
<223> OTHER INFORMATION: Xaa may be present or absent. If present, Xaa
      is Ser, Cys, Lys, K(W) or K(CO(CH2)2SH)
<220> FEATURE:
<221> NAME/KEY: MISC_FEATURE
<222> LOCATION: (2)..(2)
<223> OTHER INFORMATION: Xaa may be present or absent. If present, Xaa
      is Arg, Ser, hR, Orn, His, Cys, Lys, K(W) or K(CO(CH2)2SH)
<220> FEATURE:
<221> NAME/KEY: MISC_FEATURE
<222> LOCATION: (3)..(3)
<223> OTHER INFORMATION: Xaa may be present or absent. If present, Xaa
      is Thr, Cys, Lys, K(W) or K(CO(CH2)2SH)
<220> FEATURE:
<221> NAME/KEY: MISC_FEATURE
<222> LOCATION: (4)..(4)
<223> OTHER INFORMATION: Xaa may be present or absent. If present, Xaa
      is Ser, Cys, Lys, K(W) or K(CO(CH2)2SH)
<220> FEATURE:
<221> NAME/KEY: MISC_FEATURE
<222> LOCATION: (5)..(5)
<223> OTHER INFORMATION: Xaa may be present or absent. If present, Xaa
      is Pro, Ser, Ala, Cys, Lys, K(W) or K(CO(CH2)2SH)
<220> FEATURE:
<221> NAME/KEY: MISC_FEATURE
<222> LOCATION: (6)..(6)
<223> OTHER INFORMATION: Xaa may be present or absent. If present, Xaa
      is Pro, Ser, Ala, Arg, Cys, Lys, K(W) or K(CO(CH2)2SH)
<220> FEATURE:
<221> NAME/KEY: MISC_FEATURE
<222> LOCATION: (7)..(7)
<223> OTHER INFORMATION: Xaa may be present or absent. If present, Xaa
      is Pro, Ser, Ala, Cys, Lys, K(W) or K(CO(CH2)2SH)
<220> FEATURE:
<221> NAME/KEY: MISC_FEATURE
<222> LOCATION: (8)..(8)
<223> OTHER INFORMATION: Xaa may be present or absent. If present, Xaa
      is Lys, Pro, Cys, K(W) or K(CO(CH2)2SH)
<220> FEATURE:
<221> NAME/KEY: MISC_FEATURE
<222> LOCATION: (9)..(9)
<223> OTHER INFORMATION: Xaa may be present or absent. If present, Xaa
      is K(E-C16), Ser, Cys, Lys, K(W) or K(CO(CH2)2SH)
<220> FEATURE:
<221> NAME/KEY: MOD_RES
<222> LOCATION: (10)..(10)
<223> OTHER INFORMATION: C-terminal amino acid may be amidated
<220> FEATURE:
<221> NAME/KEY: MISC_FEATURE
<222> LOCATION: (10)..(10)
<223> OTHER INFORMATION: Xaa may be present or absent. If present, Xaa
      is Ser, Cys, Lys, K(W) or K(CO(CH2)2SH)

<400> SEQUENCE: 13

Xaa Xaa Xaa Xaa Xaa Xaa Xaa Xaa Xaa Xaa
1               5                   10

<210> SEQ ID NO 14
<211> LENGTH: 28
<212> TYPE: PRT
```

<213> ORGANISM: Homo sapiens

<400> SEQUENCE: 14

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 15
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION

<400> SEQUENCE: 15

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 16
<211> LENGTH: 37
<212> TYPE: PRT
<213> ORGANISM: Homo sapiens
<220> FEATURE:
<221> NAME/KEY: MOD_RES
<222> LOCATION: (37)..(37)
<223> OTHER INFORMATION: AMIDATION

<400> SEQUENCE: 16

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Gln
            20                  25                  30

Arg Val Lys Asn Lys
        35

<210> SEQ ID NO 17
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES

```
<222> LOCATION: (22)..(22)
<223> OTHER INFORMATION: Methoxy
<220> FEATURE:
<221> NAME/KEY: MOD_RES
<222> LOCATION: (28)..(28)
<223> OTHER INFORMATION: Aib
<220> FEATURE:
<221> NAME/KEY: MOD_RES
<222> LOCATION: (29)..(29)
<223> OTHER INFORMATION: Orn

<400> SEQUENCE: 17

His Ser Asp Ala Val Phe Thr Glu Gln Tyr Thr Arg Xaa Arg Xaa Gln
1               5                   10                  15

Leu Ala Ala Xaa Xaa Tyr Leu Gln Ser Ile Lys Xaa Xaa
            20                  25

<210> SEQ ID NO 18
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: misc_feature
<222> LOCATION: (9)..(9)
<223> OTHER INFORMATION: Xaa is K(CO(CH2)2SH)
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 18

His Ser Asp Ala Val Phe Thr Glu Xaa Tyr Thr Xaa Leu Arg Xaa Gln
1               5                   10                  15

Val Ala Ala Xaa Xaa Tyr Leu Gln Ser Ile Xaa Xaa
            20                  25

<210> SEQ ID NO 19
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
```

```
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Xaa is K(W)
<220> FEATURE:
<221> NAME/KEY: MOD_RES
<222> LOCATION: (29)..(29)
<223> OTHER INFORMATION: Orn

<400> SEQUENCE: 19

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Xaa
            20                  25

<210> SEQ ID NO 20
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: misc_feature
<222> LOCATION: (21)..(21)
<223> OTHER INFORMATION: Xaa is K(CO(CH2)2SH)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 20

His Ser Asp Ala Val Phe Thr Glu Gln Tyr Thr Xaa Leu Arg Xaa Gln
1               5                   10                  15
```

Val Ala Ala Xaa Xaa Tyr Leu Gln Ser Ile Xaa Xaa
            20                  25

<210> SEQ ID NO 21
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (20)..(20)
<223> OTHER INFORMATION: Xaa is K(CO(CH2)2SH)
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 21

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa
            20                  25

<210> SEQ ID NO 22
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES

```
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 22

His Ser Asp Ala Val Phe Thr Glu Gln Tyr Thr Xaa Leu Arg Xaa Gln
1               5                   10                  15

Val Cys Ala Xaa Xaa Tyr Leu Gln Ser Ile Xaa Xaa
            20                  25

<210> SEQ ID NO 23
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 23

His Ser Asp Ala Val Phe Thr Glu Gln Tyr Thr Xaa Leu Arg Cys Gln
1               5                   10                  15

Val Ala Ala Xaa Xaa Tyr Leu Gln Ser Ile Xaa Xaa
            20                  25

<210> SEQ ID NO 24
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
```

```
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 24

His Ser Asp Ala Val Phe Thr Glu Gln Tyr Thr Xaa Leu Arg Xaa Gln
1               5                   10                  15
Leu Ala Ala Xaa Xaa Tyr Leu Gln Ser Ile Xaa Xaa
            20                  25

<210> SEQ ID NO 25
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 25

His Ser Asp Ala Val Phe Thr Glu Gln Tyr Thr Xaa Leu Arg Xaa Gln
1               5                   10                  15
Val Ala Ala Xaa Xaa Tyr Xaa Gln Ser Ile Xaa Xaa
            20                  25

<210> SEQ ID NO 26
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
```

```
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 26

His Ser Asp Ala Val Phe Thr Glu Gln Tyr Thr Xaa Leu Arg Xaa Gln
1               5                   10                  15

Val Ala Ala Xaa Xaa Tyr Leu Gln Xaa Ile Xaa Xaa
            20                  25

<210> SEQ ID NO 27
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
```

```
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 27

His Ser Asp Ala Val Phe Thr Glu Gln Tyr Thr Xaa Leu Arg Xaa Gln
1               5                   10                  15

Val Ala Xaa Xaa Xaa Tyr Leu Gln Xaa Ile Xaa Xaa
            20                  25

<210> SEQ ID NO 28
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 28

His Ser Asp Ala Val Phe Thr Glu Gln Tyr Thr Xaa Leu Arg Xaa Gln
1               5                   10                  15

Leu Ala Ala Xaa Xaa Tyr Leu Gln Xaa Ile Xaa Xaa
            20                  25

<210> SEQ ID NO 29
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
```

```
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 29

His Ser Asp Ala Val Phe Thr Glu Gln Tyr Thr Xaa Leu Arg Xaa Gln
1               5                   10                  15

Leu Ala Ala Xaa Xaa Tyr Xaa Gln Xaa Ile Xaa Xaa
            20                  25

<210> SEQ ID NO 30
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
```

<221> NAME/KEY: MOD_RES
<222> LOCATION: (28)..(28)
<223> OTHER INFORMATION: Orn

<400> SEQUENCE: 30

His Ser Asp Ala Val Phe Thr Glu Gln Tyr Thr Xaa Leu Arg Xaa Gln
1               5                   10                  15

Leu Ala Xaa Xaa Xaa Tyr Xaa Gln Ser Ile Xaa Xaa
            20                  25

<210> SEQ ID NO 31
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 31

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Xaa
            20                  25

<210> SEQ ID NO 32
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES

```
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 32

His Ser Asp Ala Val Phe Thr Glu Gln Tyr Thr Xaa Leu Arg Xaa Gln
1               5                   10                  15

Leu Ala Xaa Xaa Xaa Tyr Xaa Gln Xaa Ile Xaa Xaa
            20                  25

<210> SEQ ID NO 33
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
```

```
<400> SEQUENCE: 33

His Ser Asp Ala Val Phe Thr Glu Gln Tyr Thr Xaa Leu Arg Xaa Gln
1               5                   10                  15

Leu Ala Ala Xaa Xaa Tyr Xaa Gln Ser Ile Xaa Xaa
            20                  25

<210> SEQ ID NO 34
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Xaa is K(W)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 34

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa
            20                  25

<210> SEQ ID NO 35
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
```

```
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (24)..(24)
<223> OTHER INFORMATION: Xaa is K(W)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 35

His Ser Asp Ala Val Phe Thr Glu Gln Tyr Thr Xaa Leu Arg Xaa Gln
1               5                   10                  15

Val Ala Ala Xaa Xaa Tyr Leu Xaa Ser Ile Xaa Xaa
            20                  25

<210> SEQ ID NO 36
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Xaa is K(W)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 36

His Ser Asp Ala Val Phe Thr Glu Gln Tyr Thr Xaa Leu Arg Xaa Gln
1               5                   10                  15

Xaa Ala Ala Xaa Xaa Tyr Leu Gln Ser Ile Xaa Xaa
            20                  25

<210> SEQ ID NO 37
<211> LENGTH: 28
<212> TYPE: PRT
<213> ORGANISM: Artificial sequence
<220> FEATURE:
```

```
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Xaa is K(CO(CH2)2SH)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 37

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa
            20                  25

<210> SEQ ID NO 38
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: misc_feature
<222> LOCATION: (21)..(21)
<223> OTHER INFORMATION: Xaa is K(W)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 38

His Ser Asp Ala Val Phe Thr Glu Gln Tyr Thr Xaa Leu Arg Xaa Gln
```

```
                1               5                  10                  15
Val Ala Ala Xaa Xaa Tyr Leu Gln Ser Ile Xaa Xaa
            20              25

<210> SEQ ID NO 39
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 39

His Ser Asp Ala Val Phe Thr Glu Gln Tyr Thr Xaa Leu Arg Xaa Gln
1               5                   10                  15

Val Ala Ala Xaa Cys Tyr Leu Gln Ser Ile Xaa Xaa
            20              25

<210> SEQ ID NO 40
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
```

```
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 40

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa
            20                  25

<210> SEQ ID NO 41
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (26)..(26)
<223> OTHER INFORMATION: Xaa is K(W)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 41

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Xaa Xaa Xaa
            20                  25

<210> SEQ ID NO 42
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
```

```
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (29)..(29)
<223> OTHER INFORMATION: Orn

<400> SEQUENCE: 42

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Cys Xaa
            20                  25

<210> SEQ ID NO 43
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
```

```
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 43

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Cys Xaa Xaa
            20                  25

<210> SEQ ID NO 44
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 44

His Ser Asp Ala Val Phe Thr Glu Gln Tyr Thr Xaa Leu Arg Xaa Gln
1               5                   10                  15

Cys Ala Xaa Xaa Xaa Tyr Leu Gln Xaa Ile Xaa Xaa
            20                  25

<210> SEQ ID NO 45
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
```

-continued

```
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 45

His Ser Asp Ala Val Phe Thr Glu Gln Tyr Thr Xaa Leu Arg Cys Gln
1               5                   10                  15

Leu Ala Xaa Xaa Xaa Tyr Leu Gln Xaa Ile Xaa Xaa
            20                  25

<210> SEQ ID NO 46
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: misc_feature
<222> LOCATION: (21)..(21)
<223> OTHER INFORMATION: Xaa is K(WPEG40K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
```

```
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 46

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Ser
        35

<210> SEQ ID NO 47
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (28)..(28)
<223> OTHER INFORMATION: Aib
<220> FEATURE:
<221> NAME/KEY: MOD_RES
<222> LOCATION: (29)..(29)
<223> OTHER INFORMATION: Orn
<220> FEATURE:
<221> NAME/KEY: MOD_RES
<222> LOCATION: (40)..(40)
<223> OTHER INFORMATION: AMIDATION
<220> FEATURE:
<221> NAME/KEY: misc_feature
<222> LOCATION: (40)..(40)
<223> OTHER INFORMATION: Cys(PEG40K)

<400> SEQUENCE: 47

His Ser Asp Ala Val Phe Thr Glu Gln Tyr Thr Arg Xaa Arg Xaa Gln
1               5                   10                  15

Leu Ala Ala Xaa Xaa Tyr Leu Gln Ser Ile Lys Xaa Xaa Gly Gly Pro
            20                  25                  30

Ser Ser Gly Ala Pro Pro Pro Cys
```

<210> SEQ ID NO 48
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: misc_feature
<222> LOCATION: (9)..(9)
<223> OTHER INFORMATION: Xaa is K(CO(CH2)2SPEG40K)
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 48

His Ser Asp Ala Val Phe Thr Glu Xaa Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 49
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:

```
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Xaa is K(WPEG40K)
<220> FEATURE:
<221> NAME/KEY: MOD_RES
<222> LOCATION: (29)..(29)
<223> OTHER INFORMATION: Orn
<220> FEATURE:
<221> NAME/KEY: MOD_RES
<222> LOCATION: (40)..(40)
<223> OTHER INFORMATION: AMIDATION

<400> SEQUENCE: 49

His Ser Asp Ala Val Phe Thr Glu Gln Tyr Thr Xaa Leu Arg Xaa Gln
 1               5                  10                  15

Val Ala Ala Xaa Xaa Tyr Leu Gln Ser Ile Xaa Xaa Xaa Gly Gly Pro
            20                  25                  30

Ser Ser Gly Ala Pro Pro Pro Ser
        35                  40

<210> SEQ ID NO 50
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: misc_feature
<222> LOCATION: (21)..(21)
<223> OTHER INFORMATION: Cys(PEG40K)
<220> FEATURE:
<221> NAME/KEY: MOD_RES
<222> LOCATION: (27)..(27)
<223> OTHER INFORMATION: Orn
```

```
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 50

His Ser Asp Ala Val Phe Thr Glu Gln Tyr Thr Xaa Leu Arg Xaa Gln
1               5                   10                  15

Val Ala Ala Xaa Cys Tyr Leu Gln Ser Ile Xaa Xaa Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: misc_feature
<222> LOCATION: (21)..(21)
<223> OTHER INFORMATION: Xaa is K(CO(CH2)2SPEG40K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 51

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 52
<211> LENGTH: 39
```

```
<212> TYPE: PRT
<213> ORGANISM: Artificial sequence
<220> FEATURE:
<223> OTHER INFORMATION: Synthetic sequence: PEGylated VPAC2 receptor
      peptide agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: misc_feature
<222> LOCATION: (21)..(21)
<223> OTHER INFORMATION: Xaa is K(CO(CH2)2SPEG20K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 52

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
```

```
<222> LOCATION: (20)..(20)
<223> OTHER INFORMATION: Xaa is K(CO(CH2)2SPEG40K)
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 53

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Ser
        35

<210> SEQ ID NO 54
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (18)..(18)
<223> OTHER INFORMATION: Cys(PEG40K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION
```

```
<400> SEQUENCE: 54

His Ser Asp Ala Val Phe Thr Glu Gln Tyr Thr Xaa Leu Arg Xaa Gln
1               5                   10                  15

Val Cys Ala Xaa Xaa Tyr Leu Gln Ser Ile Xaa Xaa Gly Gly Pro Ser
            20                  25                  30

Ser Gly Ala Pro Pro Ser
        35

<210> SEQ ID NO 55
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Cys(PEG40K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 55

His Ser Asp Ala Val Phe Thr Glu Gln Tyr Thr Xaa Leu Arg Cys Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Ser
        35

<210> SEQ ID NO 56
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
```

```
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Xaa is K(CO(CH2)2SPEG40K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 56

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Ser
            35

<210> SEQ ID NO 57
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
```

```
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG40K)
<220> FEATURE:
<221> NAME/KEY: MOD_RES
<222> LOCATION: (39)..(39)
<223> OTHER INFORMATION: AMIDATION

<400> SEQUENCE: 57

His Ser Asp Ala Val Phe Thr Glu Gln Tyr Thr Xaa Leu Arg Xaa Gln
1               5                   10                  15

Val Ala Ala Xaa Xaa Tyr Xaa Gln Ser Ile Xaa Xaa Gly Gly Pro Ser
            20                  25                  30

Ser Gly Ala Pro Pro Pro Cys
        35

<210> SEQ ID NO 58
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG40K)
<220> FEATURE:
<221> NAME/KEY: MOD_RES
```

```
<222> LOCATION: (39)..(39)
<223> OTHER INFORMATION: AMIDATION

<400> SEQUENCE: 58

His Ser Asp Ala Val Phe Thr Glu Gln Tyr Thr Xaa Leu Arg Xaa Gln
1               5                   10                  15

Val Ala Ala Xaa Xaa Tyr Leu Gln Xaa Ile Xaa Xaa Gly Gly Pro Ser
            20                  25                  30

Ser Gly Ala Pro Pro Pro Cys
            35

<210> SEQ ID NO 59
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG40K)
<220> FEATURE:
<221> NAME/KEY: MOD_RES
<222> LOCATION: (39)..(39)
<223> OTHER INFORMATION: AMIDATION

<400> SEQUENCE: 59

His Ser Asp Ala Val Phe Thr Glu Gln Tyr Thr Xaa Leu Arg Xaa Gln
1               5                   10                  15

Val Ala Xaa Xaa Xaa Tyr Leu Gln Xaa Ile Xaa Xaa Gly Gly Pro Ser
            20                  25                  30
```

Ser Gly Ala Pro Pro Cys
        35

<210> SEQ ID NO 60
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 60

His Ser Asp Ala Val Phe Thr Glu Gln Tyr Thr Xaa Leu Arg Xaa Gln
1               5                   10                  15

Leu Ala Ala Xaa Xaa Tyr Xaa Gln Ser Ile Xaa Xaa Gly Gly Pro Ser
                20                  25                  30

Ser Gly Ala Pro Pro Cys Cys
        35                  40

<210> SEQ ID NO 61
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist

```
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 61

His Ser Asp Ala Val Phe Thr Glu Gln Tyr Thr Xaa Leu Arg Xaa Gln
1               5                   10                  15

Leu Ala Ala Xaa Xaa Tyr Leu Gln Xaa Ile Xaa Xaa Gly Gly Pro Ser
            20                  25                  30

Ser Gly Ala Pro Pro Cys Cys
        35                  40

<210> SEQ ID NO 62
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
```

```
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 62

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Gly Gly Pro Ser
            20                  25                  30

Ser Gly Ala Pro Pro Cys Cys
        35              40

<210> SEQ ID NO 63
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
```

```
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 63

His Ser Asp Ala Val Phe Thr Glu Gln Tyr Thr Xaa Leu Arg Xaa Gln
1               5                   10                  15
Leu Ala Ala Xaa Xaa Tyr Xaa Gln Xaa Ile Xaa Xaa Gly Gly Pro Ser
                20                  25                  30
Ser Gly Ala Pro Pro Pro Cys Cys
            35                  40

<210> SEQ ID NO 64
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
```

```
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 64

His Ser Asp Ala Val Phe Thr Glu Gln Tyr Thr Xaa Leu Arg Xaa Gln
1               5                   10                  15

Leu Ala Xaa Xaa Xaa Tyr Xaa Gln Ser Ile Xaa Xaa Gly Gly Pro Ser
            20                  25                  30

Ser Gly Ala Pro Pro Pro Cys Cys
        35                  40

<210> SEQ ID NO 65
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
```

-continued

```
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 65

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Xaa Gly Gly Pro Ser
            20                  25                  30

Ser Gly Ala Pro Pro Pro Cys Cys
        35                  40

<210> SEQ ID NO 66
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
```

```
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 66

His Ser Asp Ala Val Phe Thr Glu Gln Tyr Thr Xaa Leu Arg Xaa Gln
1               5                   10                  15

Leu Ala Xaa Xaa Xaa Tyr Xaa Gln Xaa Ile Xaa Xaa Gly Gly Pro Ser
            20                  25                  30

Ser Gly Ala Pro Pro Pro Cys Cys
        35                  40

<210> SEQ ID NO 67
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Xaa is K(WPEG40K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 67

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Ser
```

<210> SEQ ID NO 68
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (24)..(24)
<223> OTHER INFORMATION: Xaa is K(WPEG40K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 68

His Ser Asp Ala Val Phe Thr Glu Gln Tyr Thr Xaa Leu Arg Xaa Gln
1               5                   10                  15

Val Ala Ala Xaa Xaa Tyr Leu Xaa Ser Ile Xaa Xaa Gly Gly Pro Ser
            20                  25                  30

Ser Gly Ala Pro Pro Pro Ser
            35

<210> SEQ ID NO 69
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:

```
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Xaa is K(WPEG40K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 69

His Ser Asp Ala Val Phe Thr Glu Gln Tyr Thr Xaa Leu Arg Xaa Gln
1               5                   10                  15

Xaa Ala Ala Xaa Xaa Tyr Leu Gln Ser Ile Xaa Xaa Gly Gly Pro Ser
            20                  25                  30

Ser Gly Ala Pro Pro Ser
        35

<210> SEQ ID NO 70
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (26)..(26)
<223> OTHER INFORMATION: Xaa is K(WPEG40K)
```

```
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 70

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Xaa Xaa Xaa Gly Gly Pro Ser
            20                  25                  30

Ser Gly Ala Pro Pro Pro Ser
        35

<210> SEQ ID NO 71
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Cys(PEG40K)
<220> FEATURE:
<221> NAME/KEY: MOD_RES
<222> LOCATION: (29)..(29)
<223> OTHER INFORMATION: Orn
<220> FEATURE:
<221> NAME/KEY: MOD_RES
<222> LOCATION: (40)..(40)
```

<223> OTHER INFORMATION: AMIDATION

<400> SEQUENCE: 71

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Cys Xaa Gly Gly Pro
            20                  25                  30

Ser Ser Gly Ala Pro Pro Pro Ser
        35                  40

<210> SEQ ID NO 72
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: misc_feature
<222> LOCATION: (26)..(26)
<223> OTHER INFORMATION: Cys(PEG40K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 72

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Cys Xaa Xaa Gly Gly Pro Ser
            20                  25                  30

Ser Gly Ala Pro Pro Pro Ser

<210> SEQ ID NO 73
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Cys(PEG40K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 73

```
His Ser Asp Ala Val Phe Thr Glu Gln Tyr Thr Xaa Leu Arg Xaa Gln
1               5                   10                  15

Cys Ala Xaa Xaa Xaa Tyr Leu Gln Xaa Ile Xaa Xaa Gly Gly Pro Ser
            20                  25                  30

Ser Gly Ala Pro Pro Pro Ser
        35
```

<210> SEQ ID NO 74
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor agonist
<220> FEATURE:

```
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Cys(PEG40K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 74

His Ser Asp Ala Val Phe Thr Glu Gln Tyr Thr Xaa Leu Arg Cys Gln
1               5                   10                  15

Leu Ala Xaa Xaa Xaa Tyr Leu Gln Xaa Ile Xaa Xaa Gly Gly Pro Ser
            20                  25                  30

Ser Gly Ala Pro Pro Ser
        35

<210> SEQ ID NO 75
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (13)..(13)
<223> OTHER INFORMATION: Xaa is K(CO(CH2)2SPEG20K)
```

```
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 75

His Ser Asp Ala Val Phe Thr Glu Gln Tyr Thr Xaa Xaa Arg Xaa Gln
 1               5                  10                  15

Val Ala Ala Xaa Xaa Tyr Leu Gln Ser Ile Xaa Xaa Gly Gly Pro Ser
            20                  25                  30

Ser Gly Ala Pro Pro Pro Ser
            35

<210> SEQ ID NO 76
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (24)..(24)
<223> OTHER INFORMATION: Xaa is K(CO(CH2)2SPEG20K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
```

```
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 76

His Ser Asp Ala Val Phe Thr Glu Gln Tyr Thr Xaa Leu Arg Xaa Gln
1               5                   10                  15

Val Ala Ala Xaa Xaa Tyr Leu Xaa Ser Ile Xaa Xaa Gly Gly Pro Ser
            20                  25                  30

Ser Gly Ala Pro Pro Pro Cys
        35

<210> SEQ ID NO 77
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (19)..(19)
<223> OTHER INFORMATION: Xaa is K(CO(CH2)2SPEG20K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 77

His Ser Asp Ala Val Phe Thr Glu Gln Tyr Thr Xaa Leu Arg Xaa Gln
1               5                   10                  15
```

-continued

```
Val Ala Xaa Xaa Xaa Tyr Leu Gln Ser Ile Xaa Xaa Gly Gly Pro Ser
            20                  25                  30

Ser Gly Ala Pro Pro Pro Cys
        35

<210> SEQ ID NO 78
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (25)..(25)
<223> OTHER INFORMATION: Xaa is K(CO(CH2)2SPEG20K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 78

His Ser Asp Ala Val Phe Thr Glu Gln Tyr Thr Xaa Leu Arg Xaa Gln
1               5                   10                  15

Val Ala Ala Xaa Xaa Tyr Leu Gln Xaa Ile Xaa Xaa Gly Gly Pro Ser
            20                  25                  30

Ser Gly Ala Pro Pro Pro Cys
        35

<210> SEQ ID NO 79
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
```

```
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (26)..(26)
<223> OTHER INFORMATION: Xaa is K(CO(CH2)2SPEG20K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 79

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Xaa Xaa Xaa Gly Gly Pro Ser
            20                  25                  30

Ser Gly Ala Pro Pro Pro Cys
        35

<210> SEQ ID NO 80
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
```

```
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Xaa is K(CO(CH2)2SPEG20K)
<220> FEATURE:
<221> NAME/KEY: MOD_RES
<222> LOCATION: (29)..(29)
<223> OTHER INFORMATION: Orn
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 80

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Xaa Gly Gly Pro
            20                  25                  30

Ser Ser Gly Ala Pro Pro Pro Cys
        35                  40

<210> SEQ ID NO 81
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (24)..(24)
<223> OTHER INFORMATION: Cys(PEG20K)
<220> FEATURE:
<221> NAME/KEY: MOD_RES
<222> LOCATION: (27)..(27)
```

```
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 81

His Ser Asp Ala Val Phe Thr Glu Gln Tyr Thr Xaa Leu Arg Xaa Gln
1               5                   10                  15

Val Ala Ala Xaa Xaa Tyr Leu Cys Ser Ile Xaa Xaa Gly Gly Pro Ser
            20                  25                  30

Ser Gly Ala Pro Pro Pro Cys
        35

<210> SEQ ID NO 82
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (26)..(26)
<223> OTHER INFORMATION: Cys(PEG20K)
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 82
```

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Cys Xaa Xaa Gly Gly Pro Ser
            20                  25                  30

Ser Gly Ala Pro Pro Cys
        35

```
<210> SEQ ID NO 83
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Cys(PEG20K)
<220> FEATURE:
<221> NAME/KEY: MOD_RES
<222> LOCATION: (29)..(29)
<223> OTHER INFORMATION: Orn
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 83
```

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Cys Xaa Gly Gly Pro
            20                  25                  30

Ser Ser Gly Ala Pro Pro Cys
        35                  40

```
<210> SEQ ID NO 84
<211> LENGTH: 39
<212> TYPE: PRT
<213> ORGANISM: Artificial sequence
```

```
<220> FEATURE:
<223> OTHER INFORMATION: Synthetic sequence: Reference peptide used for
      percentage sequence identity calculations
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 84

His Ser Asp Ala Val Phe Thr Glu Gln Tyr Thr Xaa Leu Arg Xaa Gln
1               5                   10                  15

Leu Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 85
<211> LENGTH: 7
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist

<400> SEQUENCE: 85

Ser Arg Thr Ser Pro Pro Pro
1               5

<210> SEQ ID NO 86
<211> LENGTH: 7
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MOD_RES
<222> LOCATION: (7)..(7)
<223> OTHER INFORMATION: AMIDATION

<400> SEQUENCE: 86
```

Ser Arg Thr Ser Pro Pro Pro
1               5

<210> SEQ ID NO 87
<211> LENGTH: 10
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist

<400> SEQUENCE: 87

Ser Ser Thr Ser Pro Arg Pro Pro Ser Ser
1               5                   10

<210> SEQ ID NO 88
<211> LENGTH: 10
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MOD_RES
<222> LOCATION: (10)..(10)
<223> OTHER INFORMATION: AMIDATION

<400> SEQUENCE: 88

Ser Ser Thr Ser Pro Arg Pro Pro Ser Ser
1               5                   10

<210> SEQ ID NO 89
<211> LENGTH: 8
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: misc_feature
<222> LOCATION: (8)..(8)
<223> OTHER INFORMATION: Xaa is K(W)

<400> SEQUENCE: 89

Ser Arg Thr Ser Pro Pro Pro Xaa
1               5

<210> SEQ ID NO 90
<211> LENGTH: 8
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: misc_feature
<222> LOCATION: (8)..(8)
<223> OTHER INFORMATION: Xaa is K(W)
<220> FEATURE:
<221> NAME/KEY: MOD_RES
<222> LOCATION: (8)..(8)
<223> OTHER INFORMATION: AMIDATION

<400> SEQUENCE: 90

Ser Arg Thr Ser Pro Pro Pro Xaa
1               5

<210> SEQ ID NO 91
<211> LENGTH: 8

```
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist

<400> SEQUENCE: 91

Ser Arg Thr Ser Pro Pro Pro Cys
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic sequence: C-terminal extension of the
      PEGylated VPAC2 receptor peptide agonist
<220> FEATURE:
<221> NAME/KEY: MOD_RES
<222> LOCATION: (8)..(8)
<223> OTHER INFORMATION: AMIDATION

<400> SEQUENCE: 92

Ser Arg Thr Ser Pro Pro Pro Cys
1               5

<210> SEQ ID NO 93
<211> LENGTH: 9
<212> TYPE: PRT
<213> ORGANISM: Artificial sequence
<220> FEATURE:
<223> OTHER INFORMATION: Synthetic sequence: N-terminal modification to
      the PEGylated VPAC2 receptor peptide agonist

<400> SEQUENCE: 93

Ser Trp Cys Glu Pro Gly Trp Cys Arg
1               5

<210> SEQ ID NO 94
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (18)..(18)
<223> OTHER INFORMATION: Xaa is K(CO(CH2)2SH)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
```

```
<220> FEATURE:
<221> NAME/KEY: MOD_RES
<222> LOCATION: (28)..(28)
<223> OTHER INFORMATION: Orn

<400> SEQUENCE: 94

His Ser Asp Ala Val Phe Thr Glu Gln Tyr Thr Xaa Leu Arg Xaa Gln
1               5                   10                  15

Val Xaa Ala Xaa Xaa Tyr Leu Gln Ser Ile Xaa Xaa
            20                  25

<210> SEQ ID NO 95
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (29)..(29)
<223> OTHER INFORMATION: Orn

<400> SEQUENCE: 95

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Cys Xaa
            20                  25

<210> SEQ ID NO 96
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
```

```
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 96

His Ser Asp Ala Val Phe Thr Glu Gln Tyr Thr Xaa Leu Arg Xaa Gln
1               5                   10                  15
Leu Ala Xaa Xaa Xaa Tyr Leu Gln Ser Cys Xaa Xaa
            20                  25

<210> SEQ ID NO 97
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Xaa is K(CO(CH2)2SH)
<220> FEATURE:
<221> NAME/KEY: MOD_RES
<222> LOCATION: (29)..(29)
```

```
<223> OTHER INFORMATION: Orn

<400> SEQUENCE: 97

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Xaa
            20                  25

<210> SEQ ID NO 98
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Xaa is K(CO(CH2)2SH)
<220> FEATURE:
<221> NAME/KEY: MOD_RES
<222> LOCATION: (29)..(29)
<223> OTHER INFORMATION: Orn

<400> SEQUENCE: 98

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Xaa Xaa
            20                  25

<210> SEQ ID NO 99
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
```

```
<220> FEATURE:
<221> NAME/KEY: misc_feature
<222> LOCATION: (15)..(15)
<223> OTHER INFORMATION: Xaa is K(W)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 99

His Ser Asp Ala Val Phe Thr Glu Gln Tyr Thr Xaa Leu Arg Xaa Gln
 1               5                  10                  15

Leu Ala Xaa Xaa Xaa Tyr Leu Gln Xaa Ile Xaa Xaa
            20                  25

<210> SEQ ID NO 100
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 100

His Ser Asp Ala Val Phe Thr Glu Gln Tyr Thr Xaa Leu Arg Xaa Gln
 1               5                  10                  15
```

Leu Ala Ala Xaa Xaa Tyr Leu Gln Ser Ile Xaa Xaa Cys
            20                  25

<210> SEQ ID NO 101
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 101

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Cys
            20                  25

<210> SEQ ID NO 102
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)

```
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 102

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Xaa Cys
            20                  25

<210> SEQ ID NO 103
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 103

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa
            20                  25

<210> SEQ ID NO 104
<211> LENGTH: 29
<212> TYPE: PRT
```

```
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (29)..(29)
<223> OTHER INFORMATION: Orn

<400> SEQUENCE: 104

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Cys Xaa
            20                  25

<210> SEQ ID NO 105
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
```

```
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 105

His Ser Asp Ala Val Phe Thr Glu Gln Tyr Thr Xaa Leu Arg Xaa Gln
1               5                   10                  15

Cys Ala Xaa Xaa Xaa Tyr Leu Gln Xaa Ile Xaa Xaa
            20                  25

<210> SEQ ID NO 106
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 106

His Ser Asp Ala Val Phe Thr Glu Gln Tyr Thr Xaa Leu Arg Xaa Gln
```

-continued

```
                1               5                  10                 15
Leu Ala Xaa Xaa Xaa Tyr Leu Gln Xaa Ile Xaa Xaa Cys
            20                  25
```

<210> SEQ ID NO 107
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 107

```
His Ser Asp Ala Val Phe Thr Glu Gln Tyr Thr Xaa Leu Arg Xaa Gln
1               5                   10                  15
Leu Ala Xaa Xaa Xaa Tyr Leu Gln Ser Ile Xaa Xaa
            20                  25
```

<210> SEQ ID NO 108
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:

```
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 108

His Ser Asp Ala Val Phe Thr Glu Gln Tyr Thr Xaa Leu Arg Xaa Gln
1               5                   10                  15

Cys Ala Xaa Xaa Xaa Tyr Leu Gln Ser Ile Xaa Xaa
            20                  25

<210> SEQ ID NO 109
<211> LENGTH: 29
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (29)..(29)
<223> OTHER INFORMATION: Orn

<400> SEQUENCE: 109
```

-continued

```
His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Cys Xaa
            20                  25
```

<210> SEQ ID NO 110
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (18)..(18)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 110

```
His Ser Asp Ala Val Phe Thr Glu Gln Tyr Thr Xaa Leu Arg Xaa Gln
1               5                   10                  15

Leu Xaa Ala Xaa Xaa Tyr Leu Gln Ser Ile Xaa Xaa
            20                  25
```

<210> SEQ ID NO 111
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Xaa is K(CO(CH2)2SH)

```
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 111

His Ser Asp Ala Val Phe Thr Glu Gln Tyr Thr Xaa Leu Arg Xaa Gln
1               5                   10                  15

Xaa Ala Xaa Xaa Xaa Tyr Leu Gln Xaa Ile Xaa Xaa
            20                  25

<210> SEQ ID NO 112
<211> LENGTH: 28
<212> TYPE: PRT
<213> ORGANISM: Artificial sequence
<220> FEATURE:
<223> OTHER INFORMATION: Synthetic sequence: VPAC2 receptor peptide
      agonist
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Xaa is K(W)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
```

```
<222> LOCATION: (28)..(28)
<223> OTHER INFORMATION: Orn

<400> SEQUENCE: 112

His Ser Asp Ala Val Phe Thr Glu Gln Tyr Thr Xaa Leu Arg Xaa Gln
1               5                   10                  15

Xaa Ala Xaa Xaa Xaa Tyr Leu Gln Xaa Ile Xaa Xaa
            20                  25

<210> SEQ ID NO 113
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (18)..(18)
<223> OTHER INFORMATION: Xaa is K(CO(CH2)2SPEG40K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 113

His Ser Asp Ala Val Phe Thr Glu Gln Tyr Thr Xaa Leu Arg Xaa Gln
1               5                   10                  15

Val Xaa Ala Xaa Xaa Tyr Leu Gln Ser Ile Xaa Xaa Gly Gly Pro Ser
            20                  25                  30

Ser Gly Ala Pro Pro Ser
        35

<210> SEQ ID NO 114
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
```

```
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (18)..(18)
<223> OTHER INFORMATION: Xaa is K(CO(CH2)2SPEG20K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 114

His Ser Asp Ala Val Phe Thr Glu Gln Tyr Thr Xaa Leu Arg Xaa Gln
1               5                   10                  15

Val Xaa Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 115
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
```

```
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Cys(PEG40K)
<220> FEATURE:
<221> NAME/KEY: MOD_RES
<222> LOCATION: (29)..(29)
<223> OTHER INFORMATION: Orn
<220> FEATURE:
<221> NAME/KEY: MOD_RES
<222> LOCATION: (40)..(40)
<223> OTHER INFORMATION: AMIDATION

<400> SEQUENCE: 115

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Cys Xaa Gly Gly Pro
            20                  25                  30

Ser Ser Gly Ala Pro Pro Pro Ser
        35                  40

<210> SEQ ID NO 116
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: misc_feature
<222> LOCATION: (26)..(26)
<223> OTHER INFORMATION: Cys(PEG40K)
<220> FEATURE:
<221> NAME/KEY: MOD_RES
```

```
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 116

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Cys Xaa Xaa Gly Gly Pro Ser
            20                  25                  30

Ser Gly Ala Pro Pro Pro Ser
        35

<210> SEQ ID NO 117
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Xaa is K(CO(CH2)2SPEG20K)
<220> FEATURE:
<221> NAME/KEY: MOD_RES
<222> LOCATION: (29)..(29)
<223> OTHER INFORMATION: Orn
<220> FEATURE:
<221> NAME/KEY: misc_feature
<222> LOCATION: (40)..(40)
<223> OTHER INFORMATION: Cys(PEG20K)
<220> FEATURE:
```

```
<221> NAME/KEY: MOD_RES
<222> LOCATION: (40)..(40)
<223> OTHER INFORMATION: AMIDATION

<400> SEQUENCE: 117

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Xaa Gly Gly Pro
            20                  25                  30

Ser Ser Gly Ala Pro Pro Pro Cys
        35                  40

<210> SEQ ID NO 118
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Xaa is K(CO(CH2)2SPEG20K)
<220> FEATURE:
<221> NAME/KEY: MOD_RES
<222> LOCATION: (29)..(29)
<223> OTHER INFORMATION: Orn
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 118

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Xaa Xaa Gly Gly Pro
            20                  25                  30
```

```
Ser Ser Gly Ala Pro Pro Cys
        35                  40

<210> SEQ ID NO 119
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Cys(PEG20K)
<220> FEATURE:
<221> NAME/KEY: MOD_RES
<222> LOCATION: (29)..(29)
<223> OTHER INFORMATION: Orn
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 119

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Cys Xaa Gly Gly Pro
            20                  25                  30

Ser Ser Gly Ala Pro Pro Cys
        35                  40

<210> SEQ ID NO 120
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
```

```
        agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Xaa is K(WPEG40K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 120

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Gly Gly Pro Ser
            20                  25                  30

Ser Gly Ala Pro Pro Pro Ser
        35

<210> SEQ ID NO 121
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
```

```
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (29)..(29)
<223> OTHER INFORMATION: Cys(PEG40K)
<220> FEATURE:
<221> NAME/KEY: MOD_RES
<222> LOCATION: (40)..(40)
<223> OTHER INFORMATION: AMIDATION

<400> SEQUENCE: 121

His Ser Asp Ala Val Phe Thr Glu Gln Tyr Thr Xaa Leu Arg Xaa Gln
1               5                   10                  15

Leu Ala Ala Xaa Xaa Tyr Leu Gln Ser Ile Xaa Xaa Cys Gly Gly Pro
            20                  25                  30

Ser Ser Gly Ala Pro Pro Ser
        35                  40

<210> SEQ ID NO 122
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
```

<221> NAME/KEY: misc_feature
<222> LOCATION: (29)..(29)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 122

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Cys Gly Gly Pro
            20                  25                  30

Ser Ser Gly Ala Pro Pro Pro Cys
        35                  40

<210> SEQ ID NO 123
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (29)..(29)
<223> OTHER INFORMATION: Cys(PEG40K)
<220> FEATURE:
<221> NAME/KEY: MOD_RES
<222> LOCATION: (40)..(40)
<223> OTHER INFORMATION: AMIDATION

<400> SEQUENCE: 123

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Cys Gly Gly Pro
            20                  25                  30

Ser Ser Gly Ala Pro Pro Ser
        35              40

<210> SEQ ID NO 124
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (29)..(29)
<223> OTHER INFORMATION: Cys(PEG40K)
<220> FEATURE:
<221> NAME/KEY: MOD_RES
<222> LOCATION: (40)..(40)
<223> OTHER INFORMATION: AMIDATION

<400> SEQUENCE: 124

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Xaa Cys Gly Gly Pro
            20                  25                  30

Ser Ser Gly Ala Pro Pro Ser
        35              40

<210> SEQ ID NO 125
<211> LENGTH: 40

```
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (29)..(29)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 125

His Ser Asp Ala Val Phe Thr Glu Gln Tyr Thr Xaa Leu Arg Xaa Gln
1               5                   10                  15
Leu Ala Xaa Xaa Xaa Tyr Leu Gln Ser Ile Xaa Xaa Cys Gly Gly Pro
            20                  25                  30
Ser Ser Gly Ala Pro Pro Cys
        35                  40

<210> SEQ ID NO 126
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
```

```
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 126

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Gly Gly Pro Ser
            20                  25                  30

Ser Gly Ala Pro Pro Pro Cys Cys
        35                  40

<210> SEQ ID NO 127
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
```

```
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Cys(PEG40K)
<220> FEATURE:
<221> NAME/KEY: MOD_RES
<222> LOCATION: (29)..(29)
<223> OTHER INFORMATION: Orn
<220> FEATURE:
<221> NAME/KEY: MOD_RES
<222> LOCATION: (40)..(40)
<223> OTHER INFORMATION: AMIDATION

<400> SEQUENCE: 127

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Cys Xaa Gly Gly Pro
            20                  25                  30

Ser Ser Gly Ala Pro Pro Pro Ser
        35                  40

<210> SEQ ID NO 128
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
```

```
<220> FEATURE:
<221> NAME/KEY: misc_feature
<222> LOCATION: (17)..(17)
<223> OTHER INFORMATION: Cys(PEG40K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 128

His Ser Asp Ala Val Phe Thr Glu Gln Tyr Thr Xaa Leu Arg Xaa Gln
1               5                   10                  15

Cys Ala Xaa Xaa Xaa Tyr Leu Gln Xaa Ile Xaa Xaa Gly Gly Pro Ser
            20                  25                  30

Ser Gly Ala Pro Pro Pro Ser
        35

<210> SEQ ID NO 129
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
```

```
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (29)..(29)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 129

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Cys Gly Gly Pro
            20                  25                  30

Ser Ser Gly Ala Pro Pro Cys
        35                  40

<210> SEQ ID NO 130
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
```

-continued

```
<222> LOCATION: (22)..(22)
<223> OTHER INFORMATION: Methoxy
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 130

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Xaa Gly Gly Pro Ser
            20                  25                  30

Ser Gly Ala Pro Pro Pro Cys Cys
        35                  40

<210> SEQ ID NO 131
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (27)..(27)
<223> OTHER INFORMATION: Orn
<220> FEATURE:
```

-continued

```
<221> NAME/KEY: misc_feature
<222> LOCATION: (28)..(28)
<223> OTHER INFORMATION: Cys(PEG40K)
<220> FEATURE:
<221> NAME/KEY: MOD_RES
<222> LOCATION: (29)..(29)
<223> OTHER INFORMATION: Orn
<220> FEATURE:
<221> NAME/KEY: MOD_RES
<222> LOCATION: (40)..(40)
<223> OTHER INFORMATION: AMIDATION

<400> SEQUENCE: 131

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Cys Xaa Gly Gly Pro
            20                  25                  30

Ser Ser Gly Ala Pro Pro Pro Ser
            35                  40

<210> SEQ ID NO 132
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Cys(PEG40K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION
```

<400> SEQUENCE: 132

His Ser Asp Ala Val Phe Thr Glu Gln Tyr Thr Xaa Leu Arg Xaa Gln
1               5                   10                  15

Cys Ala Xaa Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 133
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Methoxy
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Cys(PEG20K)
<220> FEATURE:
<221> NAME/KEY: MOD_RES
<222> LOCATION: (29)..(29)
<223> OTHER INFORMATION: Orn
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 133

His Ser Asp Ala Val Phe Thr Glu Gln Tyr Thr Xaa Leu Arg Xaa Gln
1               5                   10                  15

Leu Ala Xaa Xaa Xaa Tyr Leu Gln Ser Ile Xaa Cys Xaa Gly Gly Pro

```
                    20                  25                  30

Ser Ser Gly Ala Pro Pro Pro Cys
        35                  40

<210> SEQ ID NO 134
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (18)..(18)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 134

His Ser Asp Ala Val Phe Thr Glu Gln Tyr Thr Xaa Leu Arg Xaa Gln
1               5                   10                  15

Leu Xaa Ala Xaa Xaa Tyr Leu Gln Ser Ile Xaa Xaa Gly Gly Pro Ser
            20                  25                  30

Ser Gly Ala Pro Pro Pro Cys Cys
        35                  40

<210> SEQ ID NO 135
<211> LENGTH: 39
<212> TYPE: PRT
<213> ORGANISM: Artificial sequence
<220> FEATURE:
```

```
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Xaa is K(CO(CH2)2SPEG20K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 135

His Ser Asp Ala Val Phe Thr Glu Gln Tyr Thr Xaa Leu Arg Xaa Gln
1               5                   10                  15

Xaa Ala Xaa Xaa Xaa Tyr Leu Gln Xaa Ile Xaa Xaa Gly Gly Pro Ser
            20                  25                  30

Ser Gly Ala Pro Pro Pro Cys
        35

<210> SEQ ID NO 136
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
```

```
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Xaa is K(CO(CH2)2SPEG40K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 136

His Ser Asp Ala Val Phe Thr Glu Gln Tyr Thr Xaa Leu Arg Xaa Gln
1               5                   10                  15

Xaa Ala Xaa Xaa Xaa Tyr Leu Gln Xaa Ile Xaa Xaa Gly Gly Pro Ser
                20                  25                  30

Ser Gly Ala Pro Pro Pro Ser
        35

<210> SEQ ID NO 137
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
```

```
<220> FEATURE:
<221> NAME/KEY: misc_feature
<222> LOCATION: (17)..(17)
<223> OTHER INFORMATION: Xaa is K(WPEG40K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 137

His Ser Asp Ala Val Phe Thr Glu Gln Tyr Thr Xaa Leu Arg Xaa Gln
1               5                   10                  15

Xaa Ala Xaa Xaa Xaa Tyr Leu Gln Xaa Ile Xaa Xaa Gly Gly Pro Ser
            20                  25                  30

Ser Gly Ala Pro Pro Pro Ser
        35

<210> SEQ ID NO 138
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
```

```
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Xaa is K(WPEG40K)
<220> FEATURE:
<221> NAME/KEY: MOD_RES
<222> LOCATION: (39)..(39)
<223> OTHER INFORMATION: AMIDATION

<400> SEQUENCE: 138

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Xaa
        35

<210> SEQ ID NO 139
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: misc_feature
<222> LOCATION: (9)..(9)
<223> OTHER INFORMATION: Xaa is K(CO(CH2)2SPEG20K)
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 139

His Ser Asp Ala Val Phe Thr Glu Xaa Tyr Thr Xaa Leu Arg Xaa Gln
1               5                   10                  15
```

Val Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 140
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: misc_feature
<222> LOCATION: (15)..(15)
<223> OTHER INFORMATION: Xaa is K(CO(CH2)2SPEG20K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 140

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 141
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:

-continued

```
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: misc_feature
<222> LOCATION: (28)..(28)
<223> OTHER INFORMATION: Cys(PEG20K)
<220> FEATURE:
<221> NAME/KEY: MOD_RES
<222> LOCATION: (29)..(29)
<223> OTHER INFORMATION: Orn
<220> FEATURE:
<221> NAME/KEY: misc_feature
<222> LOCATION: (40)..(40)
<223> OTHER INFORMATION: Cys(PEG20K)
<220> FEATURE:
<221> NAME/KEY: MOD_RES
<222> LOCATION: (40)..(40)
<223> OTHER INFORMATION: AMIDATION

<400> SEQUENCE: 141

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Cys Xaa Gly Gly Pro
            20                  25                  30

Ser Ser Gly Ala Pro Pro Pro Cys
        35                  40

<210> SEQ ID NO 142
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
```

```
<220> FEATURE:
<221> NAME/KEY: misc_feature
<222> LOCATION: (17)..(17)
<223> OTHER INFORMATION: Cys(PEG20K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 142

His Ser Asp Ala Val Phe Thr Glu Gln Tyr Thr Xaa Leu Arg Xaa Gln
1               5                   10                  15

Cys Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 143
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Cys(PEG20K)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
```

-continued

```
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 143

His Ser Asp Ala Val Phe Thr Glu Gln Tyr Thr Xaa Leu Arg Xaa Gln
1               5                   10                  15

Cys Ala Ala Xaa Xaa Tyr Leu Gln Ser Ile Xaa Xaa Gly Gly Pro Ser
            20                  25                  30

Ser Gly Ala Pro Pro Pro Cys
        35

<210> SEQ ID NO 144
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG30K)
<220> FEATURE:
<221> NAME/KEY: misc_feature
<222> LOCATION: (40)..(40)
<223> OTHER INFORMATION: Cys(PEG30K)
<220> FEATURE:
<221> NAME/KEY: MOD_RES
```

```
<222> LOCATION: (40)..(40)
<223> OTHER INFORMATION: AMIDATION

<400> SEQUENCE: 144

His Ser Asp Ala Val Phe Thr Glu Gln Tyr Thr Xaa Leu Arg Xaa Gln
1               5                   10                  15

Leu Ala Xaa Xaa Xaa Tyr Leu Gln Xaa Ile Xaa Xaa Gly Gly Pro Ser
            20                  25                  30

Ser Gly Ala Pro Pro Pro Cys Cys
        35                  40

<210> SEQ ID NO 145
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Xaa is K(WPEG40K)
<220> FEATURE:
<221> NAME/KEY: MOD_RES
<222> LOCATION: (39)..(39)
<223> OTHER INFORMATION: AMIDATION

<400> SEQUENCE: 145

His Ser Asp Ala Val Phe Thr Glu Gln Tyr Thr Xaa Leu Arg Xaa Gln
1               5                   10                  15
```

```
Leu Ala Xaa Xaa Xaa Tyr Xaa Gln Xaa Ile Xaa Xaa Gly Gly Pro Ser
            20                  25                  30

Ser Gly Ala Pro Pro Pro Xaa
            35
```

<210> SEQ ID NO 146
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (17)..(17)
<223> OTHER INFORMATION: Cys(PEG20K)
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG20K)
<220> FEATURE:
<221> NAME/KEY: MOD_RES
<222> LOCATION: (39)..(39)
<223> OTHER INFORMATION: AMIDATION

<400> SEQUENCE: 146

```
His Ser Asp Ala Val Phe Thr Glu Gln Tyr Thr Xaa Leu Arg Xaa Gln
1               5                   10                  15

Cys Ala Xaa Xaa Xaa Tyr Leu Gln Xaa Ile Xaa Xaa Gly Gly Pro Ser
            20                  25                  30

Ser Gly Ala Pro Pro Pro Cys
            35
```

```
<210> SEQ ID NO 147
<211> LENGTH: 39
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Aib
<220> FEATURE:
<221> NAME/KEY: misc_feature
<222> LOCATION: (20)..(20)
<223> OTHER INFORMATION: Xaa is K(CO(CH2)2SPEG20K)
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: MOD_RES
<222> LOCATION: (39)..(39)
<223> OTHER INFORMATION: AMIDATION

<400> SEQUENCE: 147

His Ser Asp Ala Val Phe Thr Glu Gln Tyr Thr Xaa Leu Arg Xaa Gln
1               5                   10                  15

Val Ala Ala Xaa Xaa Tyr Leu Gln Ser Ile Xaa Xaa Gly Gly Pro Ser
            20                  25                  30

Ser Gly Ala Pro Pro Pro Ser
        35

<210> SEQ ID NO 148
<211> LENGTH: 40
<212> TYPE: PRT
<213> ORGANISM: Artificial sequence
<220> FEATURE:
<223> OTHER INFORMATION: Synthetic sequence: PEGylated VPAC2 receptor
      agonist
<220> FEATURE:
<221> NAME/KEY: MOD_RES
<222> LOCATION: (1)..(1)
<223> OTHER INFORMATION: C6 acylation
<220> FEATURE:
<221> NAME/KEY: MOD_RES
<222> LOCATION: (10)..(10)
<223> OTHER INFORMATION: Methoxy
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
```

```
<223> OTHER INFORMATION: Aib
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (23)..(23)
<223> OTHER INFORMATION: Aib
<220> FEATURE:
<221> NAME/KEY: MOD_RES
<222> LOCATION: (27)..(27)
<223> OTHER INFORMATION: Orn
<220> FEATURE:
<221> NAME/KEY: MOD_RES
<222> LOCATION: (28)..(28)
<223> OTHER INFORMATION: Orn
<220> FEATURE:
<221> NAME/KEY: misc_feature
<222> LOCATION: (39)..(39)
<223> OTHER INFORMATION: Cys(PEG30K)
<220> FEATURE:
<221> NAME/KEY: misc_feature
<222> LOCATION: (40)..(40)
<223> OTHER INFORMATION: Cys(PEG30K)
<220> FEATURE:
<221> NAME/KEY: MOD_RES
<222> LOCATION: (40)..(40)
<223> OTHER INFORMATION: AMIDATION

<400> SEQUENCE: 148

His Ser Asp Ala Val Phe Thr Glu Gln Tyr Thr Xaa Leu Arg Xaa Gln
1               5                   10                  15

Leu Ala Xaa Xaa Xaa Tyr Xaa Gln Ser Ile Xaa Xaa Gly Gly Pro Ser
            20                  25                  30

Ser Gly Ala Pro Pro Pro Cys Cys
        35                  40
```